US010736922B2

(12) United States Patent
Shi et al.

(10) Patent No.: US 10,736,922 B2
(45) Date of Patent: Aug. 11, 2020

(54) HIGH TELOMERASE ACTIVITY BONE MARROW MESENCHYMAL STEM CELLS, METHODS OF PRODUCING THE SAME AND PHARMACEUTICALS AND TREATMENT METHODS BASED THEREON

(71) Applicant: UNIVERSITY OF SOUTHERN CALIFORNIA, Los Angeles, CA (US)

(72) Inventors: Songtao Shi, Thousand Oaks, CA (US); Kentaro Akiyama, Okayama (JP); Chider Chen, Phildelphia, PA (US)

(73) Assignee: University of Southern California, Los Angeles, CA (US)

( * ) Notice: Subject to any disclaimer, the term of this patent is extended or adjusted under 35 U.S.C. 154(b) by 364 days.

(21) Appl. No.: 15/845,718

(22) Filed: Dec. 18, 2017

(65) Prior Publication Data

US 2018/0104281 A1    Apr. 19, 2018

Related U.S. Application Data

(60) Continuation of application No. 14/849,303, filed on Sep. 9, 2015, now abandoned, which is a division of application No. 13/810,878, filed as application No. PCT/US2011/044731 on Jul. 20, 2011, now abandoned.

(60) Provisional application No. 61/366,095, filed on Jul. 20, 2010.

(51) Int. Cl.
*A61K 35/28* (2015.01)
*A61K 31/60* (2006.01)
*C12N 5/0775* (2010.01)
*A61K 35/12* (2015.01)

(52) U.S. Cl.
CPC .............. *A61K 35/28* (2013.01); *A61K 31/60* (2013.01); *C12N 5/0663* (2013.01); *A61K 2035/122* (2013.01); *C12N 2501/02* (2013.01)

(58) Field of Classification Search
None
See application file for complete search history.

(56) References Cited

U.S. PATENT DOCUMENTS

| 2008/0175816 | A1* | 7/2008 | Chen | ...................... | C12M 21/08 424/93.1 |
|---|---|---|---|---|---|
| 2008/0219957 | A1 | 9/2008 | Lim et al. | | |
| 2009/0233353 | A1 | 9/2009 | Furcht et al. | | |
| 2013/0330330 | A1 | 12/2013 | Shi et al. | | |

FOREIGN PATENT DOCUMENTS

WO    2012/012570    1/2012

OTHER PUBLICATIONS

Böcker et al., J. Cell. Mol. Med. vol. 12, No. 4, 2008 pp. 1347-1359 (Year: 2008).*
Chen et al., Journal of Bone and Mineral Research, vol. 22, No. 12, 2007 (Year: 2007).*
Liu et al.,J. Cell. Mol. Med., vol. 12, No. 4, 2008 pp. 1155-1168 (Year: 2008).*
Nadri et al., In Vitro Cell. Dev. Biol.—Animal (2007), vol. 43: 276-282 (Year: 2007).*
Rakian et al., Stem Cell Research & Therapy (2015) 6:235 (Year: 2015).*
Uccelli et al., Trends Immunol. vol. 28, No. 5:219-26, 2007 (Year: 2007).*
Zhang et al (Bone Marrow Transplantation (2009) 43, 69-81 (Year: 2009).*
Zheng et al., J. Adv. Prosthodont, 2014; 6: 351-60 (Year: 2014).*
Akiyama et al. 2012. Characterization of bone marrow derived mesenchymal stem cells in suspension. Stem Cell Research & Therapy, Biomed Central LTD, London GB, vol. 3, No. 5, Oct. 2012, 13 pages.
Gronthos et al. 2003. Molecular and Cellular Charterisation of Highly Purified Strolmal Stem Cells Derived From Human Bone Marrow. Journal of Cell Science. Cambridge University Press, London GB, vol. 116, No. 9, May 2003, pp. 1827-1835.
Jones et al. 2008. Human Bone Marrow Mesenchymal Stem Cells In Vivo. Rheumatology, vol. 47, pp. 126-131.
Prasanna et al. 2010. Pro-inflammatory Cytokines, IFNgamma and TNFalpha, Influence Immune Properties of Human Bone Marrow and Wharton Jelly Mesenchymal Stem Cells Differentially. PLoS One, vol. 5(2): e9016, Feb. 2010, pp. 1-16.
Shetty et al. 2010. Comparison of Proliferative and Multilineage Differentiation Potentials of Cord Matrix, Cord Blood, and Bone Marrow Mesenchymal Stem Cells. Asign J Transfus Sci., vol. 4(a), Jan. 2010, pp. 14-24.
Shi et al. 2002. Nature Biotechnology, vol. 20, Jun. 2002, pp. 587-591.
Tang et al. 2014. Aspirin Treatment Improved Mesenchymal Stem Cell Immunomodulatory Properties via the 15d-PGJ 2 /PPAR[gamma]/ TGF-[beta]1 Pathway. Stem Cells and Development. vol. 23, No. 17, Oct. 2012, pp. 2093-2103.
Sun et al. 2009. Mesenchymal Stem Cell Transplantation Reverses Multiorgan Dysfunction in Systemic Lupus Erythematosus Mice and Humans. Stem Cells, vol. 27, pp. 1421-1432.
Wang et al. 2006. Clinical and Experimental Pharmacology and Physiology, vol. 33, pp. 696-701.
Yamaza et al. 2008. Pharmacologic Stem Cell Based Intervention as a New Approach to Osteoporosis Treatment in Rodents, PLoS One, vol. 3(7): e2615, Jul. 2008, pp. 1-9.
Yamaza et al. 2010. Immunodulatory properties of stem cells from human exfoliated deciduous teeth. Stem Cell Res Ther., vol. 1(1): 5, Mar. 2010, pp. 1-10.
Yen et al. 2009. Brief Report—Human Embryonic Stem Cell-Derived Mesenchymal Progenitors Possess Strong Immunosuppressive Effects Toward Natural Killer Cells as Well as T Lymphocytes. Stem Cells, vol. 27(2), pp. 451-456.

(Continued)

*Primary Examiner* — Scott Long
*Assistant Examiner* — Evelyn Y Pyla
(74) *Attorney, Agent, or Firm* — McDermott Will & Emery LLP

(57) ABSTRACT

Disclosed are isolated human bone marrow mesenchymal stem cells having high telomerase activity (tBMMSCs). Also disclosed are isolated human CD34+ bone marrow mesenchymal stem cells. Also disclosed are bone marrow mesenchymal stem cells treated with a telomerase induction agent.

9 Claims, 46 Drawing Sheets

(56) References Cited

OTHER PUBLICATIONS

European Patent Office, Communication Pursuant to Article 94(3) EPC dated Dec. 16, 2016, which issued in European Application No. 11810369.6.
ISA/US. 2012. International Search Report and Written Opinion of the International Searching Authority, dated May 17, 2012, for PCT application PCT/US11/44731, filed Jul. 20, 2011, corresponding to parent of continuation application.
European Patent Office, Extended European Search Report, dated Feb. 11, 2015, which issued in European Application No. 11810369.6.

* cited by examiner

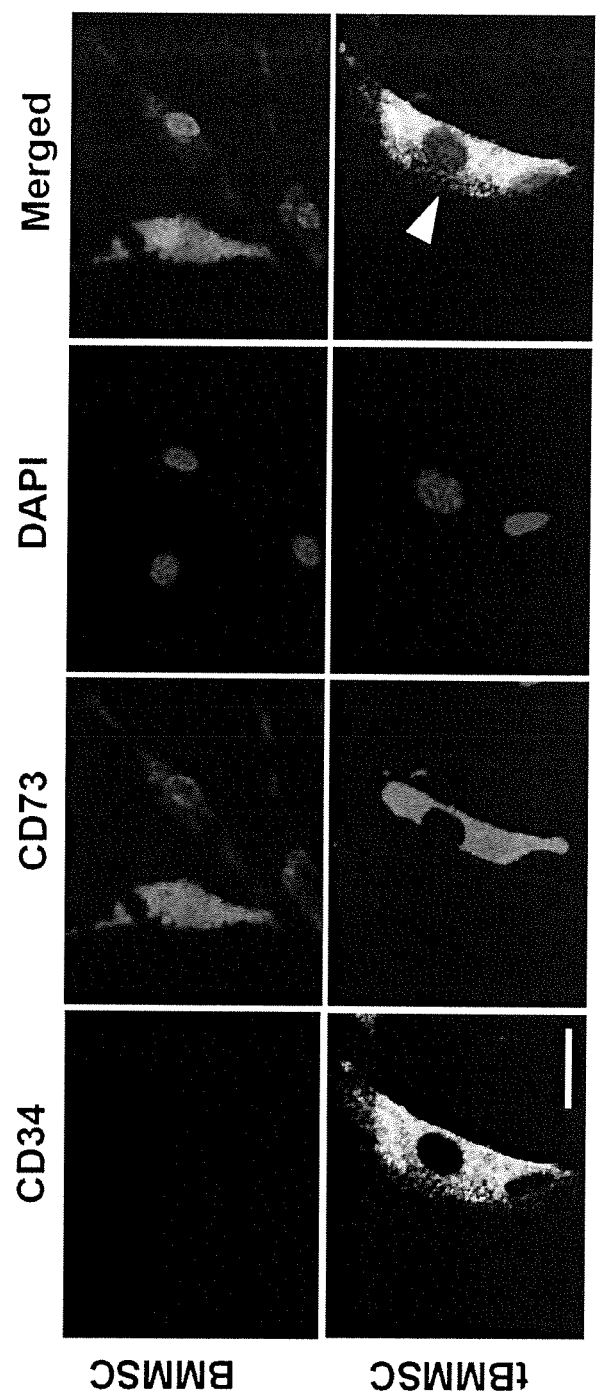

HIGH TELOMERASE ACTIVITY BONE MARROW MESENCHYMAL STEM CELLS, METHODS OF PRODUCING THE SAME AND PHARMACEUTICALS AND TREATMENT METHODS BASED THEREON

CROSS-REFERENCE TO RELATED APPLICATIONS

This application is a continuation application based on U.S. patent application Ser. No. 14/849,303, filed Sep. 9, 2015, entitled "High Telomerase Activity Bone Marrow Mesenchymal Stem Cells, Methods of Producing the Same and Pharmaceuticals and Treatment Methods Based Thereon," which is a divisional of U.S. patent application Ser. No. 13/810,878, filed Aug. 22, 2013, entitled "High Telomerase Activity Bone Marrow Mesenchymal Stem Cells, Methods of Producing the Same and Pharmaceuticals and Treatment Methods Based Thereon," which is a United States national phase application of PCT Application PCT/US11/44731, filed Jul. 20, 2011, entitled High Telomerase Activity Bone Marrow Mesenchymal Stem Cells, Methods of Producing the Same and Pharmaceuticals and Treatment Methods Based Thereon," which is based upon and claims priority to U.S. Provisional Application 61/366,095, filed Jul. 20, 2010, entitled "High Telomerase Activity Bone Marrow Mesenchymal Stem Cells, Methods of Producing the Same and Pharmaceuticals and Treatment Methods Based Thereon." The entire content of each of these applications is incorporated herein by reference.

STATEMENT REGARDING FEDERALLY SPONSORED RESEARCH OR DEVELOPMENT

This invention was made with government support under Contract No. R01DE17449 awarded by the National Institute of Dental and Craniofacial Research/National Institute for Health. The government has certain rights in the invention.

FIELD OF THE INVENTION

The present invention relates in general to bone marrow mesenchymal stem cells, and more specifically to a subset of novel BMMSCs having high telomerase activity, pharmaceutical compositions comprising the BMMSCs, immunomodulation methods using the BMMSCs, and treatment methods for systemic lupus erythemetosis by administration of the BMMSCs.

BACKGROUND OF THE INVENTION

Bone marrow mesenchymal stem cells (BMMSCs) are hierarchical postnatal stem cells capable of self-renewing and differentiating into osteoblasts, chondrocytes, adipocytes, and neural cells (Bianco et al., 2001; Friedenstein et al., 1974; Owen et al., 1988; Pittenger et al., 1999; Prockop et al., 1997).

Due to the heterogeneity of the BMMSCs, there is no single, unique marker allowing for BMMSC isolation, rather an array of cell molecules are utilized to profile BMMSCs. It is widely accepted that BMMSCs express SH2 (CD105), SH3/SH4 (CD73), integrin $\beta_1$ (CD29), CD44, Thy-1 (CD90), CD71, vascular cell adhesion molecule-1 (CD106), activated leukocyte cell adhesion molecule (CD166), STRO-1, GD2, melanoma cell adhesion molecule (CD146), Octamer-4 (Oct4), and stage-specific embryonic antigen-4 (SSEA4) (Conget et al., 1999; Galmiche et al., 1993; Gronthos et al., 2003; Haynesworth et al., 1992; Martinez et al., 2007; Pittenger et al., 1999; Sacchetti et al., 2007; Shi et al., 2003; Simmons et al., 1991; Sordi et al., 2005). It is generally believed that BMMSCs are negative for hematopoietic cell markers such as CD14 and CD34 with a very low level of telomerase activity (Conget et al., 1999; Covas et al., 2008; Galmiche et al., 1993; Haynesworth et al., 1992; Martinez et al., 2007; Pittenger et al., 1995; Sacchetti et al., 2008; Shi et al., 2002, 2003; Sordi et al., 2005). Recent studies have implied that mouse BMMSCs might express the hematopoietic surface molecules, CD45 (Chen et al., 2007) and CD34 (Copland et al., 2008).

BMMSCs are considered to be progenitors of osteoblasts with the capacity to regenerate bone and marrow components in vivo. These findings have led to extensive studies using BMMSCs for mineralized tissue engineering. The clinical evidence appears to support the notion that BMMSC implantation is able to improve cell-based skeletal tissue regeneration (Kwan et al., 2008; Panetta et al., 2009). Recently, evidence has accumulated that BMMSCs produce a variety of cytokines and display profound immunomodulatory properties (Nauta et al., 2007; Uccelli et al., 2007, 2008), perhaps by inhibiting the proliferation and function of several major immune cells such as natural killer (NK) cells, dendritic cells, T and B lymphocytes (Aggarwal and Pittenger, 2005; Nauta et al., 2007; Uccelli et al., 2007, 2008). These unique properties make BMMSCs of great interest for clinical applications in treating immune disorders (Nauta and Fibbe, 2007; Bernardo et al., 2009).

BMMSCs are thought to be derived from bone marrow stromal compartment, initially appearing as adherent, single colony clusters (colony-forming unit-fibroblasts [CFU-F]), and subsequently proliferating on culture dishes (Friedenstein et al., 1980). Adherent BMMSCs are able to proliferate and undergo osteogenic differentiation, providing the first evidence of CFU-F as precursors for osteoblastic lineage (Friedenstein et al., 1980). For over 40 years, the adherent CFU-F assay has been used as an effective approach to identify and select BMMSCs. To date, the CFU-F assay has been considered to be one of the gold standards for BMMSC isolation and expansion (Clarke et al., 1989; Friedenstein et al., 1970).

SUMMARY OF THE INVENTION

Bone marrow mesenchymal stem cells (BMMSCs) are a heterogeneous population of postnatal precursor cells with the capacity of differentiating into multiple cell types and offering alternative treatments for a variety of diseases. We have shown that the standard adherent CFU-F assay collects the majority of BMMSCs, but distinct subpopulations of BMMSCs are sustained in the culture suspension.

One aspect of the present invention is directed to novel subsets of BMMSCs with enhanced therapeutic potential.

Another aspect of the present invention is directed to methods of collecting and isolating the novel BMMSCs of the present invention.

Another aspect of the present invention is directed to methods for inducing the conversion of regular BMMSCs into more therapeutically potent BMMSCs.

Another aspect of the present invention includes isolated human bone marrow mesenchymal stem cells having high telomerase activity. High telomerase activity is most broadly defined as a population of BMMSCs that have higher telomerase activity than Regular BMMSCs, but preferably the isolated subset of human BMMSCs has a telomerase activity of at least two times higher than regular BMMSCs. In a preferred embodiment, at least about 6%, and more preferably at least 20% of the cells of the isolated human bone marrow mesenchymal stem cells of the invention are CD34+.

The isolated human bone marrow mesenchymal stem cells according to the present invention include: (1) isolated BMMSCs derived from non-adherent cells in the plastic culture (hereinafter referred to as "tBMMSCs"); (2) isolated CD34+ BMMSCs, preferably, CD34+/CD73+ BMMSCs; and (3) Human CD34− BMMSCs that have been treated with a telomerase induction agent (e.g. TAT-BMMSCs).

Another aspect of the present invention inventions is directed to pharmaceutical compositions comprising the isolated human bone marrow mesenchymal stem cells according to the present invention. Additionally, the pharmaceutical composition may further comprise a carrier.

Another aspect of the present invention is directed to the separation and isolation of tBMMSCs from a heterogenous population of postnatal precursor cells. tBMMSCs are capable of adhering to extracellular cell matrix (ECM)-coated dishes and showing mesenchymal stem cell characteristics with distinction to hematopoietic cells as evidenced by co-expression of CD73 or CD105 with CD34, forming single colony cluster on ECM, and fail to differentiate into hematopoietic cell lineage.

Another aspect of the present invention is a method of converting regular CD34− BMMSCs to tBMMSCs by treating BMMSCs with telomerase, including aspirin and its related compounds with similar chemical structure.

Another aspect of the present invention is directed to methods of modulating the immune system. The methods of the present invention involve administering to a patient in need thereof an effective amount of the isolated human bone marrow mesenchymal stem cells according to the present invention.

Another aspect of the present invention is directed to treatment methods for systemic lupus erythematosus (SLE) via, without being limited by theory, high levels of nitric oxide (NO) production. The treatment methods include administering to a patient in need thereof an effective amount of the isolated human bone marrow mesenchymal stem cells according to the present invention. This high NO production in the isolated human bone marrow mesenchymal stem cells according to the present invention, for example tBMMSCs, is positively regulated by telomerase activity coupling with the Wnt/beta-catenin signaling. Furthermore, we show that telomerase activator-induced tBMMSCs also exhibit significantly improved immuno-modulatory function, suggesting a feasibility of inducing immuno-activated BMMSCs to improve cell-based therapies for immune disorders.

These and other aspects of the present invention are described with reference to the figures, description, examples, and other disclosures as described herein.

BRIEF DESCRIPTION OF THE FIGURES

(FIG. 1A) Hypothetic model indicates that bone marrow all nuclear cells (ANCs) were seeded at $15 \times 10^6$ into 10 cm culture dishes and incubated for 2 days in the regular culture medium at 37° C. with 5% CO2, and subsequently non-attached cells from culture suspension were transplanted into immunocompromised mice subcutaneously using hydroxyapatite tricalcium phosphate (HA) as a carrier for 8 weeks. Newly formed bone (B) by osteoblasts (open arrows) and associated connective tissue (C) were detected in this non-attached cell transplants by H&E staining. Original magnification; X 200. Bar=100 μm. (FIG. 1B) Hypothetic model of isolating tBMMSCs. Primary ANCs were seeded at $15 \times 10^6$ into 10 cm culture dishes, BMMSCs usually attach on plastic dishes within 2 days, however, a small portion of BMMSCs in primary ANCs failed to attach to the culture dishes and remain in the cell suspension. The cell suspensions containing putative non-attached BMMSCs were collected and transferred to the cultured dishes coated with ECM produced by BMMSCs with generating single colony clusters (CFU-F). These ECM-attached BMMSCs (tBMMSCs) were sub-cultured on regular plastic culture dishes for additional experiments. (FIG. 1C) The number of plastic attached CFU-F generated from $1.5 \times 10^6$ whole bone marrow ANCs is more than 7 folds high than that derived from BMMSC-ECM adherent tBMMSCs. (FIG. 1D) Flow cytometric analysis indicates that tBMMSCs express high levels of mesenchymal stem cell markers CD73 (81.8%), Sca-1 (87.74%), Oct4 (40.7%), and SSEA4 (24.56%) compared to regular BMMSCs (CD73: 70.8%, Sca-1: 52.16%, Oct4: 14.08%). However, it appears that tBMMSCs and BMMSCs express similar level of SSEA-4. (FIG. 1E) Proliferation rates of SSEA4+ tBMMSCs and regular BMMSCs were assessed by BrdU incorporation assay for 24 hrs. The number of positive cells was indicated as a percentage to the total number of each population. The percentage of positive cells is significantly increased in tBMMSCs when compared to control group. (FIG. 1F) tBMMSCs exhibit a significant increase in population doublings when compared to regular BMMSCs.

(FIG. 2A) Flow cytometric analysis showed that regular BMMSCs fail to express CD34, but positive for CD45 antibody staining (21.35%). However, tBMMSCs express both CD34 (23.37%) and CD45 (31.22%). (FIG. 2B) Flow cytometric analysis also showed that CD34+ tBMMSCs were positive anti CD73 (13.8%) and Oct4 (13.41%) antibody staining. None staining groups were used as negative controls. (FIGS. 2C, 2D) Western blot analysis indicates that tBMMSCs express CD34 and mesenchymal surface molecules CD73 and CD105. In contrast, regular BMMSCs only express CD73 and CD105 (C). tBMMSCs express CD34 at passage 1-5 (FIG. 2D). β-actin was used as a sample loading control. BMC: whole bone marrow ANC. (FIGS. 2E, 2F) Immunocytostaining confirms that tBMMSCs are double positive for CD34/CD73 (triangle, FIG. 2E) and CD34/CD105 (triangles, FIG. 2F). Regular BMMSCs are negative for CD34 antibody staining and only positive for anti CD73 (FIG. 2E) and CD 105 (FIG. 2F) antibody staining. Bar=100 (FIG. 2G) tBMMSCs have significant high level of telomerase activity than BMMSCs. HEK293T cells (293T) were used as positive control and heat inactive HEK293T cells (H.I.) were used as negative control measured by a Telo TAGGG Telomerase PCR ELISA kit.

(FIG. 3A) Flow cytometric analysis indicated that aspirin-treated BMMSC (TAT-BMMSC) exhibits positive expression of CD34 when compared to the negative CD34 expression in regular BMMSC (BMMSC). The expression levels of CD45 in TAT-BMMSC were lower than that in BMMSCs and tBMMSC. (FIG. 3B) TAT-BMMSCs express significant high levels of Sca11, Oct4 and CD34 when compared to BMMSCs, but at much lower level than tBMMSC. However, TAT-BMMSC expresses much lower level of CD45 compared to tBMMSC and regular BMMSCs. (FIG. 3C) Western blot analysis showed that tBMMSCs and aspirin-treated BMMSCs express CD34, but BMMSCs fail to express to CD34. The results were representative of five independent experiments. P<0.01; *P<0.005. The graph bar represents mean±SD.

(FIG. 4A) BMMSCs, tBMMSCs and aspirin treated BMMSCs were cultured onto 35 mm low attach culture dish (2×10$^4$/dish) under hematopoietic differentiation medium with or without erythropoietin (EPO; 3 U/mL) for 7 days. Whole bone marrow cells and linage negative bone marrow cells (Linage-cells) were used as positive controls. The results were representative of five independent experiments. (FIG. 4B) Mice received either regular BMMSCs (BMMSC, n=5) or PBS without cells (Control, n=8) failed to survive over 14 days. The whole bone marrow cell infusion group (Whole BM cells, n=3) is a positive control group with survival over 110 days after irradiation. tBMMSCs can extend life span of lethal dose irradiated mice (tBMMSC, n=10). Kaplan-meier survival curves.

(FIG. 5A) NO levels in the supernatant of tBMMSC and regular BMMSC culture (each 0.2×10$^6$/well on 24-well plate) were significantly higher in INF-γ (25 ng/ml)/IL-1β (5 ng/ml)-treated tBMMSC group than in regular BMMSCs. (FIGS. 5B-5J) Anti-CD3 and anti-CD28 (each 1 μg/ml) antibodies-activated spleen (SP) cells (1×10$^6$/chamber) in the upper chambers were co-cultured with or without tBMMSCs or regular BMMSCs (1×10$^5$/chamber) in the bottom chamber using a transwell system. Three days after the co-culture, cell viability of the activated SP cells was assayed using a cell counting kit-8 (FIGS. 5B-5D). tBMMSC-coculture showed a significant reduction on cell viability of activated SP cells compared to the cells cultured without BMMSCs (BMMSC-) and with regular BMMSCs (FIG. 5B). The effects of reducing spleen cell viability by tBMMSCs, but not regular BMMSCs, were abolished in general NOS inhibitor L-NMMA (1 mM)-treated (FIG. 5C) and iNOS specific inhibitor 1400W (0.2 mM)-treated (FIG. 5D) groups. Three days after the co-culture, the activated SP cells in the upper chamber were stained to detect apoptotic cells as described in Materials and Methods (FIGS. 5E-5J). Both tBMMSCs and regular BMMSCs were capable of inducing significant amount of Annexin V (+) early apoptotic cells (FIG. 5E) and Annexin V (+) 7AAD (+) late apoptotic and dead cells (FIG. 5H) compared to negative control groups (BMMSC-). It appeared that tBMMSCs have a significant effect than regular BMMSC in induction of early (FIG. 5E) and late (FIG. 5H) apoptotic cells. Both L-NMMA and 1400W were able to abolish tBMMSC and BMMSC induced Annexin V (+) (FIG. 5F, 5I) and Annexin V (+) 7AAD (+) cells (G, J). It appeared that 1400W treatment has more significant inhibition on tBMMSC-induced early apoptosis of activated SP cells (FIG. 5G). (FIG. 5K-5M) Activated CD4$^+$CD25$^-$ T-cells (1×10$^6$/well) and tBMMSCs or regular BMMSCs (each 0.1×10$^6$/well) were co-cultured in the presence of TGFβ1 (2 ng/ml) and IL-2 (2 ng/ml) with or without NOS inhibitor for 3 days. The floating cells were stained for CD4$^+$ CD8$^-$ CD25$^+$ FoxP3$^+$ regulatory T cells (Treg). tBMMSCs showed a significant effect in up-regulating Foxp3$^+$ regulatory T cells (Treg) (FIG. 5K). However, L-NMMA and 1400W treatments resulted in a abolishing of tBMMSC-induced up-regulation of Treg (FIG. 5L, 5M). The results were representative of, at least, three independent experiments. *P<0.05; P<0.01; *P<0.001. The graph bar represents mean±SD.

(FIG. 6A) A hypothetic model showing that tBMMSCs or regular BMMSCs from C3H/HeJ mice were infused into the tail vein of 10-week-old MRL/lpr mice (0.1×10$^6$cells/10 g of mouse body weight). (FIG. 6B) tBMMSC and BMMSC treatment recover SLE-induced basal membrane disorder and mesangium cell over-growth in glomerular (G) (H&E staining). (FIG. 6C) Urine protein levels were assessed at 2 weeks post BMMSC infusion. Both tBMMSCs and BMMSCs were capable of reducing urine protein levels compared to MRL/lpr group. However, tBMMSCs offered a more significant reduction of urine protein levels compared to regular BMMSCs. (FIGS. 6D, 6E) ELISA quantified that levels of anti dsDNA IgG and IgM antibodies were significantly increased in the peripheral blood of MRL/lpr mice when compared to the undetectable level (N.D.) in controls (C3H). tBMMSC and BMMSC treatments were able to reduce levels of anti dsDNA IgG and IgM, but tBMMSCs show superior treatment effect than BMMSC in reducing dsDNA IgG level (FIG. 6D). (FIG. 6F) tBMMSC and BMMSC treatments were able to significantly reduce anti nuclear antibody (ANA) in MRL/lpr mice, which was significantly increased compared to the control (n=6). But tBMMSC showed better effect in reducing ANA levels compared to BMMSC treatment. (FIG. 6G) tBMMSC and BMMSC treatments were able to increase albumin level compared to the level in MRL/lpr mice), which were significantly decreased compared to the control (n=6). tBMMSC treatments show more effective in elevating albumin level in serum when compared to BMMSC-treated group. (FIG. 6H) Flow cytometric analysis showed that the number of CD25$^+$ Foxp3$^+$ Tregs in CD4$^+$ T lymphocytes of MRL/lpr peripheral blood was reduced as compared to the control). BMMSC and tBMMSC treatments elevated the number of Tregs. It appeared that tBMMSCs induced a more significant elevation of Treg levels than BMMSCs. (FIG. 6I) Flow cytometry revealed that MRL/lpr mice had significantly increased level of CD4$^+$ IL17$^+$IFNg$^-$ T lymphocytes (Th17 cells) in spleen compared to control group. The Th17 cells were markedly decreased in BMMSC and tBMMSC treated groups. tBMMSC treatment induced a more significant reduction of Th17 cells than BMMSCs. The results were representative of six independent experiments. *P<0.05; P<0.01; *P<0.001. The graph bar represents mean±SD.

(FIGS. 7A, 7B) tBMMSCs were cultured with telomerase inhibitor III (1 μM) for one week. Telomerase activity (FIG. 7A) and NO production (FIG. 7B) were significantly reduced in telomerase inhibitor treatment group. 293T cells and heat-inactivated samples were used as positive and negative control, respectively. (FIG. 7C-7E) Regular BMMSCs were cultured with aspirin or Telomerase inhibitor III (Telo I, 1 µM) for one week. Aspirin can elevate telomerase activity (FIG. 7C), telomerase reverse transcriptase (TERT) expression (FIG. 7D) and NO production (FIG. 7E) in BMMSCs. In contrast, Telomerase inhibitor III reduces telomerase activity (C) and NO production (FIG. 7E). (FIG. 7F) In aspirin treatment group, a Wnt inhibitor, DKK1 (DKK, 10 ng/ml), was added to the BMMSC cultures for three days (DKK-TAT), which led to a significantly reduction of NO levels compared to aspirin (TAT) group. (FIG. 7G) Western blot analysis showed that DKK1 can reduce active β-catenin levels. Aspirin (TAT) treatment can partially block DKK1-induced down-regulation of activated beta-catenin expression. (FIG. 7H) DKK1 treatment was able to abolish aspirin (TAT)-induced telomerase activity in BMMSCs (DKK-TAT). (FIG. 7I) When BMMSCs were cultured with Chiron, activator of beta catenin signaling, at 1 and 10 µM for 1 week. NO production in BMMSCs was significantly increased in a dose dependent manner as measured by Total NO/Nitrite/Nitrate kit. (FIG. 7J) Western blot analysis confirmed that Chiron treatment induces up-regulated expression of active beta-catenin in BMMSCs. (FIG. 7K) Chiron treatment is able to induce a high telomerase activity, which is blocked by telomerase inhibitor III (Telo i-Chiron) when used prior to the Chiron induction. 293T cell and heat inactivated sample were used as positive and negative control respectively. (FIG. 7L) Chiron induced high NO production can be blocked by telomerase inhibitor III treatment. The results were representative of five independent experiments. *P<0.05; P<0.01; *P<0.001. The graph bar represents mean±SD.

(FIG. 8A) Urine protein levels were assessed at 2 weeks post BMMSC infusion. Both BMMSCs and aspirin (TAT) treated BMMSCs (TAT-BMMSC) were capable of reducing urine protein levels compared to MRL/lpr group. However, TAT-BMMSC offered a more significant reduction of urine protein levels compared to regular BMMSCs when $0.1 \times 10^6$ or $0.01 \times 10^6$ cells were systemically infused. It appeared that $0.01 \times 10^6$ BMMSCs failed to reduce urine protein level compared to MRL/lpr mice. (FIGS. 8B, 8C) ELISA quantified that levels of anti dsDNA IgG and IgM antibodies were significantly increased in the peripheral blood of MRL/lpr mice when compared to the controls (C3H). TAT-BMMSC and BMMSC treatments were able to reduce levels of anti dsDNA IgG and IgM, but TAT-BMMSC show superior treatment effect than BMMSC in reducing dsDNA IgG and IgM levels. TAT-BMMSC of $0.01 \times 10^6$ cell infusion group was able to significantly reduce the levels of anti dsDNA IgG and IgM. (FIG. 8D) TAT-BMMSC and BMMSC treatments were able to significantly reduce anti nuclear antibody (ANA) in MRL/lpr mice, which was significantly increased compared to the control (C3H). But TAT-BMMSC of $0.01 \times 10^6$ cell infusion group showed better effect in reducing ANA levels compared to BMMSC treatment. (FIG. 8E) ELISA analysis showed that TAT-BMMSC and BMMSC treatments were able to reduce serum IL17 levels compared to the high level in MRL/lpr mice. However, TAT-BMMSC of $0.01 \times 10^6$ cell infusion group showed more effective in reducing IL17 level in serum when compared to BMMSC-treated group. (FIG. 8F) Flow cytometry revealed that MRL/lpr mice had significantly increased level of $CD4^+$ $IL17^+IFNg^-$ T lymphocytes (Th17 cells) in spleen compared to control group (C3H). The Th17 cells were markedly decreased in TAT-BMMSC and BMMSC treated groups. TAT-BMMSC treatment induced a more significant reduction of Th17 cells than BMMSC groups. (FIG. 8G) Flow cytometric analysis showed that the number of $CD25^+$ $Foxp3^+$ Tregs in $CD4^+$ T lymphocytes of MRL/lpr peripheral blood was reduced as compared to the control (C3H). TAT-BMMSC and BMMSC treatments elevated the number of Tregs. It appeared that TAT-BMMSCs induced a more significant elevation of Treg levels than BMMSCs when $0.01 \times 10^6$ cells were systemically infused. The results were representative of six independent experiments. *P<0.05; P<0.01; *P<0.001. The graph bar represents mean±SD.

(FIG. 9A) human tBMMSCs (htBMMSC) showed significantly high level telomerase activity than BMMSCs (hBMMSC) as measured by Telo TAGGG Telomerase PCR ELISA kit. 293T cells and heat inactive (H.I.) were used as positive and negative controls, respectively. (FIG. 9B) htBMMSCs produce high level of NO than that of hBMMSCs as assessed by Total NO/Nitrite/Nitrate kit. (FIG. 9C) Kynurenine production was significantly increased in htBMMSC compare to hBMMSC (p<0.005). (FIG. 9D) When hBMMSC or htBMMSC were co-cultured with active T cell, the kynurenine level in co-culture system was dramatically increased with more significantly increase in htBMMSC group compare to hBMMSC group. (FIG. 9E) Annexin V and 7AAD double positive apoptotic cell numbers in active T cells were increased when co-cultured with hBMMSC or htBMMSC. However, apoptotic cell rate was significantly increased in htBMMSC group compared to hBMMSC group. The results were representative of three independent experiments. *P<0.05; P<0.01; *p<0.005. The graph bar represents mean±SD.

(FIG. 11A) Alizarin Red S and alkaline phosphatase (ALP) staining showed that tBMMSCs were similar to regular BMMSCs in osteogenic differentiation in vitro. (FIG. 11B) tBMMSCs or regular BMMSCs ($4 \times 10^6$ cells/transplant) were transplanted into immunocompromised mice using HA/TCP (HA) as a carrier for 8 weeks. Bone formation was detected in tBMMSC and BMMSC transplants, evidenced by H&E staining. HA; hydroxyapatite tricalcium phosphate, B; bone, M; bone marrow, C; connective tissue; Original magnification; X 200. Bar=50 µm. (FIG. 11C) tBMMSCs are capable of forming Oil Red O positive cells and expression of PPARγ2 and LPL mRNA as seen in regular BMMSCs by Oil Red O staining and RT-PCR analysis, respectively. Glyceraldehyde 3-phosphate dehydrogenase (GAPDH) was used as an internal control. The results were representative of five independent experiments. Scale bars=100 µm. 1: negative control, 2: BMMSC, 3: tBMMSC. (FIG. 11D) Chondrogenic differentiation was assessed by Alcian blue staining for acidic sulfated mucosubstances, Pollak's Trichrome staining for collagen, and immunohystochemical staining for collagen type II. tBMMSCs were able to differentiate into chondrocytes as observed in regular BMMSCs. Bar=50 μm. The results were representative of three independent experiments. The graph bar represents mean±SD.

(FIG. 12A) The collected culture supernatant was used to measure NO level. The results were representative of five independent experiments. (FIG. 12B) Western blot analysis showed that iNOS expression was inhibited by LNMMA and 1400W. *P<0.05; ***P<0.001. The graph bar represents mean±SD.

(FIG. 13A) TRAP staining indicated the increased number of TRAP positive cells in epiphysis of the distal femurs of MRL/Ipr mice as compared to the control (C3H). tBMMSC and BMMSC infusion resulted in a significant reduced number of TRAP positive cells. It appears that tBMMSC group shows more significant reduction of number of TRAP positive cells than BMMSC group. (FIGS. 13B, 13C) ELISA revealed that MRL/Ipr mice have increased levels of soluble RANKL (sRANKL) (FIG. 13B) and C-terminal telopeptides of type I collagen (CTX) (FIG. 13C) in serum as compared to the controls. tBMMSC and BMMSC infusion can significantly reduce levels of sRANKL (FIG. 13B) and CTX (FIG. 13C), but tBMMSC group showed a more effective in reduce levels of sRANKL (FIG. 13B) and CTX (FIG. 13C). The results were representative of five independent experiments. *P<0.05; P<0.01; *P<0.001. The graph bar represents mean±SD.

DETAILED DESCRIPTION OF THE INVENTION

Figure 1A:
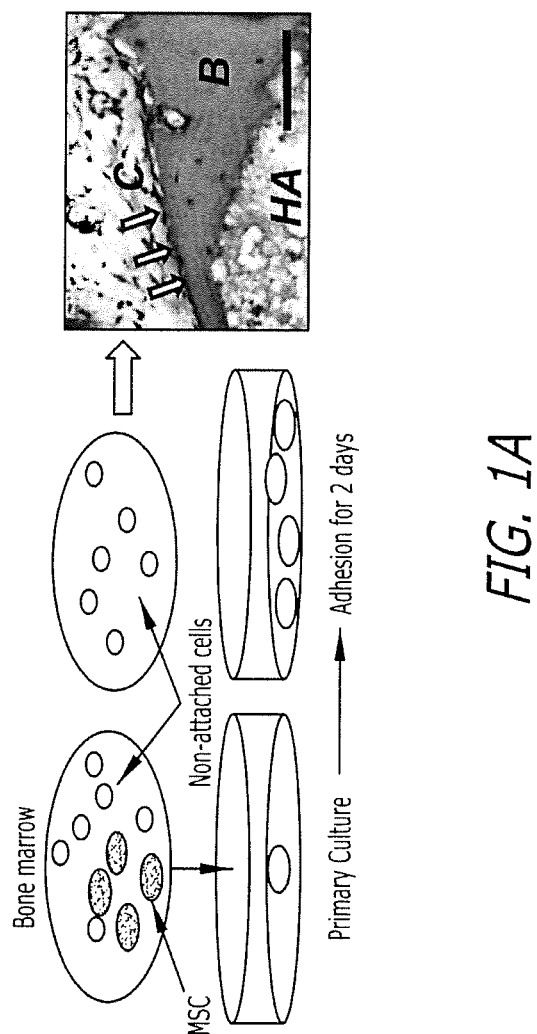
FIGS. 1A-1F show that tBMMSCs are capable of attaching on ECM-coated culture dish.

Abbreviations
BMMSCs: bone marrow mesenchymal stem cells;
CFU-F: colony-forming units fibroblastic;
ECM: extracellular cell matrix;
Oct4: Octamer-4;
SSEA4: stage specific embryonic antigen-4;
SLE: systemic lupus erythematosus;
HA/TCP: hydroxyapatite tricalcium phosphate;
Tregs: CD4+CD25+Foxp3+ regulatory T cells;
ANCs: all nuclear cells
Definitions
Unless otherwise indicated herein, all terms used herein have the meanings that the terms would have to those skilled in the art of the present invention. Practitioners are particularly directed to current textbooks for definitions and terms of the art. It is to be understood, however, that this invention is not limited to the particular methodology, protocols, and reagents described, as these may vary.

Individual cells and cell populations will be referred to herein by use of a '+' or a '−' symbol to indicate whether a certain cell or cell population expresses or lacks a specific marker, e.g. a CD molecule. When used in connection with a single cell, the use of a '+' or a '−' symbol indicates whether that cell expresses or lacks the specific marker. For example, a "CD34+", CD31−" cell is one that expresses CD34, but not CD31. When used in connection with cell populations, the use of a '+' or a '−' symbol to indicate whether a certain cell population, or a portion thereof, expresses or lacks the specific marker.

As used herein, so-called "regular BMMSCs" are BMMSCs appearing as adherent, single colony clusters (colony-forming unit-fibroblasts [CFU-F]) on regular plastic culture, and subsequently proliferating on culture dishes (Friedenstein et al., 1980).

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

An "therapeutically effective amount" of tBMMCs is an amount sufficient to carry out a specifically stated purpose. An "effective amount" may be determined empirically and in a routine manner in relation to the stated purpose.

A "Carrier" or "Carriers" as used herein include pharmaceutically acceptable carriers, excipients, or stabilizers which are nontoxic to the cell or mammal being exposed thereto at the dosages and concentrations employed. The physiologically acceptable carrier may be a sterile aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

One aspect of the present invention is directed to unique subsets of isolated human bone marrow mesenchymal stem cells having high telomerase acitivity. High telomerase activity is most broadly defined as a population of BMMSCs that have higher telomerase activity than Regular BMMSCs, but preferably the isolated subset of human BMMSCs has a telomerase activity of at least two times higher than regular BMMSCs. Isolated human BMMSCs having high telomerase activity according to the present invention are generally characterized by having an increased expression of CD34 relative to regular BMMSCs. Preferably, at least about 6%, and more preferably at least 20% of the cells of the isolated human bone marrow mesenchymal stem cells of the invention are CD34+. In its broadest sense, the term "isolated" when used in connection with a population of cells of interest, means that the population of cells is at least partially isolated from other cell types or other cellular material with which it naturally occurs in the tissue of origin (e.g., bone marrow). In another embodiment, the isolated stem cells also are substantially free of soluble, naturally occurring molecules.

The isolated human bone marrow mesenchymal stem cells according to the present invention include: (1) isolated human BMMSCs derived from non-adherent cells in the plastic culture (hereinafter referred to as "tBMMSCs"); (2) isolated CD34$^+$ BMMSCs, preferably, CD34$^+$/CD73$^+$ BMMSCs; and (3) Human CD34$^-$ BMMSCs that have been treated with a telomerase induction agent (e.g. TAT-BMMSCs). Unless otherwise specifically stated, all BMMSCs in the present invention are human BMMSCs.

The human bone marrow useable in connection with the present invention may generally be obtained from within human bone. Preferably, the bone marrow is postnatal bone marrow. All nucleated cells of the bone marrow are typically used. Most preferably, bone marrow derived all nuclear cells (ANCs) from femurs and tibias are used as described herein.

Specific cell types described and identified herein may be isolated from collected cells employing techniques known by those skilled in the art, such as for example, but not limited to density gradient centrifugation, magnet cell separation, flow cytometry, affinity cell separation or differential adhesion techniques. In a preferred embodiment, the stem cells of the present invention can be purified by, for example, flow cytometry (e.g., FACS analysis), as discussed below. The high telomerase BMMSCs described herein will undergo ex vivo expansion according to known methods for BMMSCs to enrich cell numbers for tissue regeneration or systemic therapies.

Isolated tBMMSCs tBMMSCs are generally isolated from a heterogenous population of postnatal precursor cells. Isolated tBMMSCs are generally characterized as human BMMSCs that fail to form single colony clusters (CFU-F) in plastic cultures but are capable of adhering on mesenchymal stem cell-produced ECM and exhibit increased expression of telomerase relative to regular human BMMSCs. tBMMSCs show mesenchymal stem cell characteristics with distinction to hematopoietic cells as evidenced by co-expression of CD73 or CD105 with CD34. tBMMSCs fail to differentiate into hematopoietic cell lineage.

Another aspect of the present invention is directed to a method of isolating tBMMSCs comprising: culturing a sample of bone marrow derived all nuclear cells on a plastic substrate; removing cells that do not adhere to the plastic substrate; culturing the removed cells on a BMMSC-ECM coated medium; and collecting colonies forming attached cells on the BMMSC-ECM medium.

More specifically, tBMMSCs may be produced and isolated as follows: Primary ANCs are seeded on plastic substrate, for example plastic culture dishes. tBMMSCs in primary ANCs fail to attach to the culture dishes and remain in the cell suspension. The cell suspensions containing putative non-attached tBMMSCs are collected and transferred to cultured dishes coated with Extracellular matrix (ECM) produced by BMMSCs, resulting in the generation of single colony clusters (CFU-F). These ECM-attached BMMSCs (tBMMSCs) are sub-cultured according to known methods on regular plastic culture. Typical flow cytometric analysis indicates that tBMMSCs express high levels of mesenchymal stem cell markers CD73 (e.g. about 80%), Sca-1 (e.g. about 90%), and Oct4 (e.g. about 40%)compared to regular BMMSCs (CD73: e.g. about 70%, Sca-1: about 50%, Oct4: about 14%). However, it appears that tBMMSCs and BMMSCs express similar level of SSEA-4.

tBMMSCs express CD34 and possess high telomerase activity relative to regular BMMSCs. As described herein, regular BMMSCs fail to express CD34, but are positive for CD45 (about 20%). However, tBMMSCs express both CD34 (about 25%) and CD45 (about 30%). Western blot analysis indicates that tBMMSCs express CD34 and mesenchymal surface molecules CD73 and CD105. In contrast, regular BMMSCs only express CD73 and CD105. tBMMSCs also have significantly higher levels of telomerase activity than regular BMMSCs.

To ensure purity of tBMMSCs, it is preferred to isolate and substantially purify tBMMSCs that express a marker known to be expressed in regular BMMSCs selected from the group consisting of STRO-1, CD29, CD73, CD90, CD105, CD146, Octamer-4 (Oct4), and stage-specific embryonic antigen-4 (SSEA4). In a preferred embodiment, SSEA4$^+$ tBMMSCs may be isolated and purified by techniques generally known to those of ordinary skill, such as immune FACS. A sample of tBMMSCs stem cells is "substantially pure" when it is at least 80%, or at least 90%, or at least 95%, and, in certain cases, at least 99% free of cells other than cells of interest. Thus, for example, a sample of SSEA4$^+$ tBMMSCs stem cells is "substantially pure" when it is at least 80%, or at least 90%, or at least 95%, and, in certain cases, at least 99% free of cells other than SSEA4$^+$ tBMMSCs. Purity can be measured by any appropriate method, for example, by fluorescence-activated cell sorting (FACS), or other assays which distinguish cell types.

Isolated CD34$^+$ Human BMMSCs

CD34$^+$ BMMSCs are distinct from regular BMMSCs in terms of having elevated telomerase activity and high levels of the earlier mesenchymal stem cell marker, Oct4, along with increased immunomodulatory function. The mechanism that may contribute to the up-regulated immunomodulatory function is associated with high NO production in tBMMSCs (Ren et al., 2008) and NO-driven high Treg level (Niedbala et al., 2007), which appears to be governed by telomerase activity coupled with Wnt/beta-catenin signaling. Without being limited to theory, this is believed to be the reason that tBMMSCs have a superior therapeutic effect in treating SLE mice.

Isolated CD34$^+$ BMMSCs fail to form CFU-F in plastic cultures but are capable of adhering on mesenchymal stem cell-produced ECM and differentiating into osteoblasts, adipocytes, and chondrocytes from both C3H/HeJ and C57BL/6J mice. CD34$^+$ BMMSCs coexpress mesenchymal stem cell markers CD73 and CD105. Furthermore, CD34$^+$ BMMSCs are distinct from HSC due to the fact that they are not able to differentiate into hematopoietic cell lineage in vitro and fail to rescue lethal dose irradiated mice.

Preferably, the isolated human BMSSCs are double positive for CD34 and at least one other marker known to be expressed in regular BMMSCs selected from the group consisting of STRO-1, CD29, CD73, CD90, CD105, CD146, Octamer-4 (Oct4), and stage-specific embryonic antigen-4 (SSEA4). Preferably, the BMMSCs are both CD34$^+$ and CD73$^+$. Preferably, Isolated CD34$^+$ BMMSCs are substantially pure. A sample of CD34$^+$ BMMSCs is "substantially pure" when it is at least 80%, or at least 90%, or at least 95%, and, in certain cases, at least 99% free of cells other than cells of interest. Thus, for example, a sample (population) of CD34$^+$ BMMSCs is "substantially pure" when it is at least 80%, or at least 90%, or at least 95%, and, in certain cases, at least 99% free of cells other than CD34$^+$ BMMSCs. Purity can be measured by any appropriate method, for example, by fluorescence-activated cell sorting (FACS), or other assays which distinguish cell types.

As described herein, about 4% of human BMMSC's cells are double positive for CD34 and CD73 in whole bone marrow ANCs. These CD34$^+$/CD73$^+$ cells can be sorted out and isolated from bone marrow using conventional techniques, such as a flow cytometric sorter. The use of flow cytometry to isolate CD34+/CD73+ BMMSCs from whole bone marrow offers a practical approach to isolate and collect tBMMSC for clinical therapeutic use. CD34+/CD73+ cells can be sorted out and isolated from tBMMSCs and from regular BMMSCs that have been treated with a telomerase induction agent as described herein. Preferably, the CD34+/CD73+ BMMSCs are "substantially pure." A group of CD34+/CD73+ BMMSCs are "substantially pure" when it is at least 80%, or at least 90%, or at least 95%, and, in certain cases, at least 99% free of cells other than CD34+/CD73+ BMMSCs.

CD34+/CD73+ cells form CFU-F on BMMSC-ECM cultures at frequency similar to tBMMSCs. CD34+/CD73+ BMMSCs also show higher telomerase activity than regular BMMSCs. CD34+/CD73+ BMMSCs also show a significant increase in NO production compared to regular BMMSCs.

CD34− BMMSCs Treated with a Telomerase Induction Agent

Another aspect of the present invention directed to a method of increasing telomerase activity in CD34− human bone marrow mesenchymal stem cells comprising: contacting human bone marrow messenchymal stem cells with an effective amount of a telomerase inducing agent. The CD34− BMMSCs may, for example, be regular BMMSCs. As defined herein, a group of BMMSCs is CD34− if less than about 1% of the group is CD34+.

The telomerase activity of the CD34− BMMSCs can be increased by adding an effective amount of telomerase induction agent to the culture medium. One preferred telomerase induction agent is aspirin, but structural and functional analogues of aspirin may be substituted. The culture conditions may be appropriately determined by those of ordinary skill by measurement of the telomerase activity levels as described herein. When aspirin is used, it is preferably added into culture medium at about 2 µg/ml to about 50 µg/ml for about 1 week. Culture under these conditions results in significantly increased level of telomerase activity in BMMSCs was achieved.

In one specific embodiment, regular human BMMSC are treated with a telomerase induction agent to become BMMSCs having high telomerase activity with improved immunomodulatory function. Specifically, when aspirin is added into culture medium at 2.5 µg/ml or 50 µg/ml for 1 week, significantly increased level of telomerase activity in BMMSCs was achieved. The resulting BMMSCs are referred to herein as TAT-BMMSCs. TAT-BMMSCs exhibits positive expression of CD34 when compared to the negative CD34 expression in regular BMMSCs. The expression levels of CD45 in TAT-BMMSC were lower than that in BMMSCs and tBMMSC. TAT-BMMSCs express significant high levels of Sca11, Oct4 and CD34 when compared to BMMSCs, but at much lower level than tBMMSC. However, TAT-BMMSC expresses much lower level of CD45 compared to tBMMSC and regular BMMSCs. Western blot analysis showed that tBMMSCs and aspirin-treated BMMSCs express CD34, but BMMSCs fail to express to CD34.

Therapeutic Applications of High Telomerase Activity BMMSCs

Another aspect of the present invention is directed to using the BMMSCs of the present invention in the treatment of one or more disorders.

Another aspect of the present inventions is directed to a method of immunomodulation comprising administering to a patient in need thereof a therapeutically effective amount of isolated human bone marrow mesenchymal stem cells of the present invention.

Another aspect of the present invention is directed to a method of increasing the NO concentration in vivo, comprising administering to a patient in need thereof a therapeutically effective amount of the isolated human bone marrow mesenchymal stem cells of the present invention. NO is a gaseous biological mediator with important roles in affecting macrophage and T cell function (Sato et al., 2007; Bogdan et al., 2001). iNOS is induced by IFNγ, TNFα, IL-1α, or IL-1β in BMMSCs, and iNOS−/− mice show a reduced ability to suppress T cell functions (Ren et al., 2008). It has been reported that active endothelial NOS along with estrogen receptor cooperatively regulates human telomerase revere transcriptase (hTERT) expression in the endothelium (Grasselli et al., 2008). We describe herein the functional role of high telomerase activity in improving immunomodulatory activity of BMMSCs via elevation of approximately 10 µM NO production and approximately 5% up-regulation of Treg. Telomerase-enhanced NO production is also associated with Wnt/β-catenin signaling, in which Wnt inhibitor DKK1 can block telomerase activator-induced telomerase activity and the associated NO production in BMMSCs. Furthermore, Wnt activator Chiron is able to promote telomerase activity and NO production in BMMSCs. Pre-treatment with telomerase inhibitor can partially abolish Wnt-activator-induced telomerase activity. These data suggest that telomerase coupled with Wnt/beta-catenin signaling to promote NO production. Therefore, in addition to the functional role in participating in the Wnt/beta-catenin signaling pathway (Park et al., 2009), telomerase also collaborates with Wnt/beta-catenin signaling to modulate NO production. Both telomerase and Wnt/beta-catenin activators can induce a high NO production in regular BMMSCs leading to an improved reduction of activated SP cell viability. But only telomerase activator treatment is capable of enhancing apoptosis of activated SP cells. It is possible that other immunomodulatory factors may also contribute to elevated immunomodulation of tBMMSC.

Another aspect of the present invention is directed to the treatment of systemic lupus erythematosus comprising administering to a patient in need thereof a therapeutically effective amount of the isolated human bone marrow mesenchymal stem cells of the present invention.

As used herein, the term an "effective amount" of the BMMSCs of the present invention, when used in connection with a method, is an amount of the BMMSCs sufficient to carry out a specifically stated purpose. In general, an "effective amount" in reference to treatment of a disease or disorder may be determined empirically by reference to the data and standards disclosed herein and in a routine manner in relation to the stated purpose. An effective amount is preferably given in a single dose to the patient; however, the effective amount may be delivered to the patient as a number of doses over a period of time. As describe herein, the dosage of 0.1×10⁶ cells/10 g body weight are sufficient to treat SLE mice in case of regular BMMSC. By using high telomerase activity BMMSCs, the dosage can be reduced to 0.01×10⁶ cells/10 g body weight with therapeutic effect. Those of ordinary skill can apply this to treatment of humans using known models relating mouse to human dosages and using known techniques for optimization of dosages.

The present invention further includes a pharmaceutical composition comprising an effective amount of pharmaceutical composition comprising isolated bone marrow mesenchymal stem cells having high telomerase activity in a carrier medium. The pharmaceutical compositions of the present invention are used for administration of the isolated bone marrow mesenchymal stem cells having high telomerase activity for treatment in accordance with any of the methods described herein.

In the methods described herein, the BMMSCs of the present invention should be compatible with the patient and be administered in a therapeutically effective amount of the BMMSCs. The therapeutically effective amount can range from the maximum number of cells that is safely received by the patient to the minimum number of cells necessary for to achieve the intended effect. One of ordinary skill in the art can determine and optimize effective amounts according to known techniques to effectuate the intended purpose of the treatment.

The therapeutically effective amount of the BMMSCs can be suspended in a pharmaceutically acceptable carrier. Such a carrier may include but is not limited to a suitable culture medium plus 1% serum albumin, saline, buffered saline, dextrose, water, and combinations thereof. The formulation should suit the mode of administration.

In a preferred embodiment, the BMMSC preparation or composition is formulated for systemic administration to human beings in accordance with procedures for pharmaceutical formulations knows to those of ordinary skill. Typically, compositions for systemic administration are solutions in sterile isotonic aqueous buffer. The ingredients may be supplied either separately or mixed together in unit dosage form, for example, as a cryopreserved concentrate in a hermetically sealed container such as an ampoule indicating the quantity of active agent.

A variety of means for administering cells to subjects will, in view of this specification, be apparent to those of skill in the art. Such methods include may include systemic administration or injection of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The cells may be prepared for delivery in a variety of different forms. For example, the cells may be suspended in a solution or gel. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the isolated human BMMSCs include but are not limited to systemic intravenous or intra-arterial injection and injection directly into the tissue at the intended site of activity. The preparation can be administered by any convenient route, for example by infusion or bolus injection and can be administered together with other biologically active agents. Administration is preferably systemic. It may be advantageous, under certain conditions, to use a site of administration close to or nearest the intended site of activity. When the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration of the BMMSCs of this invention may be done in combination with one or more further therapeutic agents including simultaneous (concurrent) and consecutive administration in any order.

EXAMPLES

The following examples are provided in order to demonstrate and further illustrate certain embodiments and aspects of the present invention and are not to be construed as limiting the scope thereof. While such examples are typical of those that might be used, other procedures known to those skilled in the art may alternatively be utilized. Indeed, those of ordinary skill in the art can readily envision and produce further embodiments, based on the teachings herein, without undue experimentation.

Experimental Methods

Animals. Female C3H/HeJ, C57BL/6J, and C3MRL-$Fas^{lpr}$/J mice were purchased from Jackson Lab. Female immunocompromised mice (Beige nude/nude XIDIII) were purchased from Harlan. All animal experiments were performed under the institutionally approved protocols for the use of animal research (USC #10874 and 10941).

Antibodies. Anti Oct4, SSEA4, active β catenin and β catenin were purchased from Millipore. Anti Sca-1-PE, CD34-PE, CD34-FITC, CD45-PE, CD73-PE, CD4-PerCP, CD8-FITC, CD25-APC, CD3ε and CD28 antibodies were purchased from BD Bioscience. Anti CD105-PE, Foxp3-PE, IL17-PE, and IFNγ-APC antibodies were purchased from eBioscience. Unconjugated anti CD34, CD73, and CD105, and anti TERT were purchased from Santa Cruz Biosciences. Anti β actin antibody was purchased from Sigma.

Isolation of mouse bone marrow mesenchymal stem cells (BMMSCs). The single suspension of bone marrow derived all nuclear cells (ANCs) from femurs and tibias were seeded at $15 \times 10^6$ into 100 mm culture dishes (Corning) under 37° C. at 5% $CO_2$ condition. Non-adherent cells were removed after 48 hours and attached cells were maintained for 16 days in alpha minimum essential medium (α-MEM, Invitrogen) supplemented with 20% fetal bovine serum (FBS, Equitech-bio), 2 mM L-glutamine, 55 µM 2-mercaptoethanol, 100 U/ml penicillin, and 100 µg/ml streptomycin (Invitrogen). Colonies-forming attached cells were passed once for further experimental use.

Preparation of Extracellular Matrix (ECM) coated dishes. ECM coated dishes were prepared as described in Chen et al. (2007). Briefly, 100% confluence of BMMSCs was cultured in culture medium with 100 nM L-ascorbic acid phosphate (Wako Pure Chemical). After 2 weeks, cultures were washed with PBS and incubated with 0.005% Triton X-100 (Sigma) for 5-10 min at room temperature to remove cells. The ECM was treated with DNase I (100 units/ml; Sigma) for 1 h at 37° C. The ECM was washed with PBS three times and stored in 2 ml of PBS containing 100 U/ml penicillin, 100 µg/ml streptomycin, and 0.25 µg/ml fungizone (Invitrogen) at 4° C.

Isolation of tBMMSCs. Bone marrow-derived ANCs were seeded at $15 \times 10^6$ into 100 mm culture dishes and cultured for 48 hrs. The culture supernatant were collected and centrifuged to obtain putative non-attached BMMSCs. The cells were re-seeded at indicated numbers on ECM-coated dishes. After 48 hrs, the floating cells in the cultures were removed with PBS and the attached cells on ECM were maintained for additional 14 days. Colonies-forming attached cells were passed once and sub-cultured on regular plastic culture dishes for further experiments. For some stem cell characterization analysis, we collected SSEA4 positive tBMMSCs using FACS$^{Calibur}$ flow cytometer (BD Bioscience) and expanded in the cultures.

Colony forming unit-fibroblastic (CFU-F) assay. One million cells of ANCs from bone marrow were seeded on T25 cell culture flask (Nunc). After 16 days, the cultures were washed by PBS and stained with 1% toluidine blue solution in 2% paraformaldehyde (PFA). The cell cluster that has more than 50 cells was counted as a colony under microscopy. The colony number was counted in five independent samples per each experimental group.

Cell proliferation assay. The proliferation of BMMSC and tBMMSC was performed by bromodeoxyuridine (BrdU) incorporation assay. Each cell population ($1 \times 10^4$ cells/well) were seeded on 2-well chamber slides (Nunc) and cultured for 3 days. The cultures were incubated with BrdU solution (1:100) (Invitrogen) for 20 hours, and stained with a BrdU staining kit (Invitrogen). BrdU-positive and total cell numbers were counted in ten images per subject. The BrdU assay was repeated in 5 independent samples for each experimental group.

Population doubling assay. $0.5 \times 10^6$ cells of BMMSCs and pBMMSCs were seeded on 60 mm culture dishes at the first passage. Upon reaching confluence, the cells were passaged at the same cell density. The population doubling was calculated at every passage according to the equation: $\log_2$ (number of harvested cells/number of seeded cells). The finite population doublings were determined by cumulative addition of total numbers generated from each passage until the cells ceased dividing.

Flow cytometric analysis of mesenchymal stem cell surface molecules. BMMSCs or pBMMSCs ($0.2 \times 10^6$) were incubated with 1 □g of PE conjugated antibodies or isotype-matched control IgGs (Southern Biotech) at 4° C. for 45 min. Samples were analyzed by FACS$^{Calibur}$ flow cytometer (BD Bioscience). For dual color analysis, the cells were treated with PE conjugated and FITC conjugated antibodies or isotype-matched control IgGs (each 1 □g). The cells were analyzed on FACS$^{Calibur}$ (BD Bioscience).

Immunofluorescent microscopy. The cells subcultured on 8-well chamber slides (Nunc) ($2 \times 10^3$/well) were fixed with 4% PFA. The samples were incubated with the specific or isotype-matched mouse antibodies (1:200) overnight at 4° C., and treated with Rhodamine-conjugated secondary antibodies (1:300, Jackson ImmunoResearch; Southern Biotechnology). Finally, they were mounted by Vectashield mounting medium containing 4',6-diamidino-2-phenylindole (DAPI) (Vector Laboratories).

Isolation of $CD34^+CD73^+$ double positive cells. Bone marrow derived ANCs were stained with anti CD34-FITC and anti CD73-PE antibodies for 30 min on ice under dark condition. After wash with PBS, cells were re-suspended into OPTI-MEM (Invitrogen) supplement with 2% FBS and antibiotics (100 U/ml penicillin and 100 µg/ml streptomycin) and sorted by MOFLO XDP Cell Sorter (BECKMAN Coulter). The sorted double positive cells were seeded on ECM coated 60 mm dish at density of $1 \times 10^6$/dish and cultured for further experiments.

In vivo bone formation assay. $4.0 \times 10^6$ of cells were mixed with hydroxyapatite/tricalcium phosphate (HA/TCP) ceramic powders (40 mg, Zimmer Inc.) and subcutaneously transplanted into 8weeks old immunocompromised mice. After 8 weeks, the transplants were harvested, fixed in 4% PFA and then decalcified with 5% EDTA (pH 7.4), followed by paraffin embedding. The paraffin sections were stained with hematoxylin and eosin (H&E) and analyzed by an NIH Image-J. The newly-formed mineralized tissue area from five fields was calculated and shown as a percentage to total tissue area.

In vitro osteogenic differentiation assay. BMMSCs and tBMMSCs were cultured under osteogenic culture condition containing 2 mM β-glycerophosphate (Sigma), 100 µM L-ascorbic acid 2-phosphate and 10 nM dexamethasone (Sigma). After induction, the cultures were stained with alizarin red or alkaline phosphatase.

In vitro adipogenic differentiation assay. For adipogenic induction, 500 nM isobutylmethylxanthine, 60 µM indomethacin, 500 nM hydrocortisone, 10 µg/ml insulin (Sigma), 100 nM L-ascorbic acid phosphate were added into the culture medium. After 10 days, the cultured cells were stained with Oil Red-O and positive cells were quantified by using an NIH Image-J. Total RNA was also isolated from cultures after 10 days induction for further experiments.

Reverse transcriptase polymerase chain reaction (RT-PCR) analysis. Extraction of total RNA and RT-PCR were performed according to standard procedures.

Western blotting analysis. 20 mg of protein were used and SDS-PAGE and western blotting were performed according to standard procedures. β-actin on the same membrane served as the loading control.

Inhibitor treatment. tBMMSCs and BMMSCs were treated with 1 mM L-NMMA (Cayman Chemical) or 0.2 mM 1400 W (Cayman Chemical) to inhibit total NOS or iNOS, respectively. Aspirin 50 µg/ml (TAT) and telomerase inhibitor III (1 µM; EMD Chemicals) were used to activate and suppress telomerase activity in cultured BMMSCs, respectively. CHIRON 99021 (1 or 10 µM; Chiron Corporation) and Dickkopf 1 (DKK1, 10 ng/ml, R&D Systems) were used as an activator and inhibitor to regulate β catenin levels in BMMSCs.

Measurement of telomerase activity. The Telomerase activity was measured using TeloTAGGG Telomerase PCR ELISA kit (Roche).

Measurement of nitric oxide production. BMMSCs ($0.2 \times 10^6$/well) were cultured on 24-well plates with or without cytokines (IFNγ, 25 ng/ml; IL-1β, 5 ng/ml, R&D Systems) and chemicals (L-NMMA, 1 mM; 1400W, 0.2 mM; aspirin, 50 µg/ml; Telomerase inhibitor III, 1 µM; CHIRON 99021, 1 or 10 µM; DKK1, 10 ng/ml) at indicated concentration and days. The same chemical concentration was also used in combination treatment such as DKK and aspirin or Telomerase inhibitor and CHIRON99021. The supernatant from each culture was collected and measured nitric oxide concentration using Total Nitric Oxide and Nitrate/Nitrite Parameter Assay kit (R&D Systems) according to manufacturer's instruction.

Cell apoptosis and cell survival assay. Transwell system (Corning) was used for co-culture experiments. $0.2 \times 10^6$ of tBMMSCs or BMMSCs were seeded on each lower chamber. In the upper chambers, activated splenocytes ($1 \times 10^6$/chamber), which were pre-stimulated with plate-bounded anti CD3ε antibody (5 µg/ml) and soluble anti CD28 antibody (2 µg/ml) for 3 days, were loaded. Both chambers were filled with a complete medium containing Dulbecco's Modified Eagle Medium (DMEM, Lonza) with 10% heat-inactivated FBS, 50 µM 2-mercaptoethanol, 10 mM HEPES, 1 mM sodium pyruvate (Sigma), 1% non-essential amino acid (Cambrex), 2 mM L-glutamine, 100 U/ml penicillin and 100 mg/ml streptomycin. To measure the splenocyte viability, cell counting kit-8 (Dojindo Molecular Technoloies) were used. For apoptosis of splenocyte analysis, Annexin V-PE apoptosis detection kit I (BD Bioscience) were used and analyzed on FACS$^{Calibur}$ (BD Bioscience).

In vitro CD4$^+$CD25$^+$Foxp3$^+$Tregs induction. CD4$^+$ CD25$^-$ T-lymphocytes (1×10$^6$/well), collected by CD4$^+$ CD25$^+$ regulatory T-cell Isolation kit (Miltenyi Biotec), were pre-stimulated with plate bounded anti CD3E antibody (5 µg/ml) and soluble anti CD28 antibody (2 µg/ml) for 3 days. These activated T-lymphocytes were loaded on 0.2× 10$^6$ of BMMSC or tBMMSC cultures with recombinant human TFGβ1 (2 µg/ml) (R&D Systems) and recombinant mouse IL2 (2 µg/ml) (R&D Systems). After 3 days, cells in suspension were collected and stained with anti CD4-PerCP, anti CD8a-FITC, anti CD25-APC antibodies (each 1 µg) for 45 min on ice under dark condition. And then cells were stained with anti Foxp3-PE antibody (1 µg) using Foxp3 staining buffer kit (eBioscience) for cell fixation and permeabilization. The cells were analyzed on FACS$^{Calibur}$ (BD Bioscience).

Allogenic mouse tBMMSC transplantation into MRL/lpr mice. Under general anesthesia, C3H/HeJ-derived BMMSCs or tBMMSCs (0.1×10$^6$ cells/10 g body weight) were infused into MRL/lpr mice via tail vein at 10 weeks old age (n=6). In control group, MRL/lpr mice received PBS (n=5). All mice were sacrificed at 12 weeks old age for further analysis. The protein concentration in urine was measured using Bio-Rad Protein Assay (Bio-Rad,). The number of white blood cells from peripheral blood was measured by Coulter LH-750 (BECKMAN Coulter).

Measurement of autoantibodies, albumin, sRANKL and CTX. Peripheral blood serum samples were collected from mice. Autoantibodies, albumin, sRANKL and CTX were analyzed by enzyme-linked immunosorbent assay (ELISA) method using commercial available kits (anti-dsDNA antibodies, ANA, and albumin, alpha diagnostic; sRANKL, R&D Systems; CTX, Nordic Bioscience Diagnostics A/S) according to their manufactures' instructions. The results were averaged in each group. The intra-group differences were calculated between the mean values.

TRAP staining. Deparaffinized sections were re-fixed with a mixture of 50% ethanol and 50% acetone for 10 min. TRAP-staining solutions were freshly made (1.6% naphthol AS-BI phosphate in N,N-dimethylformamide and 0.14% fast red-violet LB diazonium salt, 0.097% tartaric acid and 0.04% MgCl$_2$ in 0.2 M sodium acetate buffer, pH 5.0) and mixed in 1:10. The sections were incubated in the solution for 10 min at 37° C. under shield and counterstained with toluidine blue. All regents for TRAP staining were purchased from Sigma.

Histometry. Area of trabecular bone was measured on bone sections with H&E staining. To quantify osteoclast activity in the bones, number of mature osteoclasts was determined by TRAP positive cells attached on the bone surface. Each number of cells and area were measured from five representative images per each sample using an NIH Image-J, followed by calculating the means. The data were average the means in each experimental group. The results were shown as each indicated percentage.

Rescue lethal dose irradiated mice. In each group, 1×10$^6$ cells in 50 ml PBS or PBS alone as control were injected into the tail vein of recipient mice at 1 day post lethal irradiation (8.5 Gy per mouse). The survival date of each mouse was recorded and analyzed.

Statistics. Student's t-test was used to analyze statistic difference. The p values less than 0.05 were considered significant.

Example 1

Figure 1B:
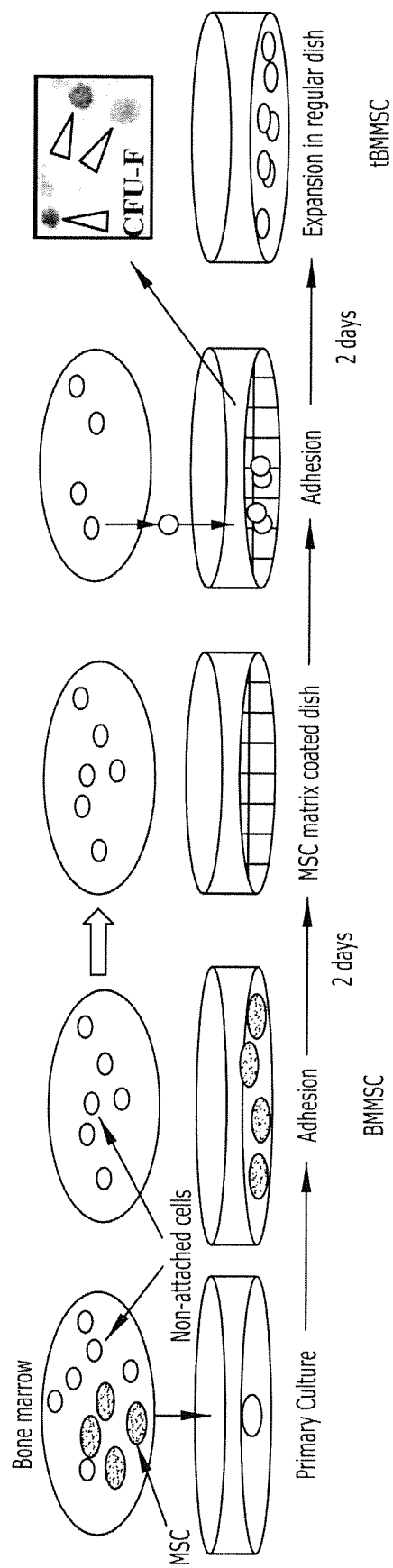
Figure 1C:
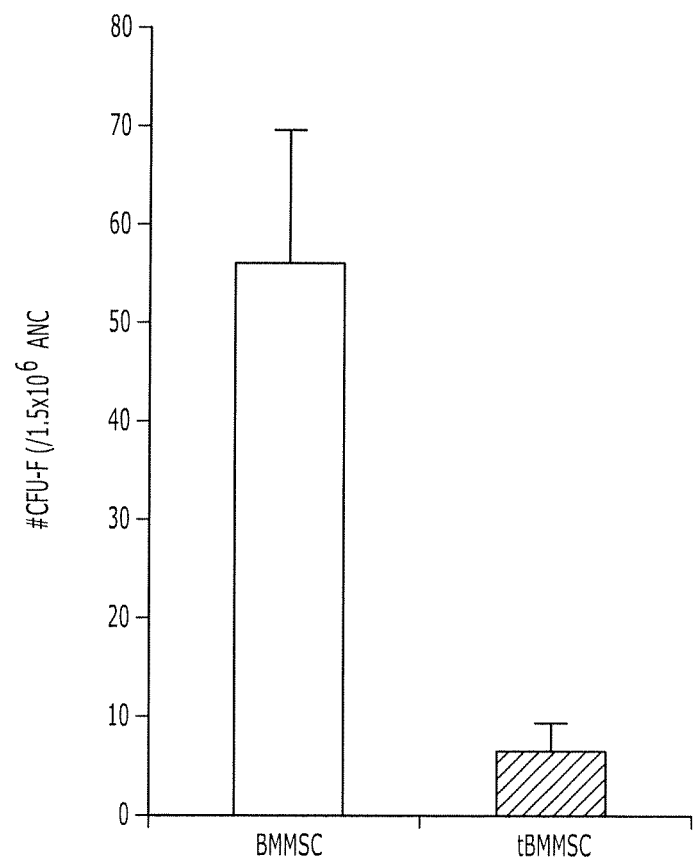
Figure 1D:
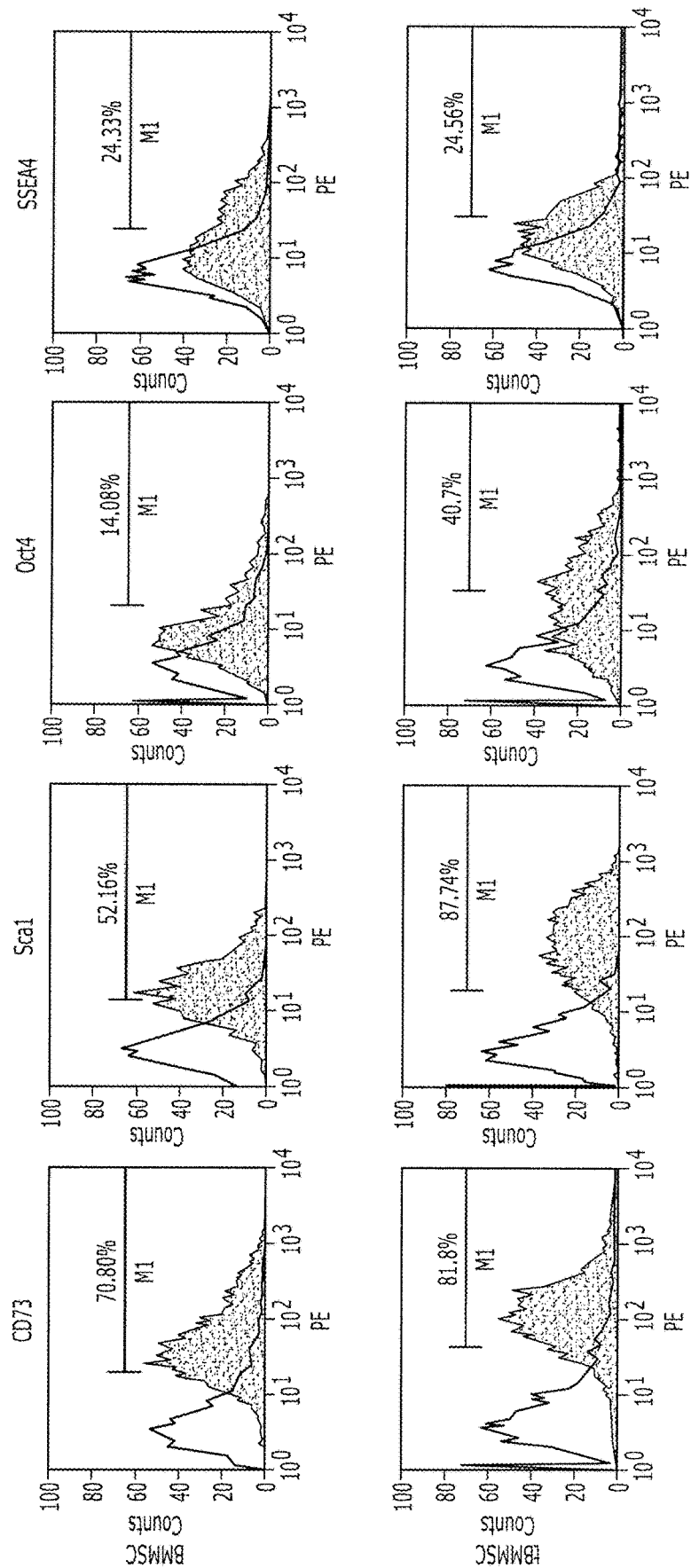
Figure 1E:
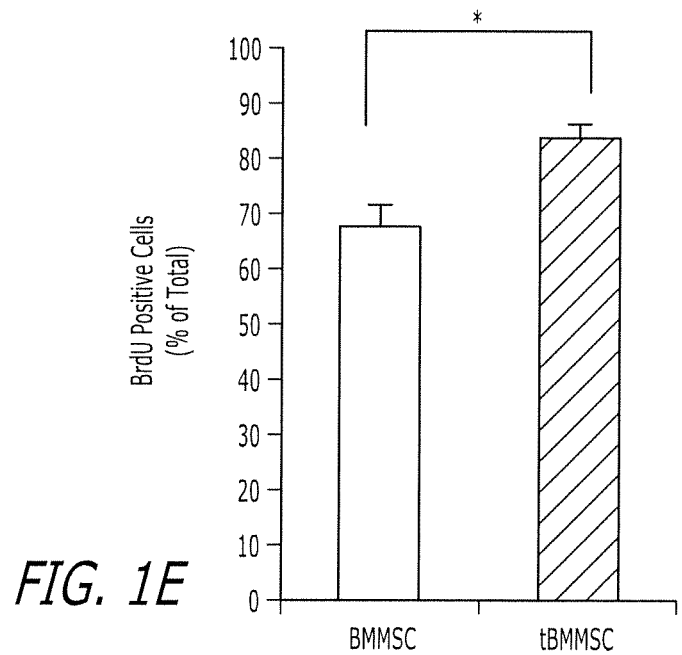
Figure 1F:
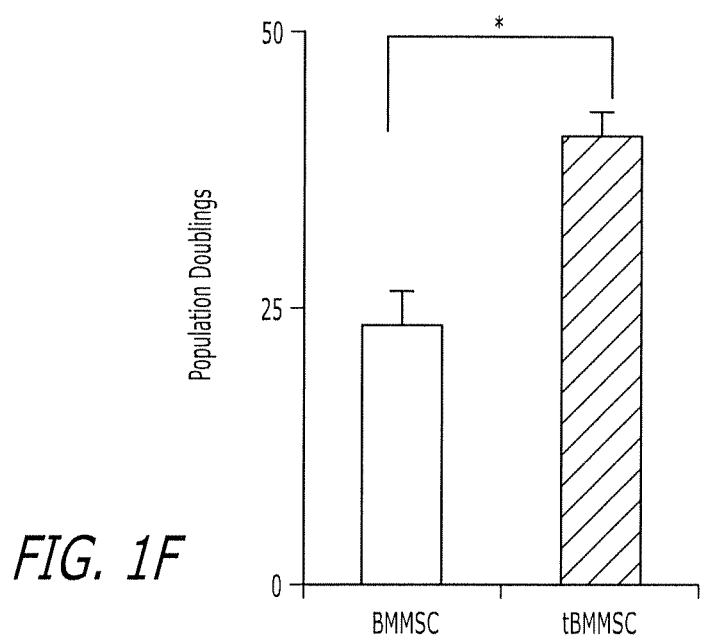
Figure 10:
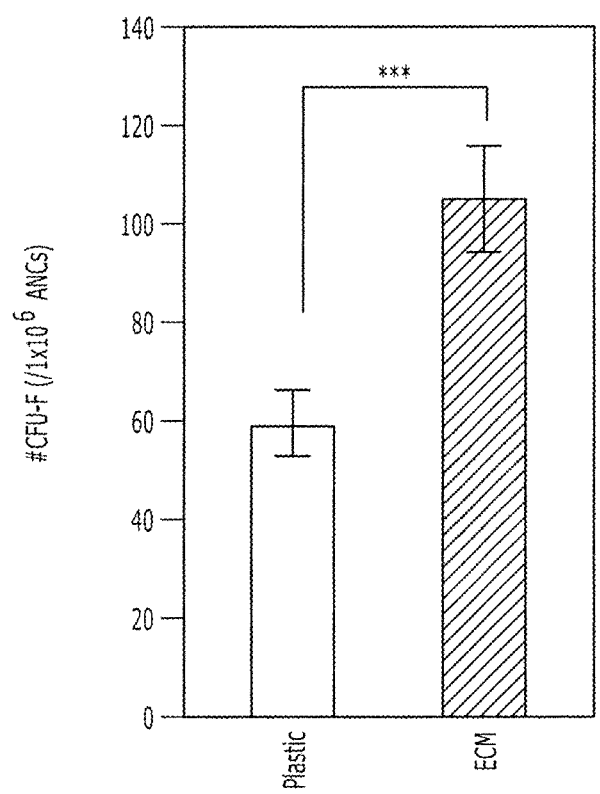
FIG. 10 shows the number of CFU-F in BMMSC cultures. Primary ANCs were seeded at $1 \times 10^6$ into 6 cm normal plasticculture dishes (Plastic) or the culture dishes coated with ECM produced by BMMSCs (ECM) for 14 days. The CFU-F number was significantly increased in BMMSCs cultured in ECM coated dishes. The results were representative of five independent experiments. ***P<0.001. The graph bar represents mean±SD.

A Subset of BMMSCs Fails to Adhere to Plastic Culture Dishes, but Attaches to ECM-Coated Culture Dishes To determine whether a subset of BMMSCs remains in culture suspension, we seeded 15×10$^6$ bone marrow all nuclear cells (ANCs) under regular plastic culture conditions for 2 days and subsequently transplanted all non-attached cells into immunocompromised mice subcutaneously using hydroxyapatite tricalcium phosphate (HA/TCP) as a carrier. At 8 weeks post-transplantation, newly formed bone was identified in the transplants by H&E staining (FIG. 1A), suggesting that the BMMSC culture suspension may contain cells with a capacity of differentiating into bone forming cells in vivo. Added evidence indicated that extracellular matrix (ECM) produced by BMMSCs (BMMSC-ECM) can adhere higher numbers of CFU-F when compared to plastic cultures (FIG. 10; Chen et al., 2007). Thus, we collected culture medium at 2 days post-primary CFU-F culture and loaded the medium onto BMMSC-ECM-coated dishes (FIG. 1B). A subset of BMMSCs (named tBMMSCs) in the suspension was able to adhere to the BMMSC-ECM and form CFU-F (FIG. 1B), at a lower incidence compared to the number of CFU-F generated from regular BMMSCs (FIG. 1C). tBMMSCs were found to express mesenchymal stem cell associated markers (CD73, stem cell antigen 1 [Sca-1], Octamer 4 [Oct4], and stage specific antigen 4 [SSEA4]) as evidenced by flow cytometric analysis (FIG. 1D). When compared with regular BMMSCs, tBMMSCs expressed significantly higher levels of Sca-1 (87.74% vs. 52.16% in BMMSCs) and Oct4 (40.7% vs. 14.08% in BMMSCs), both earlier progenitor surface molecules for mesenchymal stem cells. In order to characterize stem cell properties of tBMMSCs, we collected SSEA4 positive tBMMSCs and assessed their proliferation rate by bromodeoxyuridine (BrdU) labeling. We found that tBMMSCs had a significantly elevated BrdU uptake rate compared to regular BMMSCs (FIG. 1E). In addition, we used a continuous cell culture assay to indicate that SSEA4$^+$ tBMMSCs acquired a significantly increased number of population doubling (FIG. 1F). These data imply that tBMMSCs are distinct from regular BMMSCs in terms of attachment, proliferation, and self-renewal.

Figure 11A:
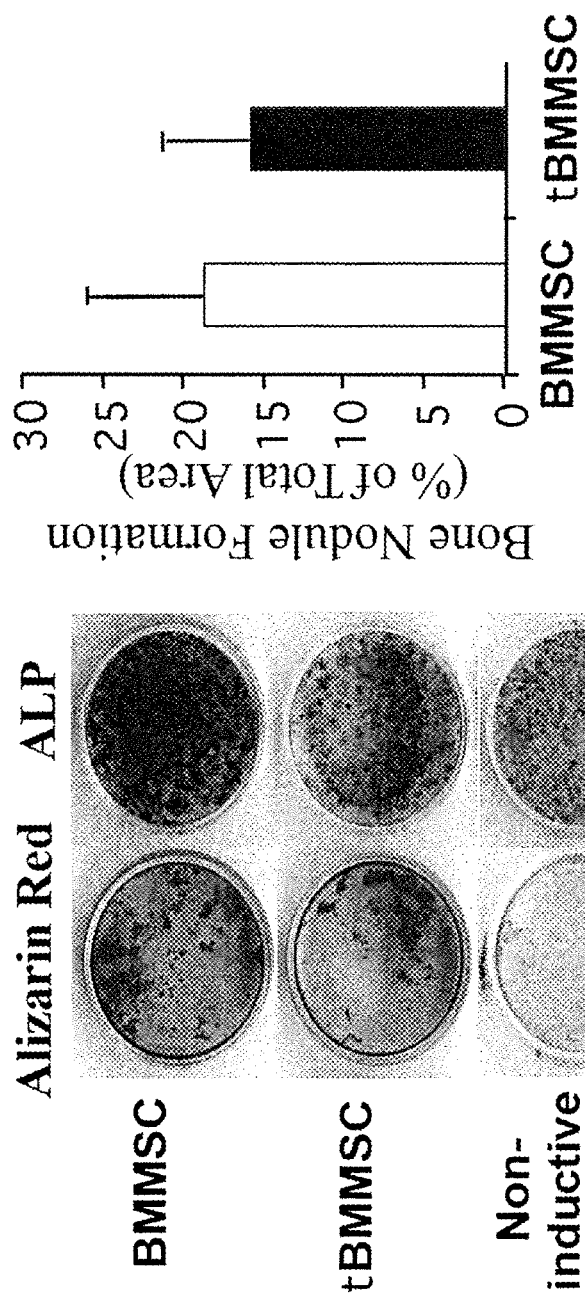
FIGS. 11A-D show the multipotent differentiation of tBMMSCs.
Figure 11B:
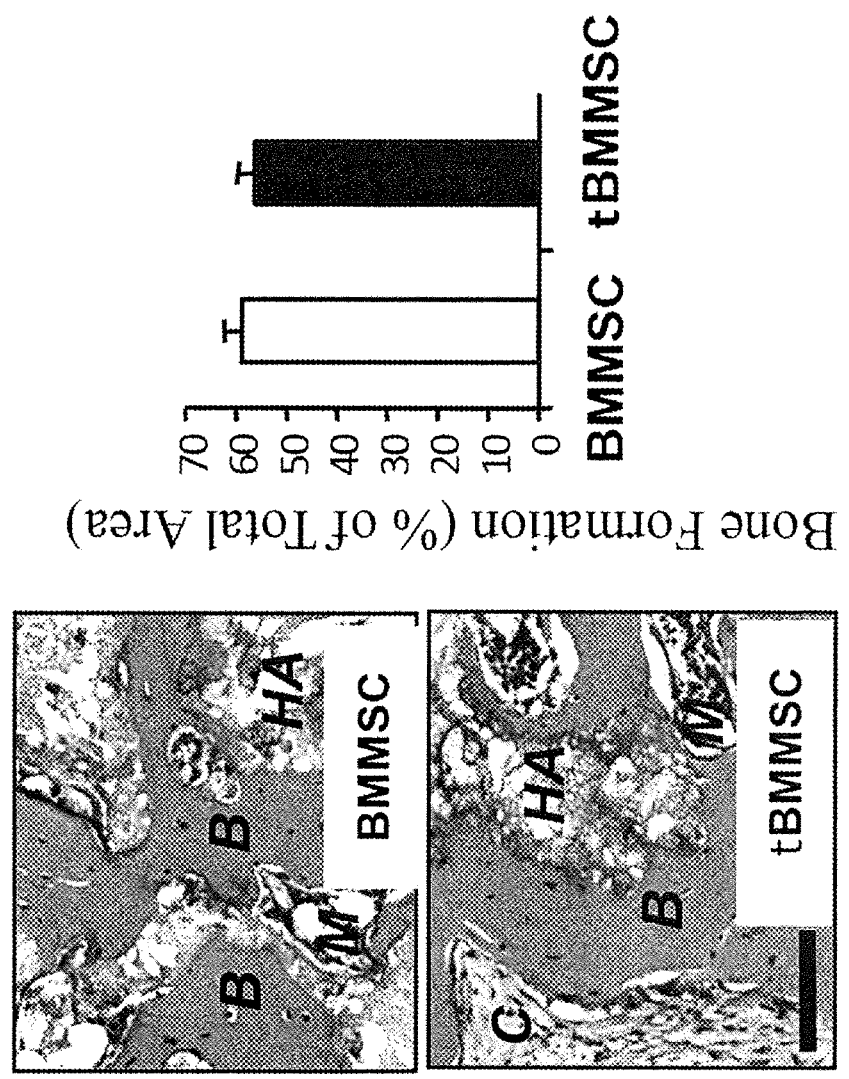
Figure 11C:
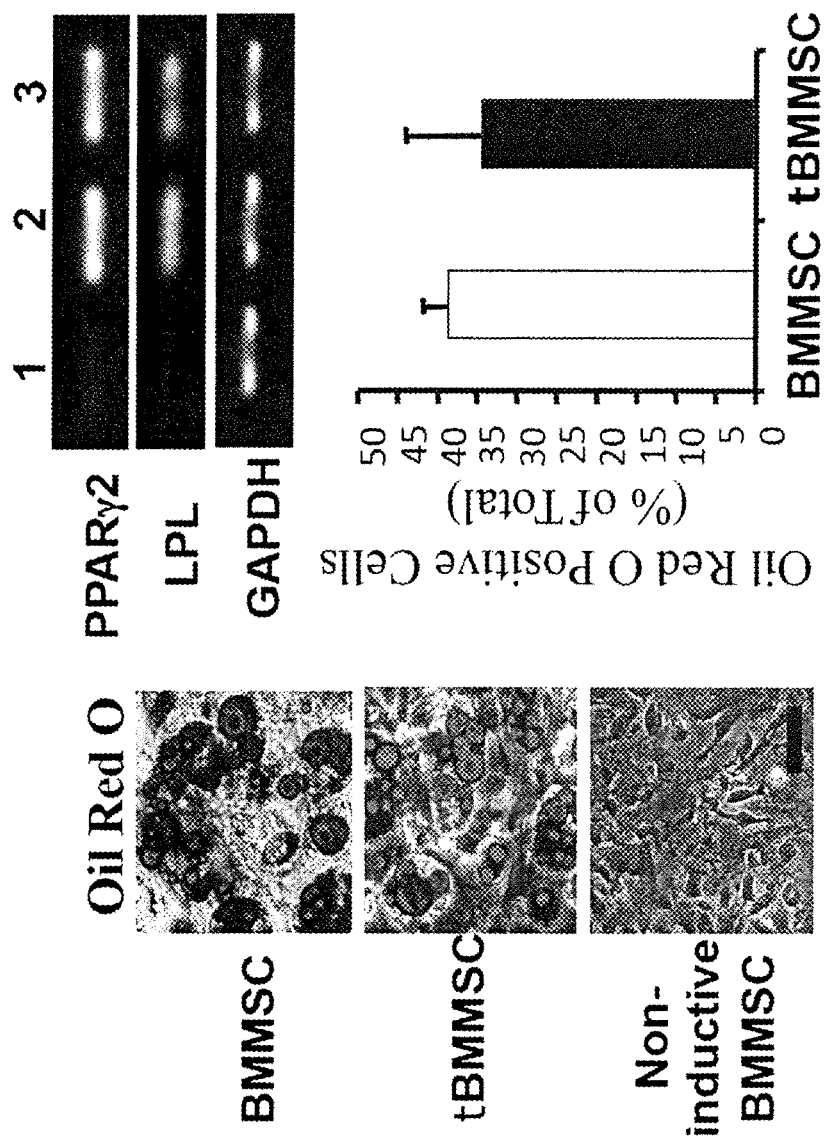
Figure 11D:
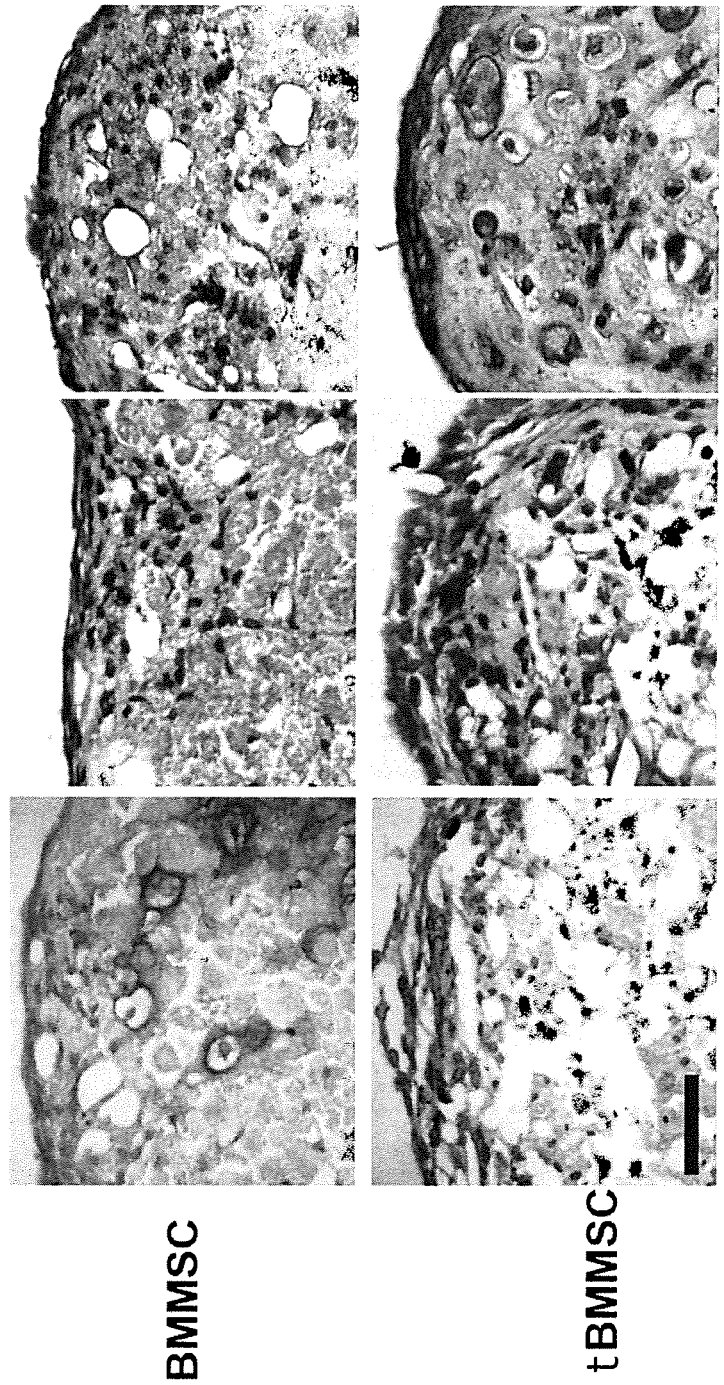

To examine the multipotent differentiation potential, we revealed that tBMMSCs are analogous to BMMSCs in expression of alkaline phosphatase (ALP), mineralized nodule accumulation under the osteogenic inductive cultures, and bone regeneration when transplanted into immunocompromised mice using HA/TCP as a carrier (FIGS. 11A, 11B). Furthermore, we showed that tBMMSCs were similar to regular BMMSCs in forming Oil red O positive cells under adipogenic inductive conditions, expression of adipogenic genes peroxisome proliferator-activated receptor gamma 2 (PPARγ2) and lipoprotein lipase (LPL), and differentiating into chondrocytes under the chondrogenic inductive conditions with expression of proteoglycan, trichrome positive collagen, and type II collagen (FIGS. 11C, 11D). These data confirm that tBMMSCs are a novel subset of non-adherent BMMSCs.

Figure 2A:
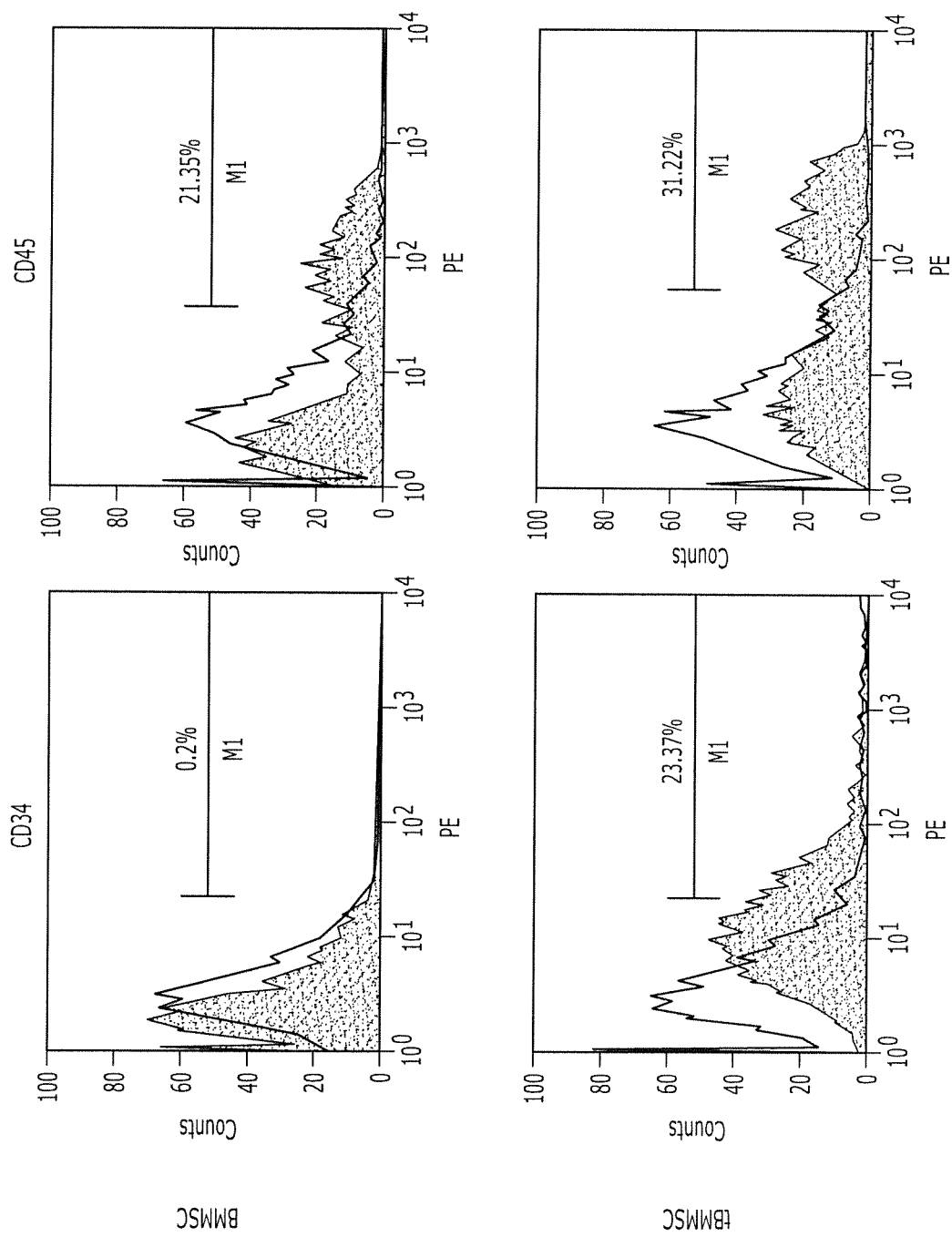
FIGS. 2A-2F show that tBMMSCs express CD34 and possess high telomerase activity.
Figure 2B:
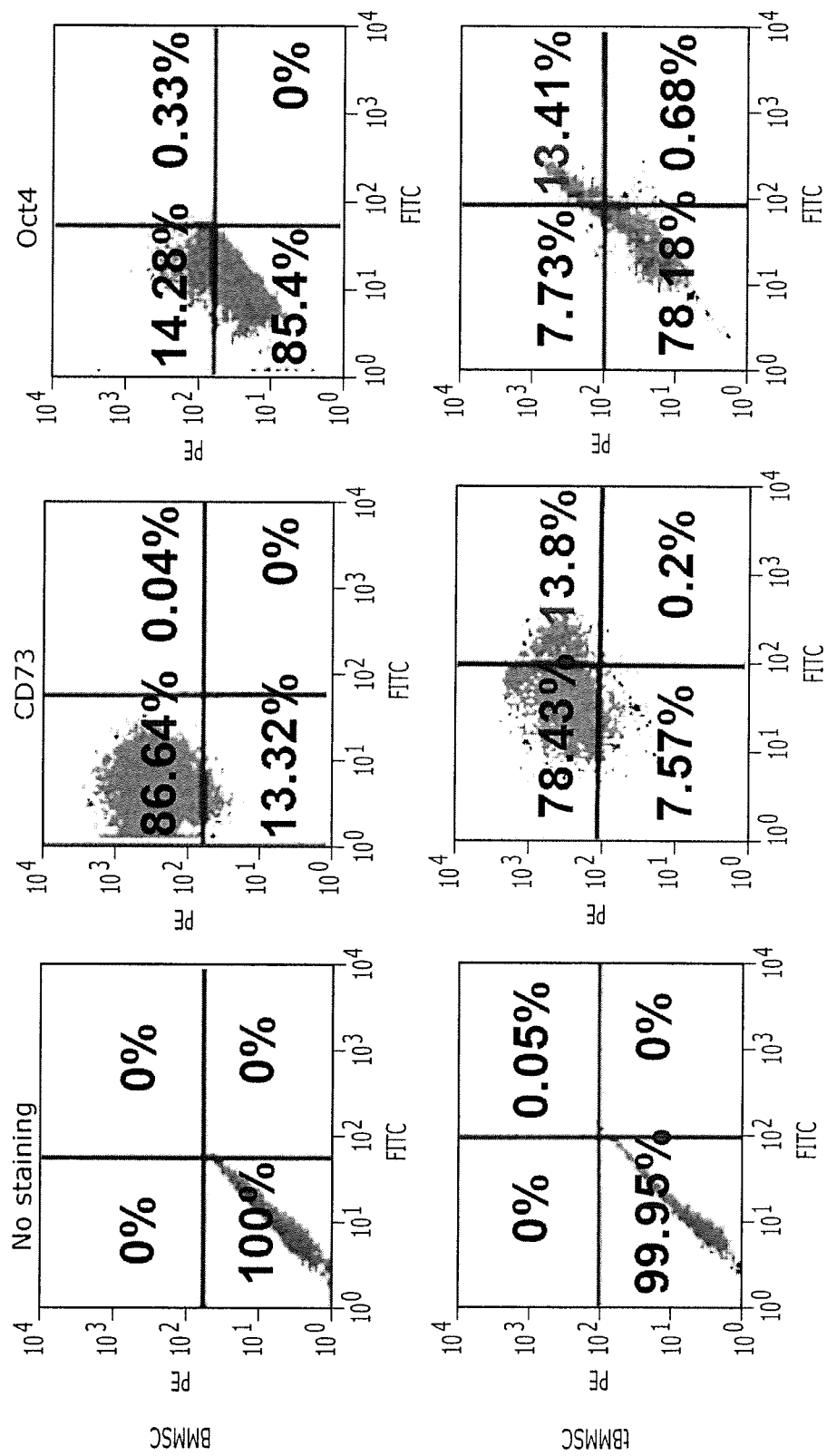
Figures 2C, 2D:
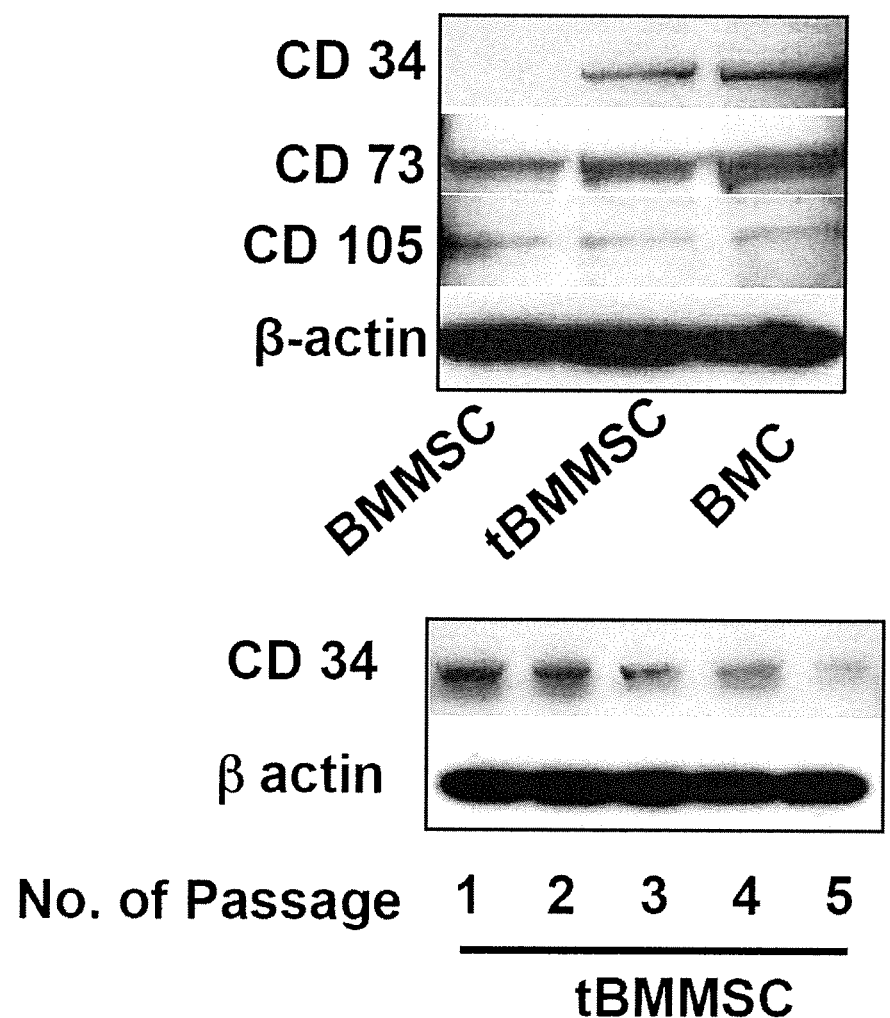
Figure 2F:
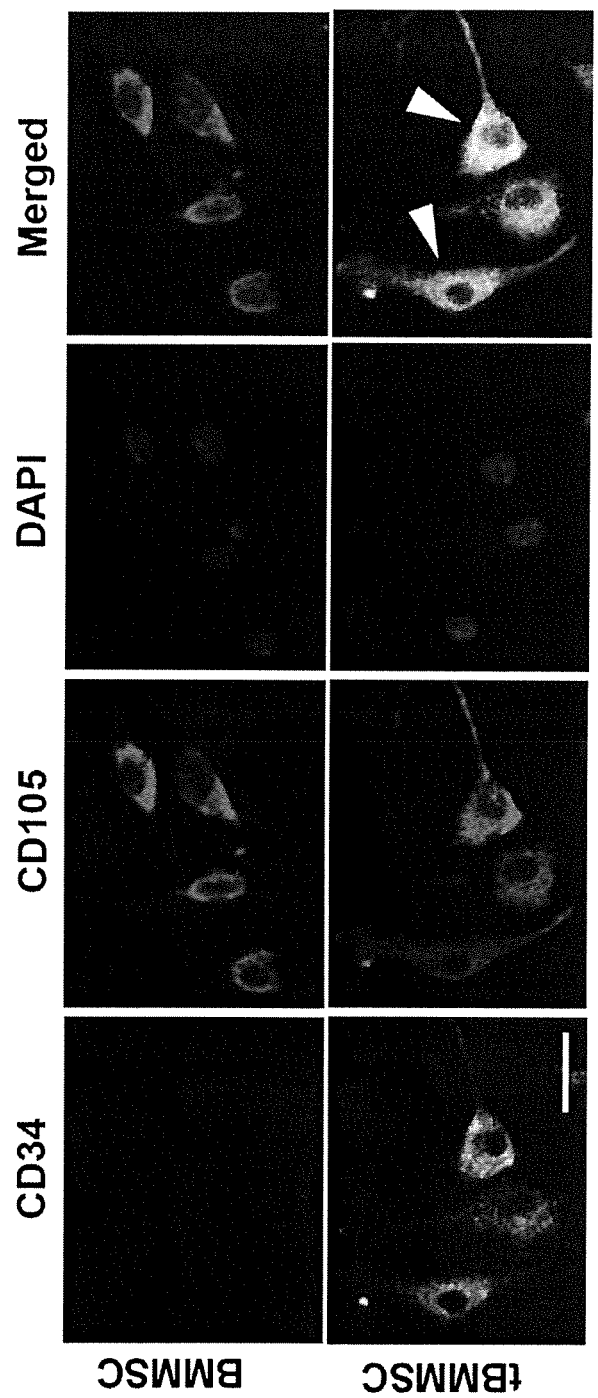
Figure 2G:
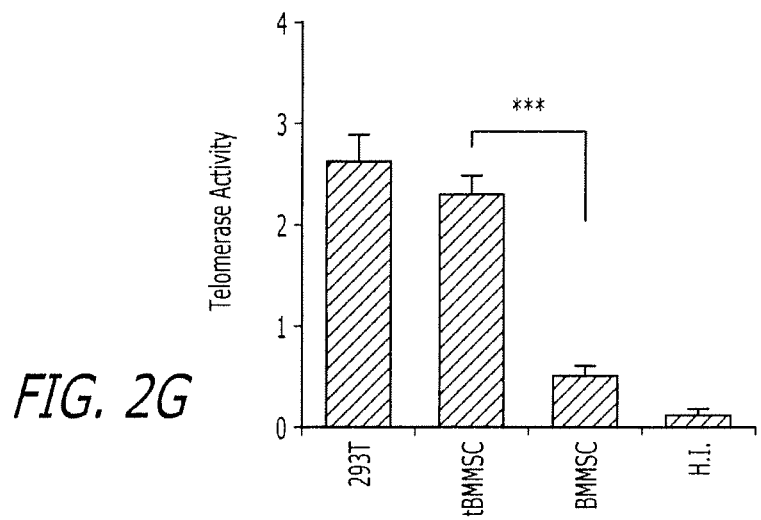
(FIG. 2H) Western blot verifies that tBMMSCs express telomerase reverse transcriptase (TERT) and BMMSCs are negative for anti TERT antibody staining.
(FIG. 2I) There are 3.77% cells are double positive for anti CD34 and CD73 antibody staining in whole bone marrow ANCs, these CD34+/CD73+ cells can be sorted out from bone marrow using flow cytometric sorter.
(FIG. 2J) CD34+/CD73+ cells form CFU-F on BMMSC-ECM cultures at frequency similar to tBMMSCs.
(FIG. 2K) CD34+/CD73+ BMMSCs show higher telomerase activity than regular BMMSCs. HEK293T cells were used as positive control (293T) and heat inactive HEK293T cells were used as negative control (H.I.) measured by a Telo TAGGG Telomerase PCR ELISA kit.
(FIG. 2L) CD34$^+$/CD73$^+$ BMMSCs also show a significant NO production when compared to regular BMMSCs. The results were representative of five independent experiments. Scale bars=50 μm. ***P<0.001. The graph bar represents mean±SD.
Figure 2H:
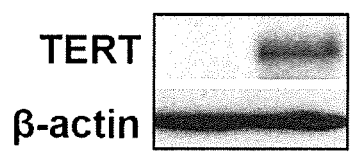

Example 2 tBMMSCs Express Telomerase and CD34, but are Distinct From Hematopoietic Stem Cells In order to characterize tBMMSCs, flow cytometric analysis was used to examine whether tBMMSC expressed hematopoietic cell markers. We found that 17.4% of tBMMSCs, but not regular BMMSCs, expressed CD34, a HSC and endothelial cell marker (FIG. 2A). BMMSCs (21.25%) and tBMMSCs (31.22%) expressed CD45, another hematopoietic marker, at passage 2 (FIG. 2A). Both BMMSCs and tBMMSCs were negative to CD11b antibody staining (data not shown), excluding that tBMMSCs are derived from monocyte/macrophage lineage cells. Importantly, CD34$^+$ tBMMSCs co-expressed BMMSC associated markers (CD73 or Oct4), as evidenced by flow cytometric analysis (FIG. 2B). Western blot analysis confirmed that tBMMSCs expressed CD34, CD73, and CD105 (FIG. 2C), and regular BMMSCs expressed CD73 and CD105, but lacked expression of CD34 (FIG. 2C). tBMMSCs show a continued expression of CD34 from passage 1 to 5, however, the expression levels appear reduced after passage 3 (FIG. 2D). To further verify CD34 expression in tBMMSCs, we used double immunocytostaining to show that tBMMSCs co-express CD34 with mesenchymal markers CD73 and CD105 (FIGS. 2E, 2F) and regular BMMSCs are negative for anti-CD34 antibody staining (FIGS. 2E, 2F). More interestingly, we found that tBMMSCs possessed significantly higher levels of telomerase activity compared to regular BMMSCs by PCR-ELISA assay and Western blot analysis (FIGS. 2G, 2H), implicating that tBMMSCs may be a primitive subpopulation of BMMSCs.

Figure 2I:
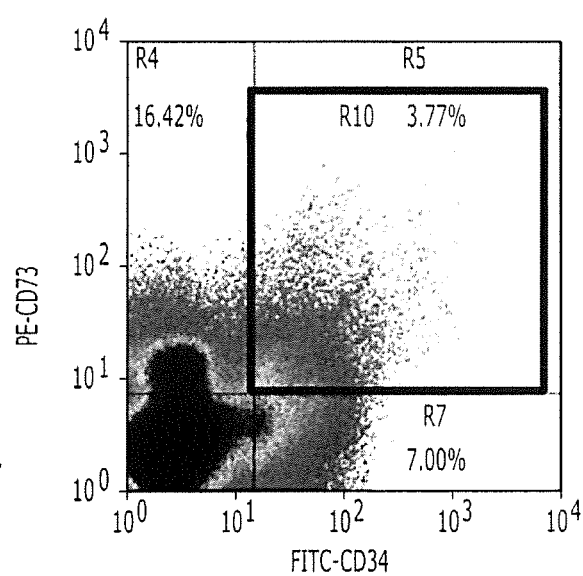
Figure 2J:
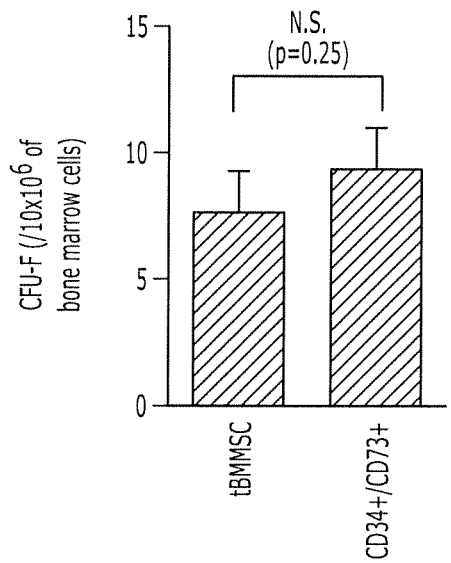
Figure 2K:
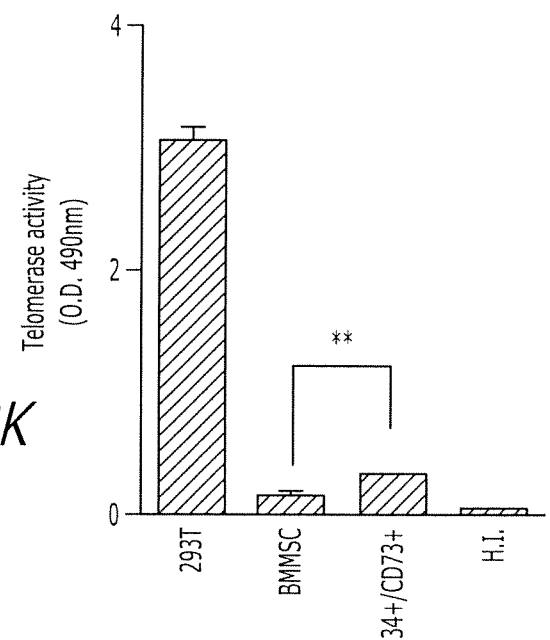
Figure 2L:
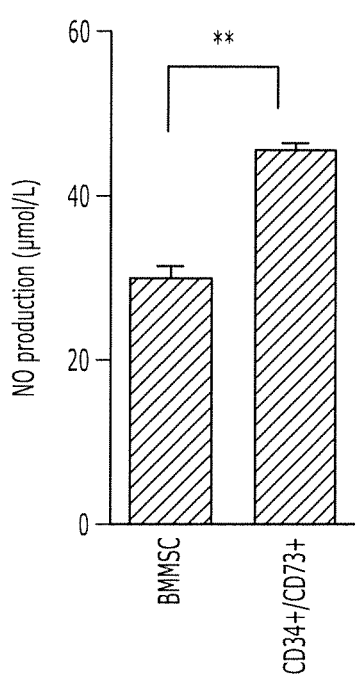

Next, we used flow cytometry to sort CD34 and CD73 double-positive cells from bone marrow ANCs and recovered 3.77% double-positive cells (FIG. 2I). These CD34 and CD73 double-positive cells exhibit mesenchymal stem cell characteristics, including forming single colony clusters (FIG. 2J) and differentiating into osteogenic and adipogenic cells (data not shown), indicating a feasible approach of directly isolating tBMMSC-like cells from bone marrow. CD34$^+$/CD73$^+$ BMMSCs are analogous to tBMMSCs in terms of having higher level of telomerase activity and high NO production when compared to regular BMMSCs (FIGS. 2K, 2L).

Figure 3A:
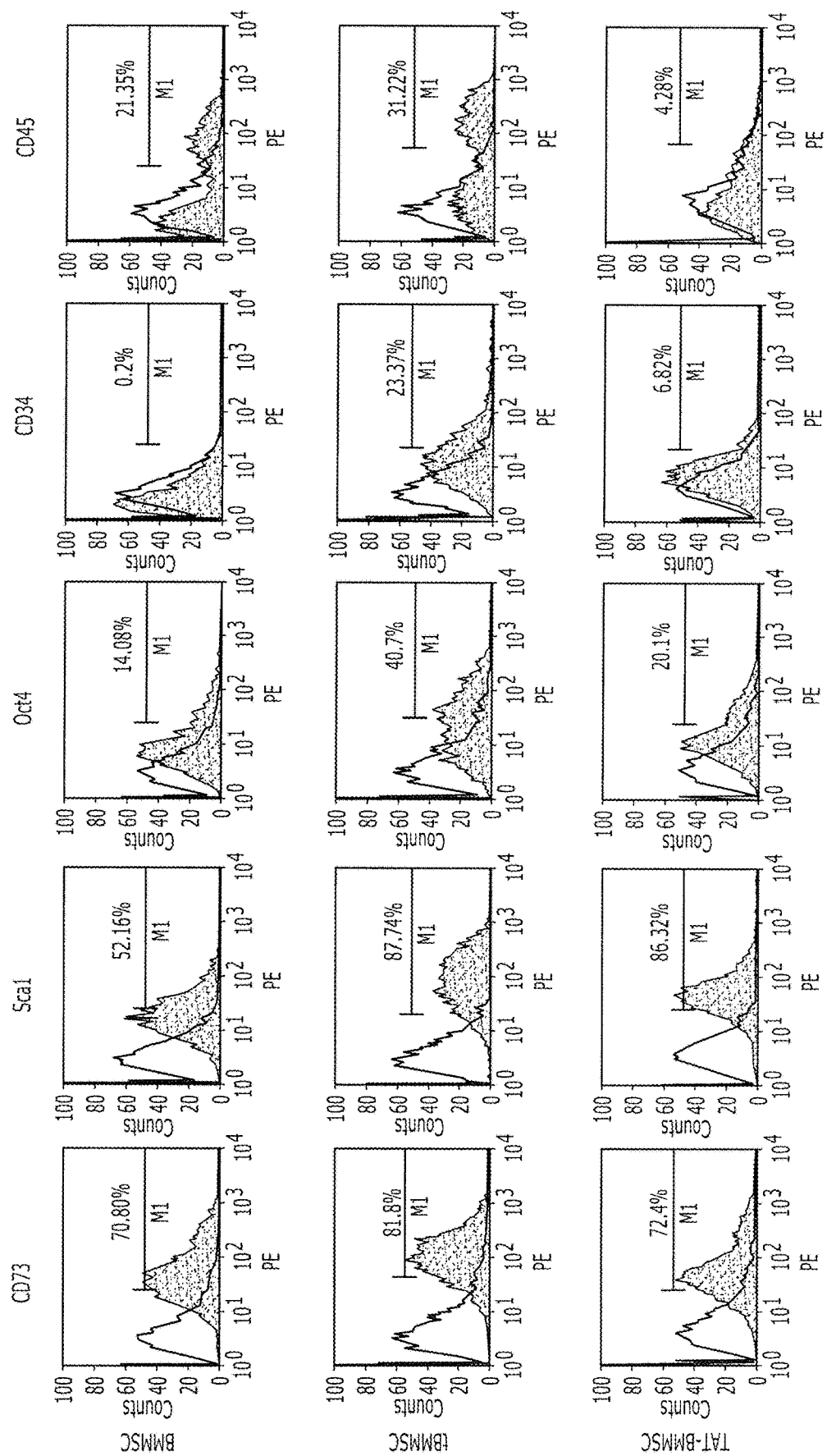
FIGS. 3A-C show that aspirin treatment elevates CD34 expression in BMMSCs.
Figure 3B:
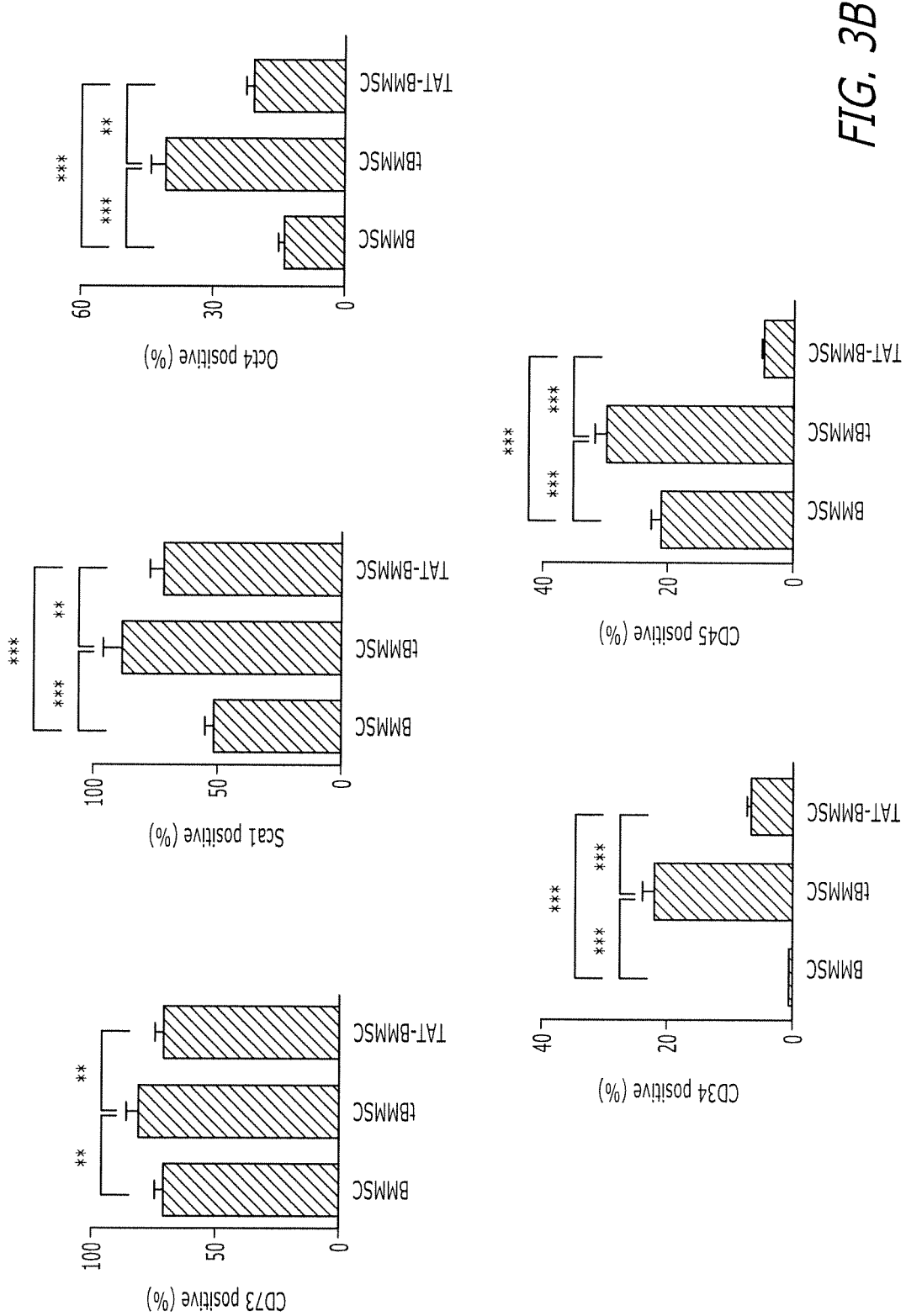
Figure 3C:
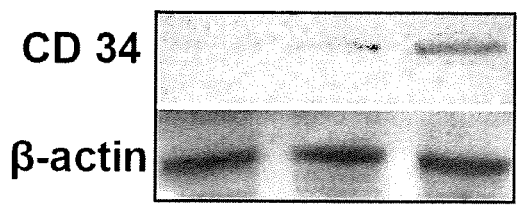
Figure 7A:
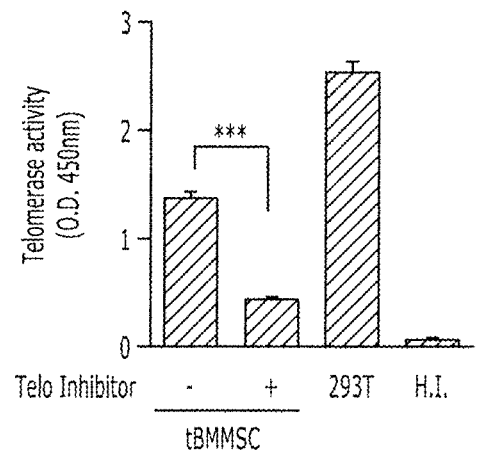
FIGS. 7A-L show that Nitric oxide production by BMMSCs is governed by telomerase and Wnt/beta-catenin signaling.
Figure 7B:
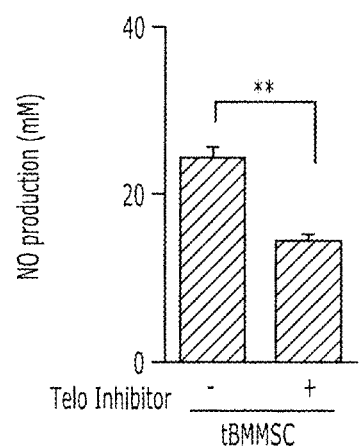
Figure 7C:
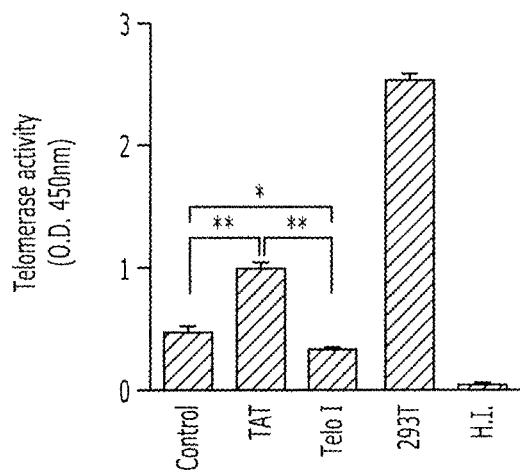

To exclude potential HSC contamination in tBMMSCs, we used aspirin (TAT) to elevate telomerase level in regular CD34$^-$ BMMSCs (FIG. 7C). After the aspirin treatment, BMMSCs exhibit higher levels of Sca-1 and Oct4 expression when compared to BMMSCs, but at a lower level than tBMMSCs (FIG. 3A, 3B). Importantly, aspirin (TAT)-treated CD34$^-$ BMMSCs acquire a positive CD34 expression (FIG. 3A). Western blot analysis confirmed that aspirin (TAT)-treated BMMSCs express CD34, but at a lower level than tBMMSCs (FIG. 3C). These data suggest that CD34 expression in BMMSCs is not due to HSC contamination.

Figure 4A:
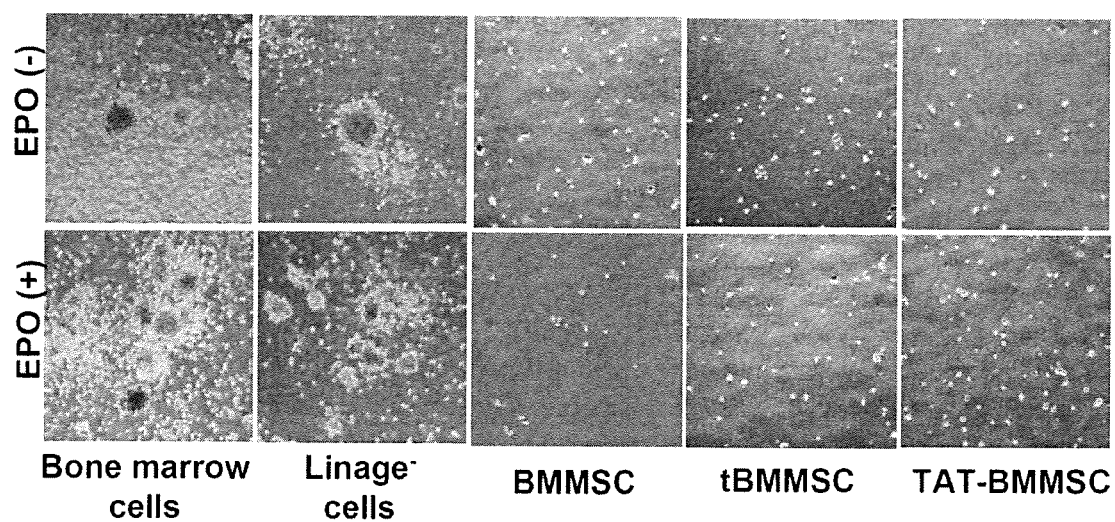
FIGS. 4A-B shows Hematopoietic differentiation of tBMMSCs.
Figure 4B:
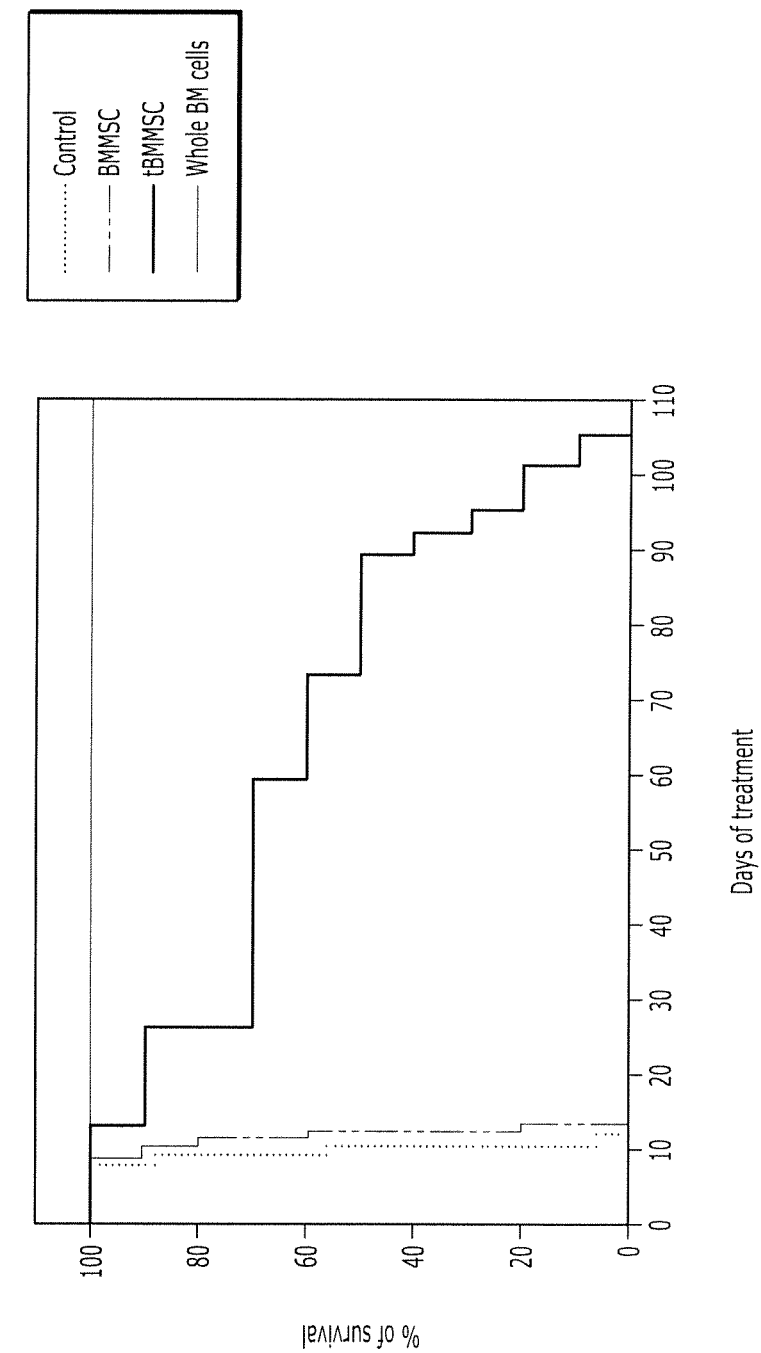

It is generally believed that CD34 expression is associated with HSCs and endothelial populations. HSCs can differentiate into hematopoietic cell lineage and rescue lethal dose-irradiated subjects. Thus, we use hematopoietic differentiation medium to treat tBMMSCs, aspirin (TAT)-treated BMMSCs and regular BMMSCs and find all of these cells fail to differentiate into hematopoietic cell lineage as seen in bone marrow cells and linage cells served as positive controls capable of forming colony clusters (FIG. 4A). Next, we infused tBMMSC systemically to rescue lethal dose-irradiated mice and found that tBMMSCs, but not regular BMMSCs, can extend the lifespan of lethal dose-irradiated mice (FIG. 4B). However, tBMMSCs failed to rescue lethal dose-irradiated mice, as shown in bone marrow group (FIG. 4B). These experimental evidences further indicate that CD34 expression in tBMMSCs is not due to HSC contamination.

Figure 5A:
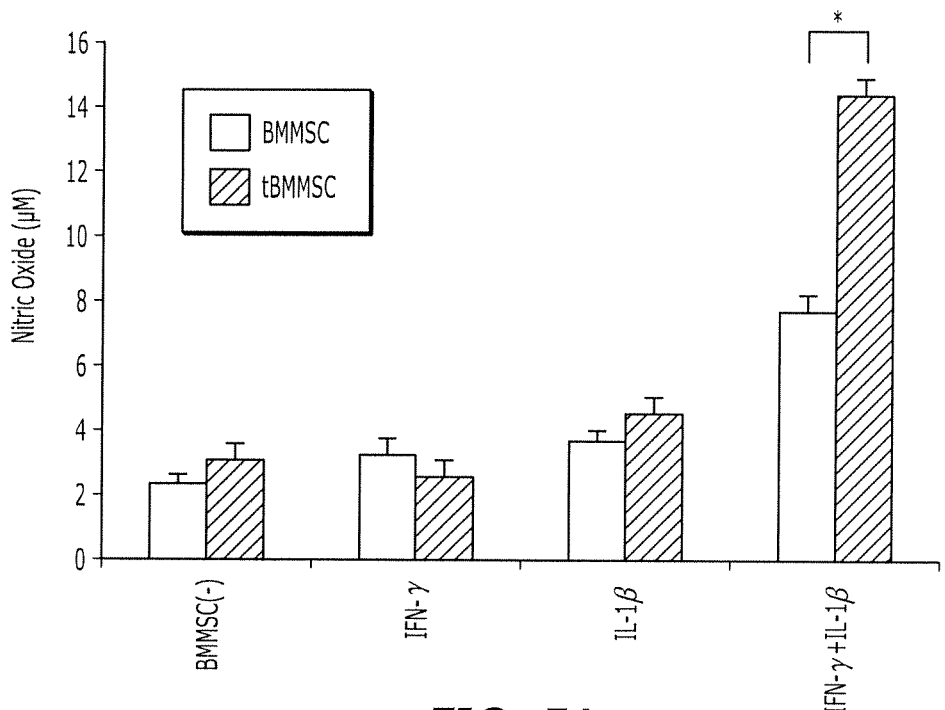
FIGS. 5A-5M show that tBMMSCs show up-regulated immunomodulatory properties.
Figure 5B:
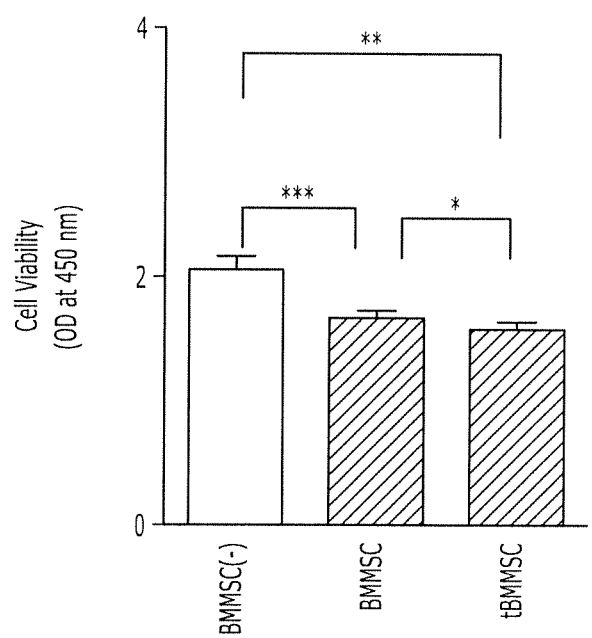
Figure 5C:
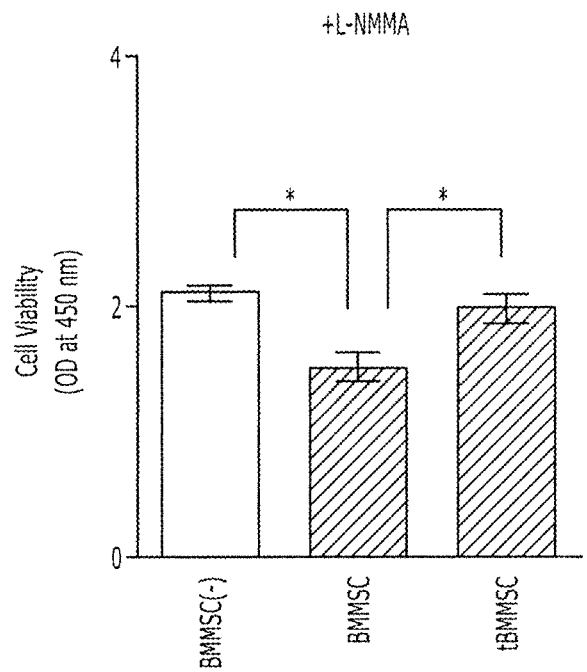
Figure 5D:
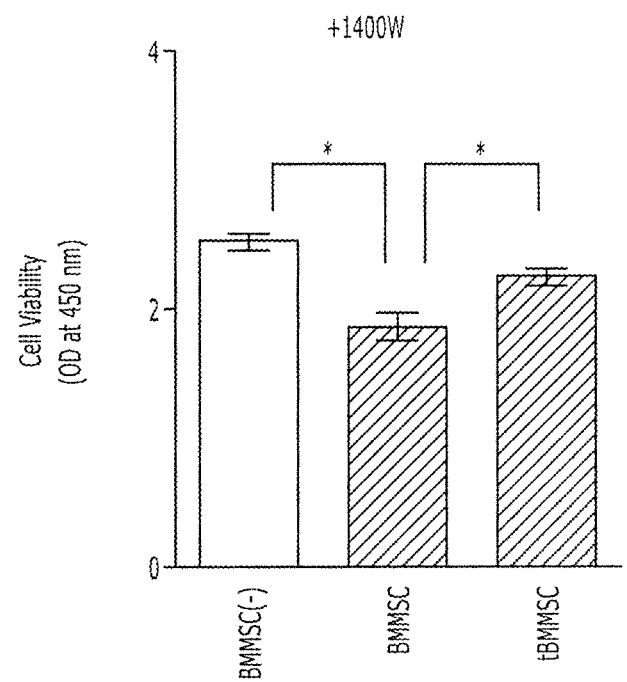
Figure 5E:
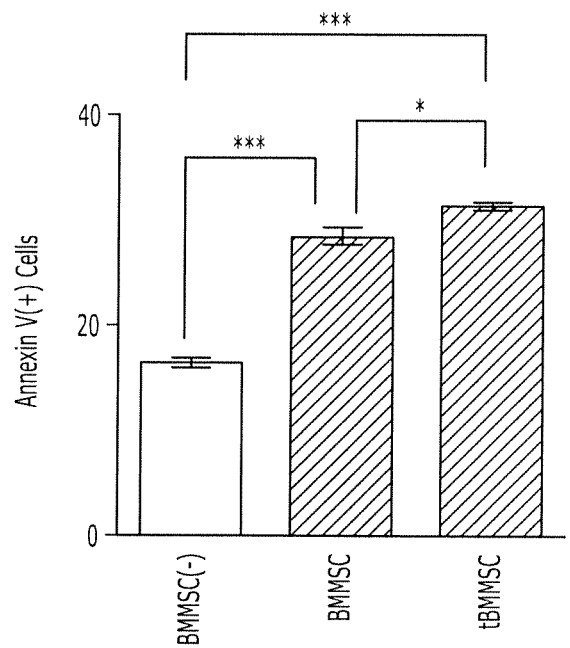
Figure 5F:
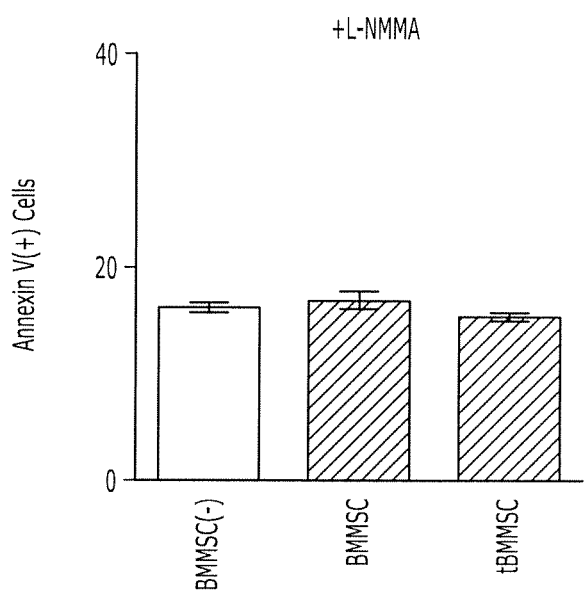
Figure 5G:
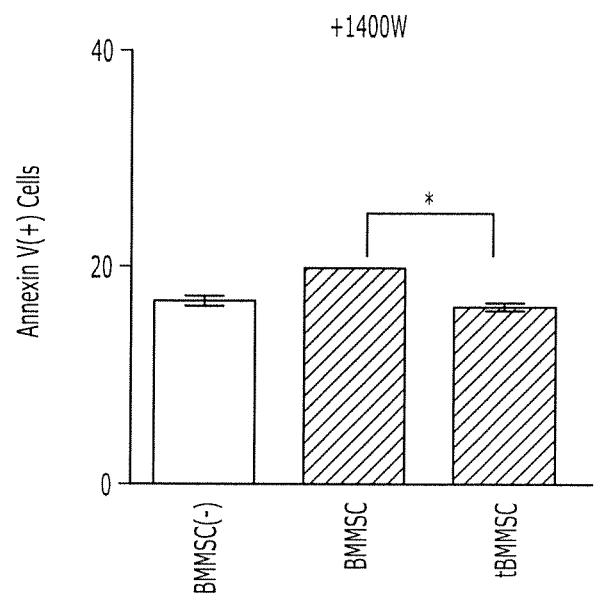
Figure 5H:
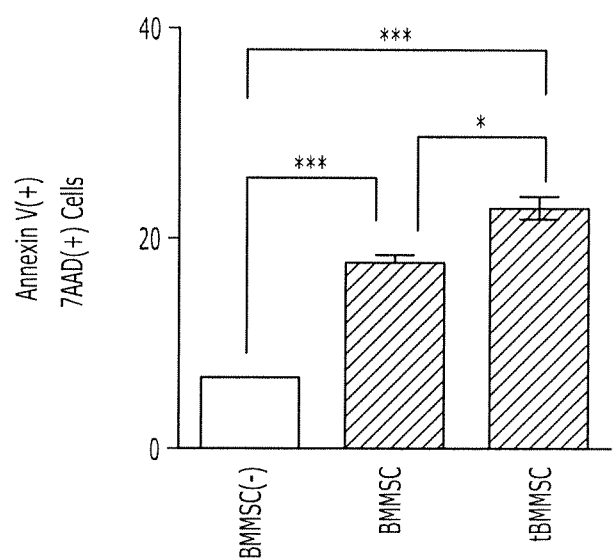
Figure 5I:
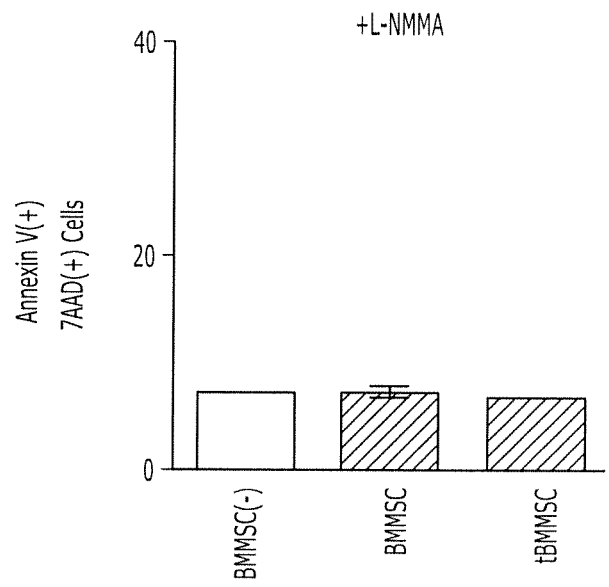
Figure 5J:
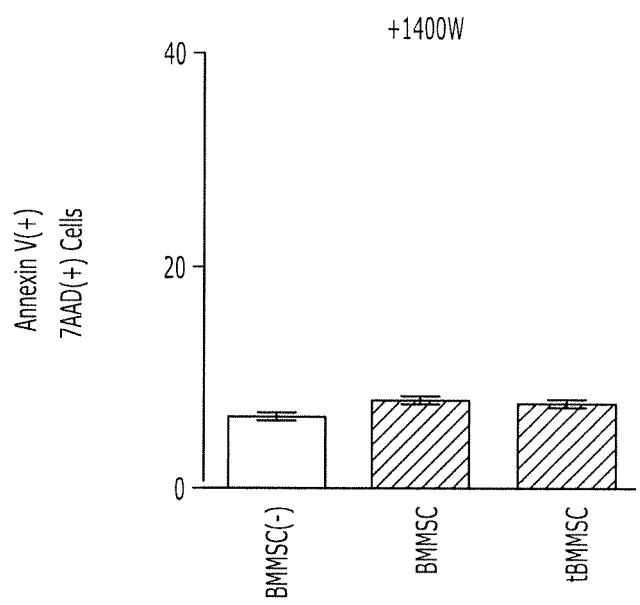
Figure 12A:
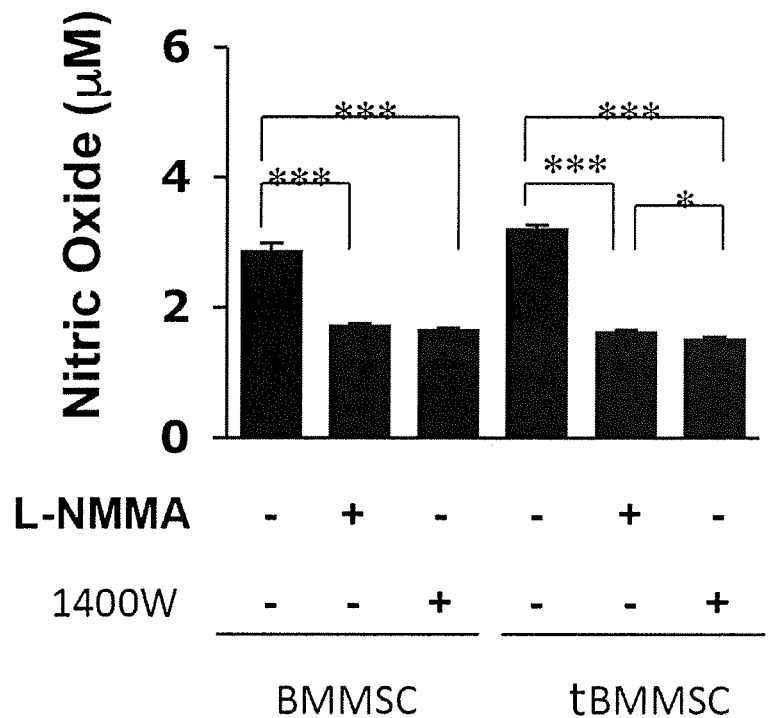
FIGS. 12A-B show the NO level in tBMMSCs. BMMSCs and tBMMSCs (2×105/well) were cultured for 3 days and treated with L-NMMA (1 mM) or 1400W (0.2 mM) for 3 days.
Figure 12B:
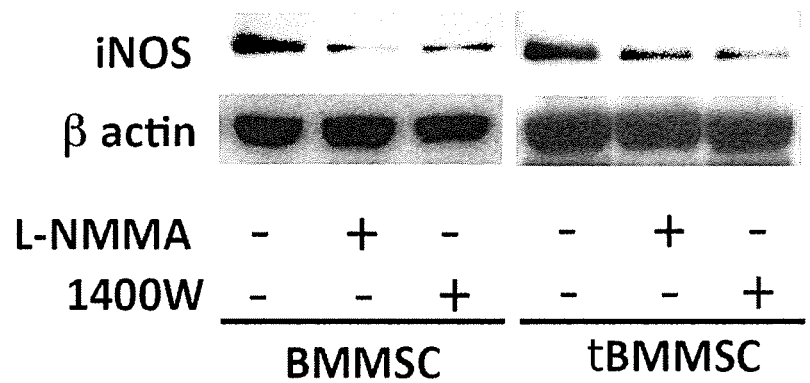

Example 3 tBMMSCs Posses Superior Immunomodulatory Functions Via High Nitric Oxide (NO) Production Recently, immunomodulatory properties were identified as an important stem cell characteristic of BMMSCs, leading to utilize systemic infused BMMSCs to treat a variety of immune diseases (Nauta et al., 2007; Uccelli et al., 2007, 2008). Here we found that tBMMSCs exhibited a significant increased capacity for NO production compared to regular BMMSCs when treated with interferon gamma (IFNγ) and interleukin 1 beta (IL-1β) (FIG. 5A). It is known that NO plays a critical role in BMMSC-mediated immunosuppression (Ren et al., 2008), therefore, we assessed the functional role of high NO production in tBMMSC-associated immunomodulatory properties. Spleen (SP) cells were activated with stimulation of anti-CD3 and anti-CD28 antibodies for 3 days and then co-cultured with tBMMSCs or regular BMMSCs in the presence of the general nitric oxide synthase (NOS) inhibitor, NG-monomethyl-L-arginine (L-NMMA), or the inducible NOS (iNOS) inhibitor, 1400W, using a Transwell culture system. The efficacy of L-NMMA and 1400W to inhibit NO production in BMMSCs was verified (FIG. 12). Although both tBMMSCs and regular BMMSCs were capable of inhibiting cell viability of activated SP cells, tBMMSCs showed a marked inhibition of SP cell viability over that of regular BMMSCs (FIG. 5B). Interestingly, both L-NMMA and 1400W were able to significantly block tBMMSC, but not regular BMMSC, induced cell viability of activated SP cells (FIGS. 5C, 5D). Furthermore, flow cytometric analysis indicated that both tBMMSCs and regular BMMSCs induce apoptosis of activated SP cells in the Transwell culture system, including early apoptotic cells (FIG. 5E) and late apoptotic and dead cells (FIG. 5H). However, tBMMSCs show an elevated capacity in inducing activated SP cell apoptosis compared to regular BMMSCs (FIGS. 5E, 5H). When L-NMMA and 1400W were added to the cultures, the number of early and late apoptotic SP cells was significantly reduced in both tBMMSC and regular BMMSC groups (FIGS. 5F, 5G, 5I, 5J). Treatment with 1400W resulted in a significantly greater inhibition of early apoptotic SP cells in tBMMSC group compared to the regular BMMSC group (FIG. 5G). These data suggest that NO production is required for BMMSC-mediated immunomodulation.

Figure 5K:
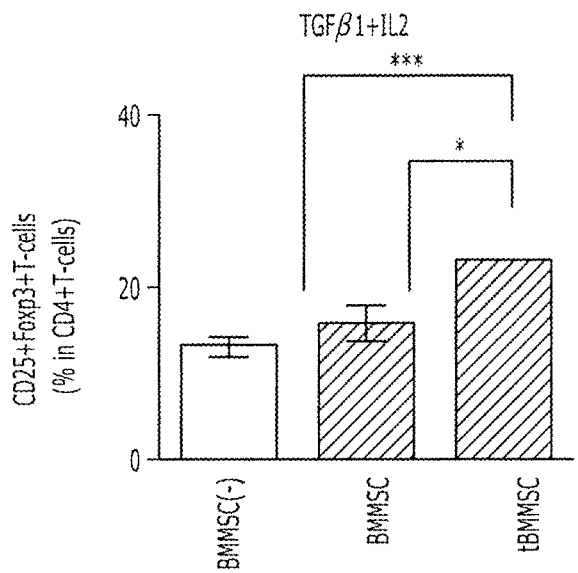
Figure 5L:
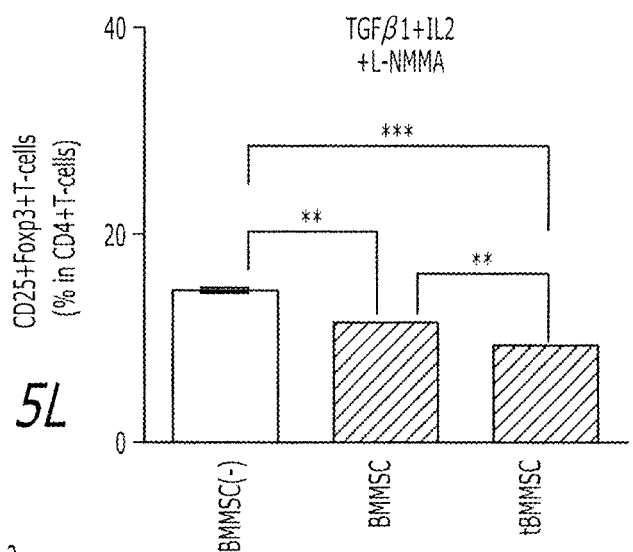
Figure 5M:
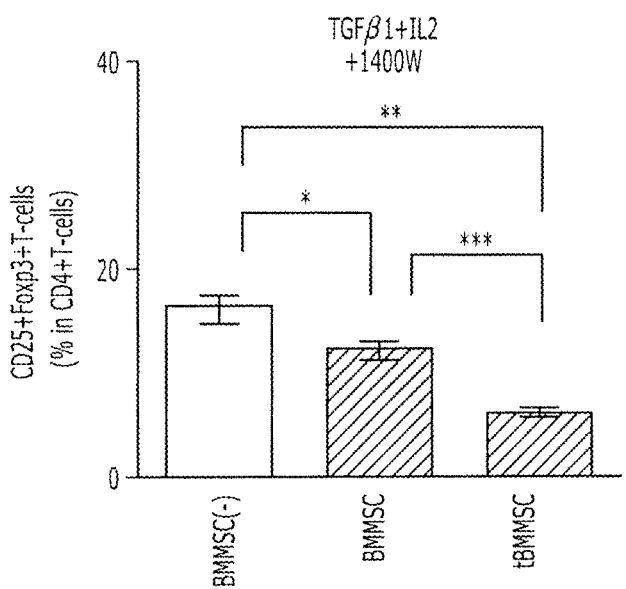

Next, we co-cultured naïve$^-$T-cells with tBMMSCs or regular BMMSCs in the presence of IL-2 and transforming growth factor beta 1 (TGF-β1). We found that tBMMSCs showed a significant up-regulation of CD4$^+$CD25$^+$Foxp3$^+$ regulatory T cell (Tregs) levels when compared to regular BMMSCs (FIG. 5K). Both L-NMMA and 1400W were able to inhibit BMMSC- and tBMMSC-induced up-regulation of Tregs, as shown by flow cytometric analysis (FIGS. 5L, 5M). The regulatory effect on Tregs was more significant in the tBMMSC group compared to the BMMSC group (FIGS. 5L, 5M). These data further verified the role of NO in tBMMSC-induced immunomodulatory effect.

Example 4 tBMMSCs Transplantation Improves Multiple Organ Function in MRL/LPR Mice

Figure 6A:
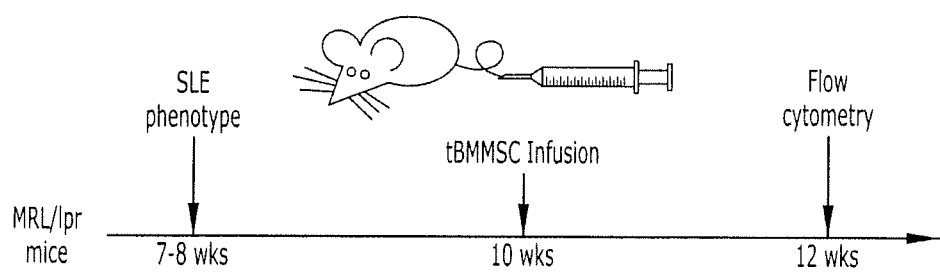
FIGS. 6A-6I show that tBMMSCs showed superior therapeutic effect on SLE-like MRL/lpr mice.
Figure 6B:
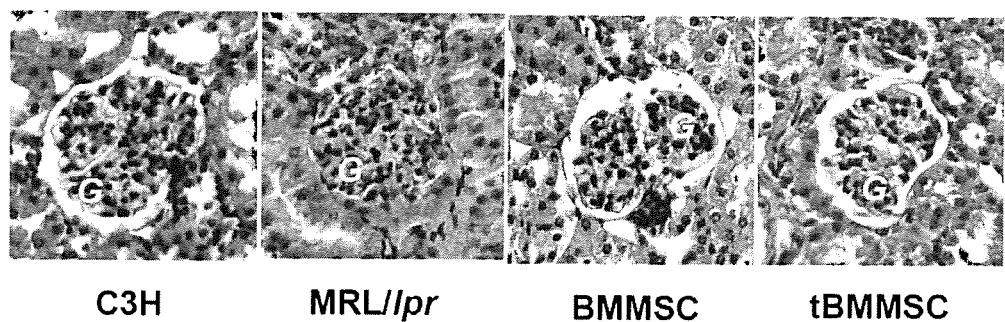
Figure 6C:
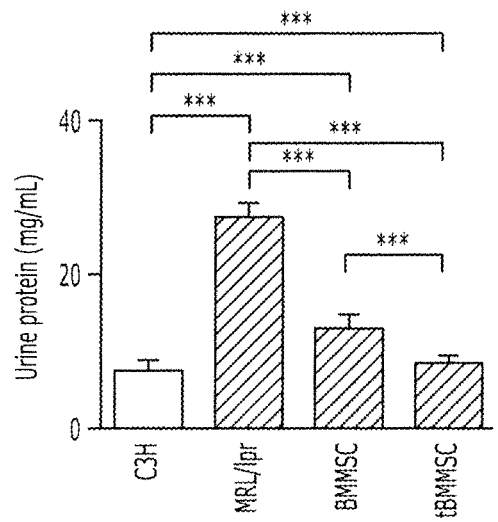
Figure 6D:
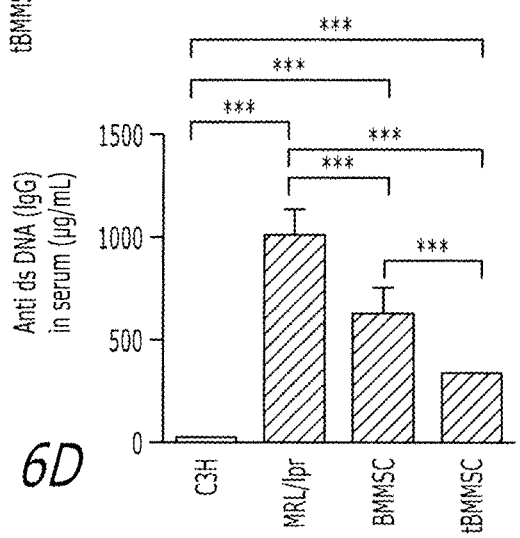
Figure 6E:
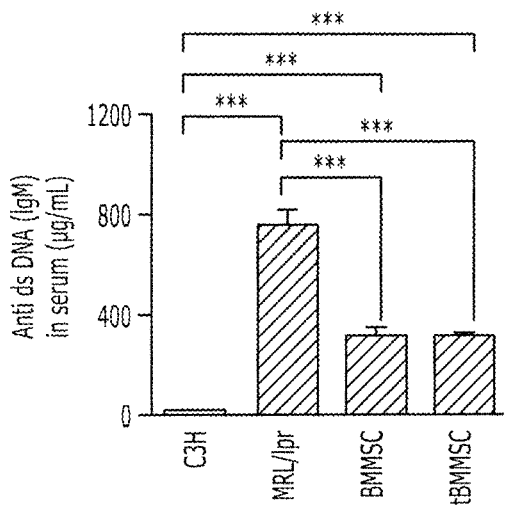
Figure 6F:
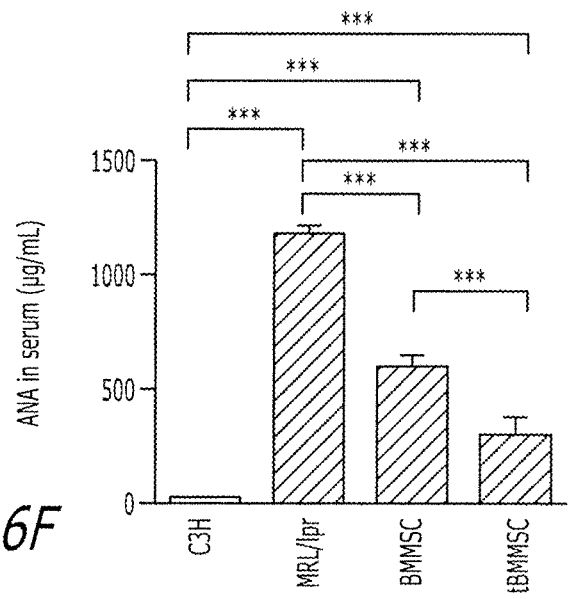
Figure 6G:
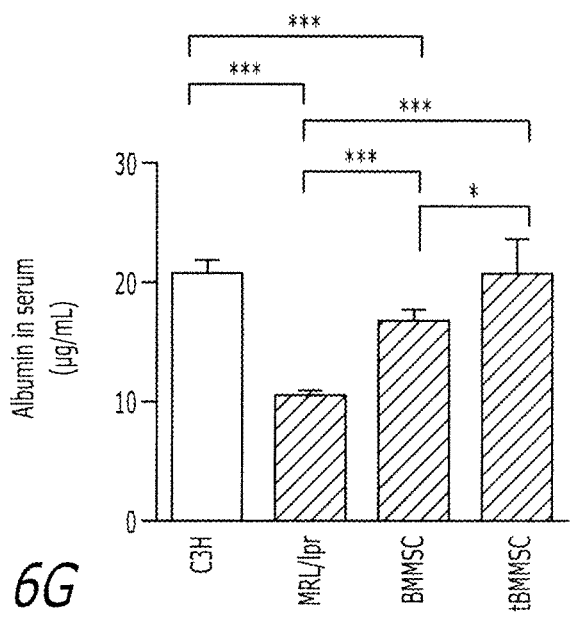

In order to examine in vivo immunomodulatory properties of tBMMSCs, we infused allogenic tBMMSCs and BMMSCs into MRL/lpr mice at 10 weeks of age and analyzed treatment response at 12 weeks of age (FIG. 6A). We found that both tBMMSCs and BMMSCs were capable of improving SLE-induced glomerular basal membrane disorder (FIG. 6B) and reducing the urine protein level (FIG. 6C). It appeared that tBMMSCs were superior compared to BMMSCs in terms of reducing the overall urine protein levels (FIGS. 6C). As expected, MRL/lpr mice showed remarkable increase in the levels of autoantibodies, including anti-double strand DNA (dsDNA) IgG and IgM antibodies (FIGS. 6D, 6E), and anti-nuclear antibody (ANA; FIGS. 6F) in the peripheral blood. Although tBMMSC and BMMSC infusion showed significant decreased levels of dsDNA IgG, IgM antibodies and ANA in peripheral blood (FIGS. 6D-F), tBMMSCs showed superior therapeutic effect in reducing dsDNA IgG antibody and ANA levels when compared to BMMSC group (FIGS. 6D, 6F). Additionally, decreased serum albumin levels in MRL/lpr mice were recovered by tBMMSC and BMMSC infusion (FIG. 6G), but tBMMSC treatment results in more significant recovery than BMMSC treatment (FIG. 6G).

Figure 6H:
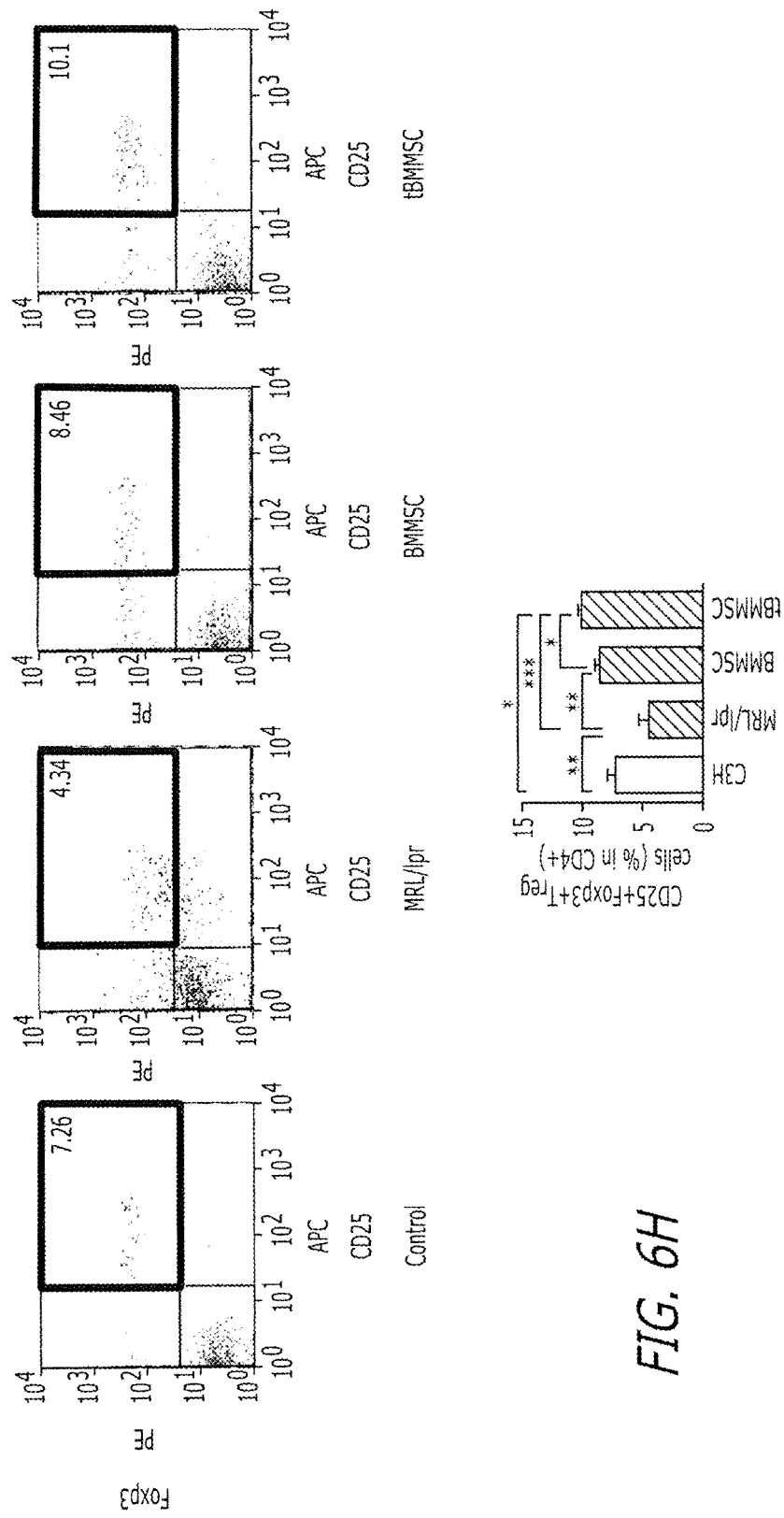
Figure 6I:
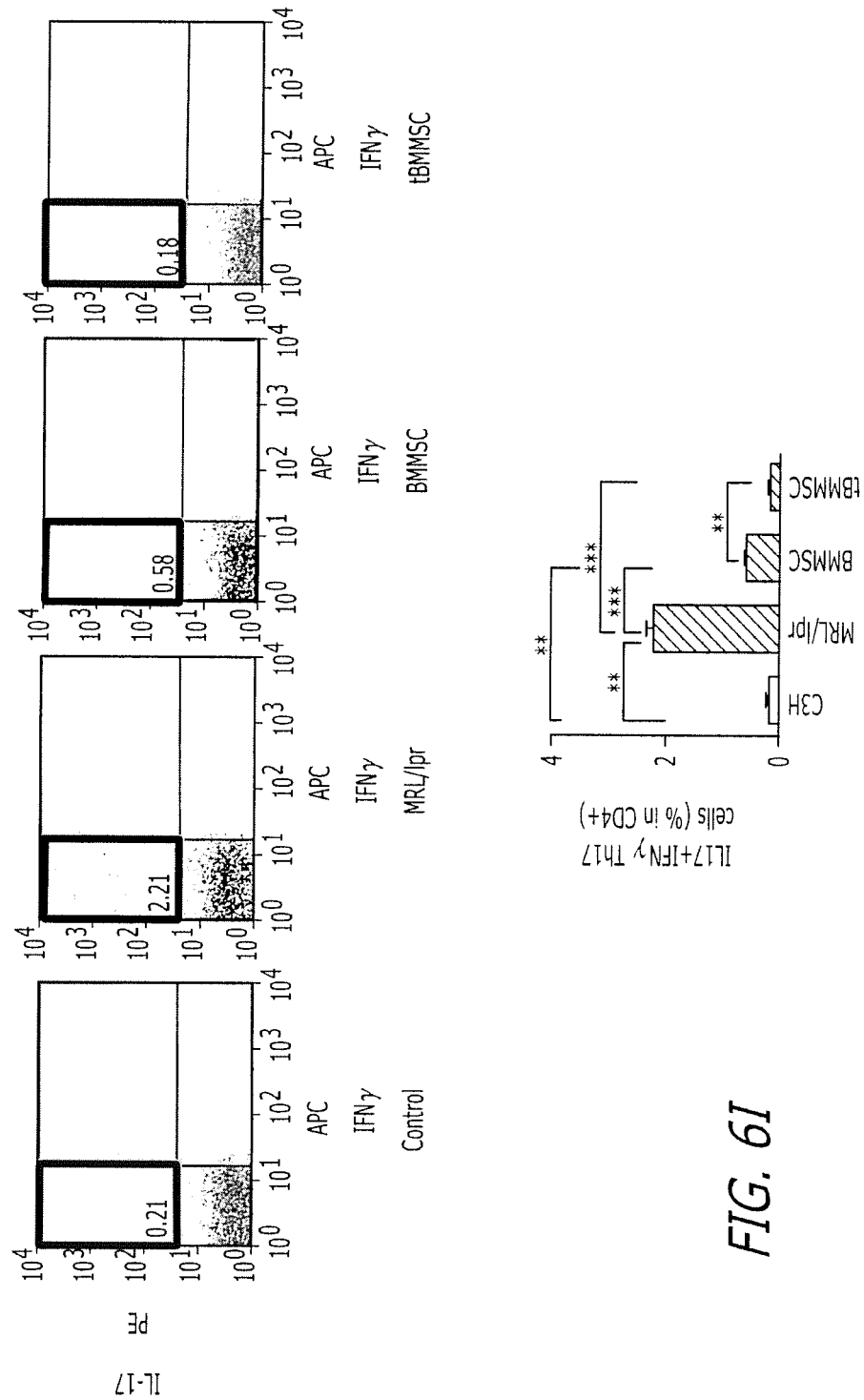
Figure 13A:
FIGS. 13A-C show the osteoclast activity in tBMMSC-treated MRL/Ipr mice.
Figure 13B:
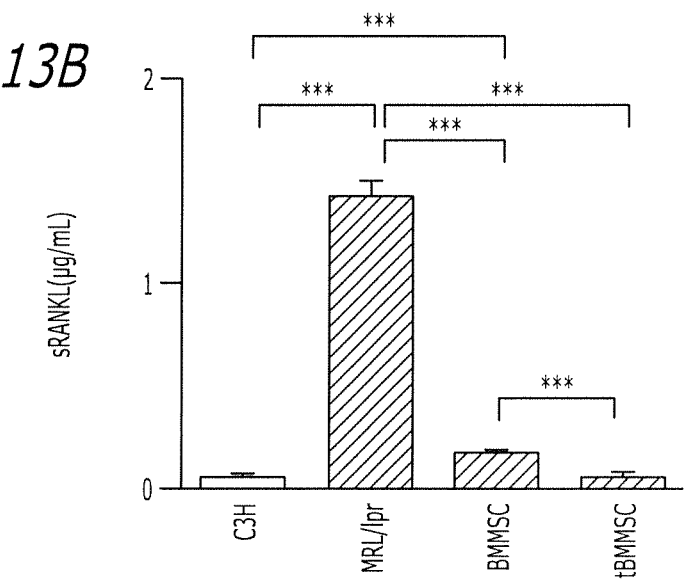
Figure 13C:
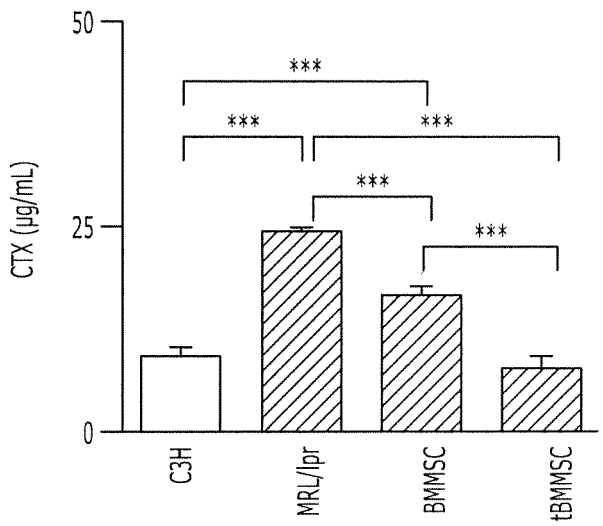

Next, we used flow cytometric analysis to reveal that tBMMSC show more effectiveness in recovering the decreased level of CD4$^+$CD25$^+$Foxp3$^+$ Tregs and increased number of CD4$^+$IL17$^+$IFNγ$^-$ T-Iymphocytes in peripheral blood when compared to BMMSCs (FIG. 6H, 6I). Furthermore, we showed that tBMMSCs are superior to BMMSCs in terms of reducing increased number of tartrate-resistant acid phosphatase (TRAP) positive osteoclasts in the distal femur epiphysis of MRL/lpr mice (FIG. 13A), elevated serum levels of soluble runt-related NF-κB ligand (sRANKL), a critical factor for osteoclastogenesis, (FIG. 13B) and bone resorption marker C-terminal telopeptides of type I collagen (CTX, FIG. 13C). These data suggest that tBMMSCs show superior therapeutic effect for SLE disorders compared to BMMSCs.

Example 5

Figure 7D:
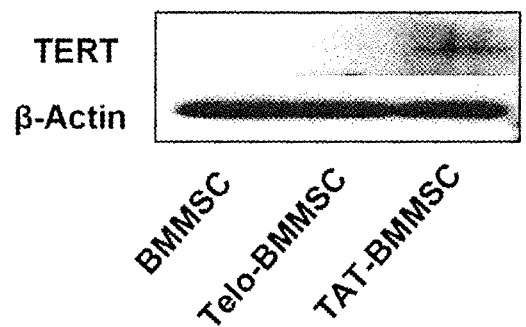
Figure 7E:
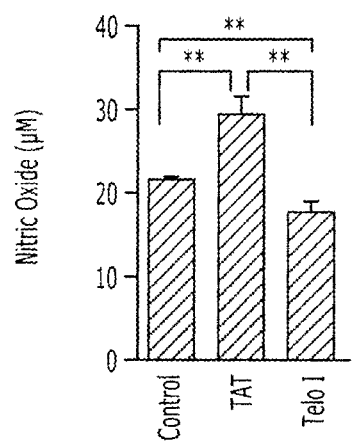

NO Production in BMMSCs is Modulated by Telomerase Activity Coupled with WNT/β-Catenin Signaling Since elevated NO production telomerase activity were observed in tBMMSCs, it is important to elucidate whether telomerase activity governs NO production in tBMMSCs. We found that telomerase inhibitor III is effective in inhibiting telomerase activity along with reducing NO production in tBMMSCs (FIGS. 7A, 7B). Similar effects of the telomerase inhibitor were also found in regular BMMSCs (FIG. 7C, 7E). In contrast, aspirin (TAT) treatment leads to a significantly elevated telomerase activity, telomerase reverse transcriptase (TERT) expression and NO production in BMMSCs (FIG. 7C-E). These data imply that telomerase activity may be associated with NO production in BMMSCs.

Figure 7F:
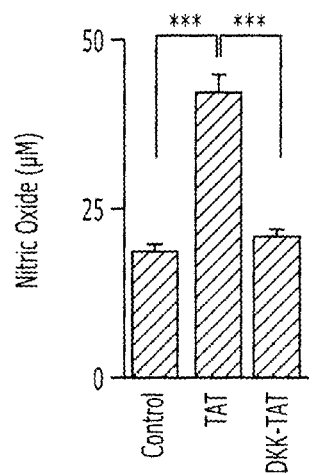
Figure 7G:
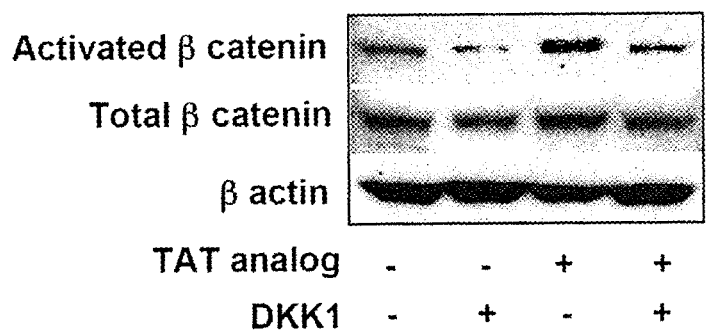
Figure 7H:
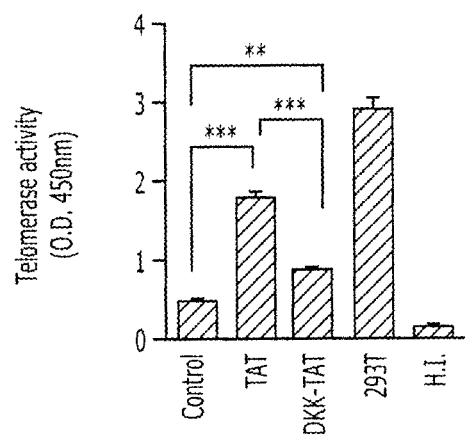

Recently, it was reported that telomerase directly modulates Wnt/beta-catenin signaling by serving as a cofactor in a beta-catenin transcriptional complex (Park et al., 2009). Thus, we assessed whether telomerase activity-associated NO production in BMMSCs could be down-regulated by the Wnt inhibitor, Dickkopf 1 (DKK1). Interestingly, we found that DKK1 was able to significantly block aspirin-induced NO production in BMMSCs when added to the cultures prior to the aspirin (TAT) treatment (FIG. 7F). The efficacy of DKK1 in reducing activated β-catenin level was confirmed by Western blot analysis (FIG. 7G). Moreover, we found that aspirin (TAT) was able to partially block DKK1-induced down-regulation of activated beta-catenin (FIG. 7G). In order to examine the mechanism by which DKK1 inhibits aspirin (TAT)-induced NO production, we showed that DKK1 is capable of blocking aspirin (TAT)-induced telomerase activity (FIG. 7H). These data indicate that telomerase-driven NO production is coupled with Wnt/β-catenin signaling.

Figure 7I:
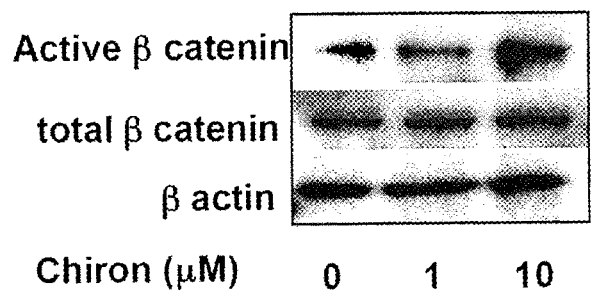
Figure 7J:
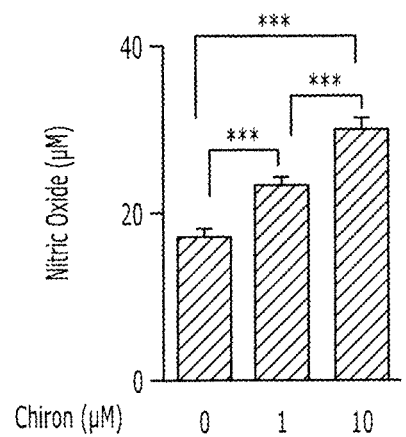
Figure 7K:
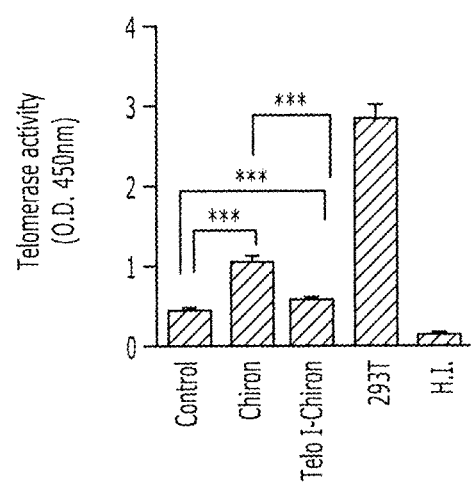
Figure 7L:
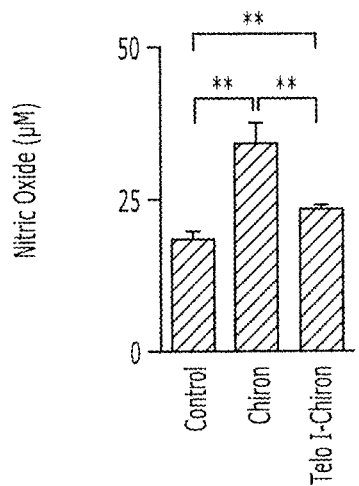

Next, we determined whether Wnt/beta-catenin signaling affected NO production in BMMSCs. We used Chiron 99021 (Chiron) to treat BMMSCs for 7 days and showed elevation of active beta-catenin in a dose-dependent manner (FIG. 7I), confirming efficacy of Chiron as a Wnt/beta-catenin activator. We then showed that Chiron treatment up-regulated NO production in BMMSCs in a dose-dependent manner (FIG. 7J), along with an elevated telomerase activity in BMMSCs (FIG. 7K). Further, we showed that Chiron-induced telomerase activity and NO production could be blocked by 3 days of pre-treatment with telomerase inhibitor III (FIGS. 7K, 7L). These findings suggest that telomerase and Wnt/beta-catenin collaboratively enhance telomerase activity and induce NO production in BMMSCs.

Example 6

Aspirin Treatment Generates Immunomodulatory Activated BMMSCs

Figure 14A:
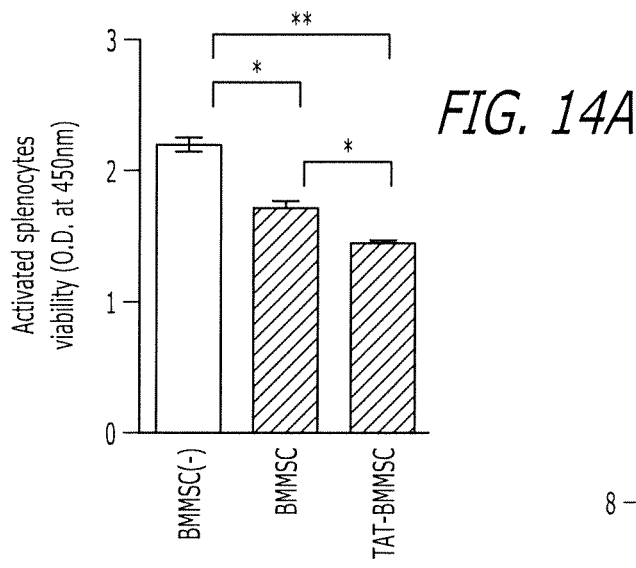
FIGS. 14A-C show that the immunomodulatory properties of BMMSCs are regulated by telomerase. SP cells (1×106/chamber), activated with anti CD3 (5 μg/mL) and CD28 (2 μg/mL) antibodies, were co-cultured with or without BMMSCs (0.2×106/chamber) using a Trans-well system (Corning) for 3 days. BMMSCs were treated with TAT analog (TAT, 3 μM) for 3 days prior to the co-culture. Cell viability of SP cells was measured using a cell counting kit-8 (Dojindo Molecular Technoloies, Gaithersburg, Md.). Apoptotic cells were stained with Annexin V-PE apoptosis detection kit I (BD Bioscience) and analyzed with FACSCalibur (BD Bioscience). TAT analog-treated BMMSCs (TAT-BMMSC) could significantly reduce activated SP cell viability (FIG. 14A) and enhance early (FIG. 14B) and late (FIG. 14C) apoptosis of activated SP cells compared to regular BMMSCs. The results were representative of five independent experiments. *P<0.05; P<0.01; *P<0.001. The graph bar represents mean±SD.
Figure 14B:
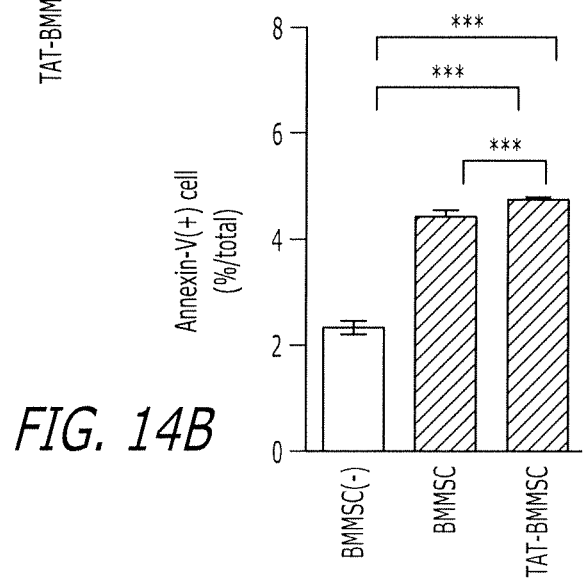
Figure 14C:
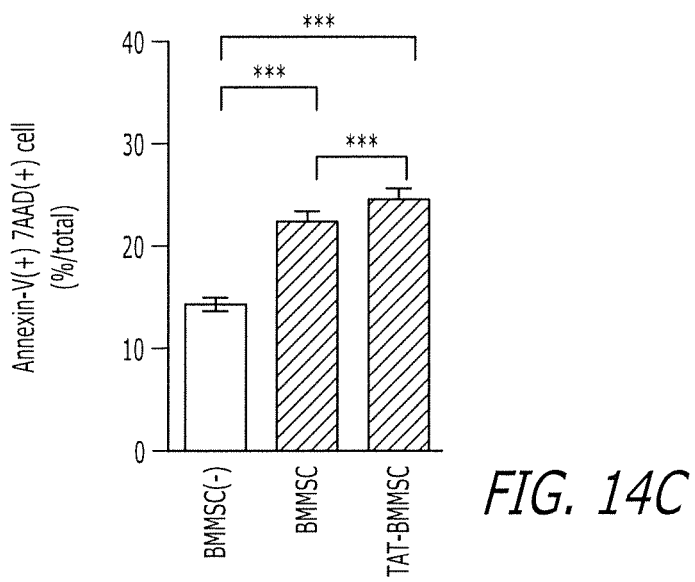

In order to determine whether telomerase affects immunomodulatory properties of regular BMMSCs, we showed that aspirin (TAT) is able to promote BMMSC-induced reduction of activated SP cell viability and elevation of early and late apoptosis of activated SP cells (FIGS. 14A-14C). These data suggest a potential of inducing telomerase activity in regular BMMSC to improve their immunomodulatory functions, as seen in tBMMSCs.

Figure 8A:
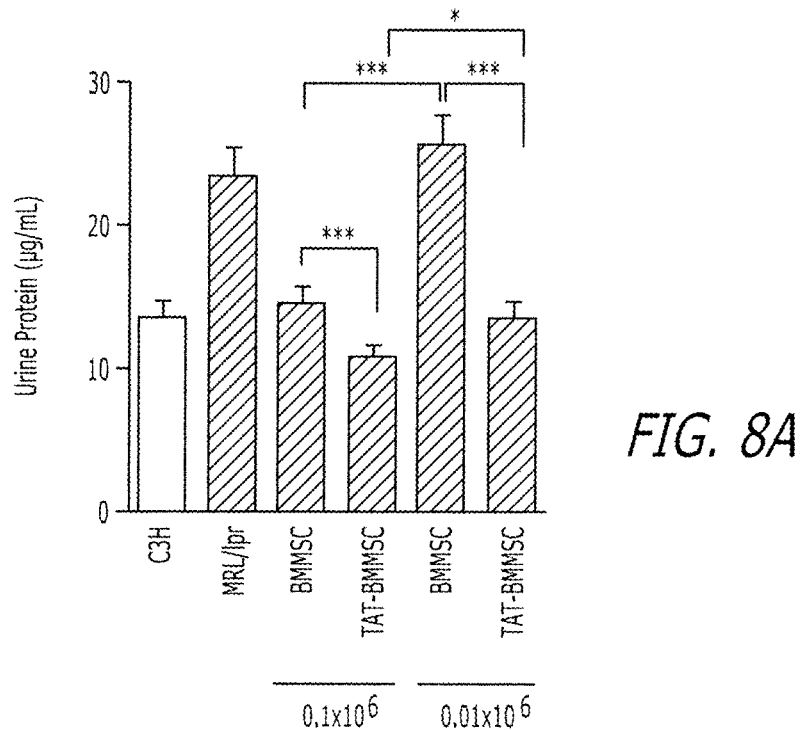
FIGS. 8A-8G show that aspirin-treated BMMSCs showed improved therapeutic effect on SLE-like MRL/lpr mice.
Figure 8B:
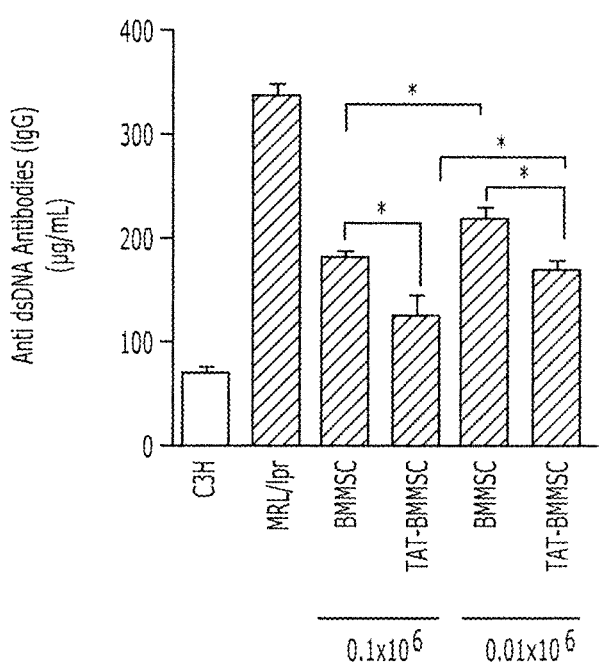
Figure 8C:
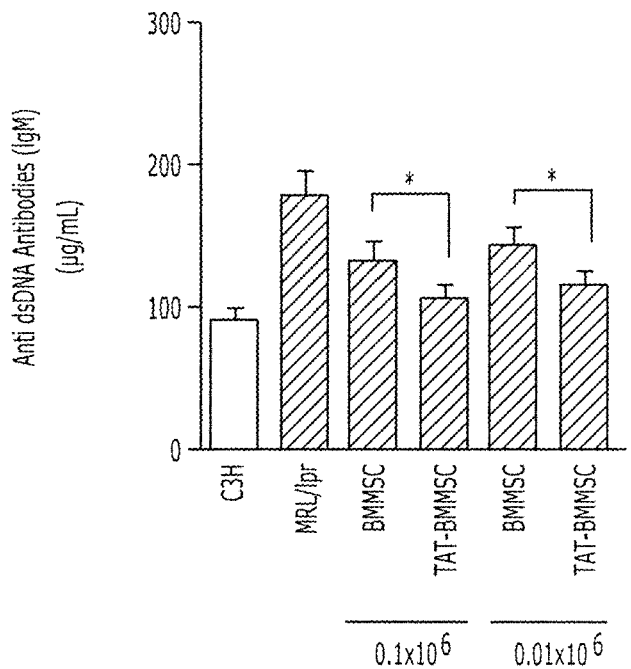
Figure 8D:
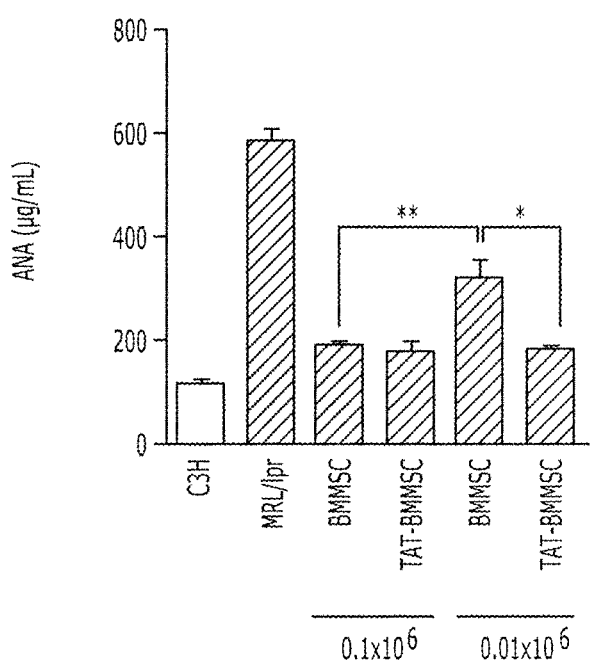
Figure 8E:
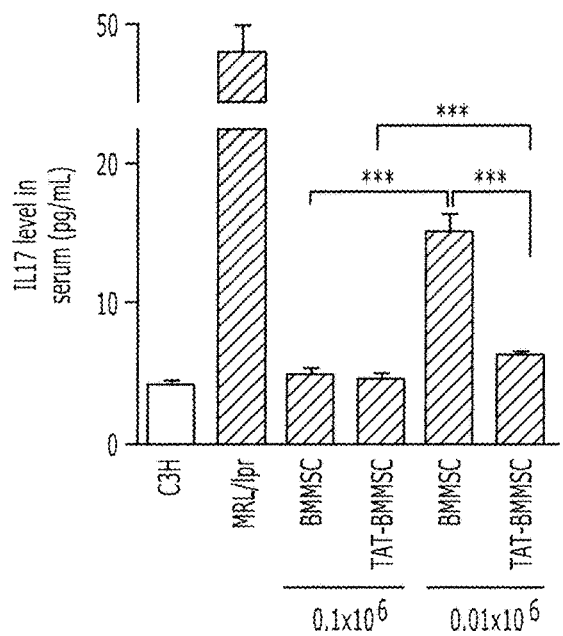
Figure 8F:
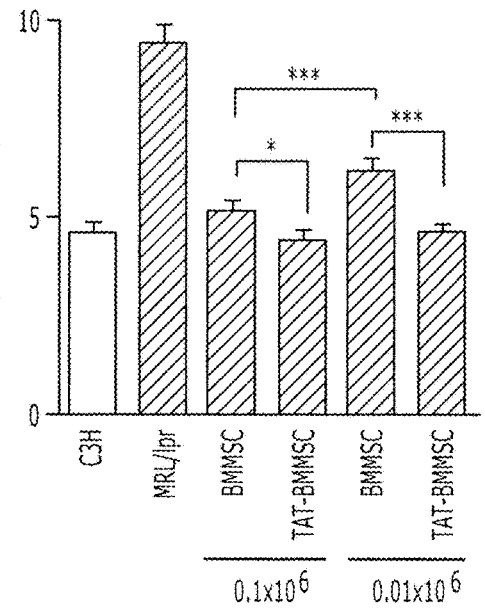
Figure 8G:
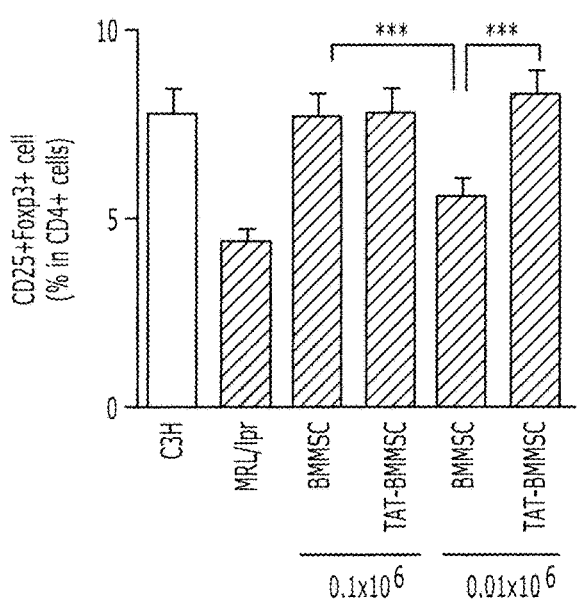
Figure 9A:
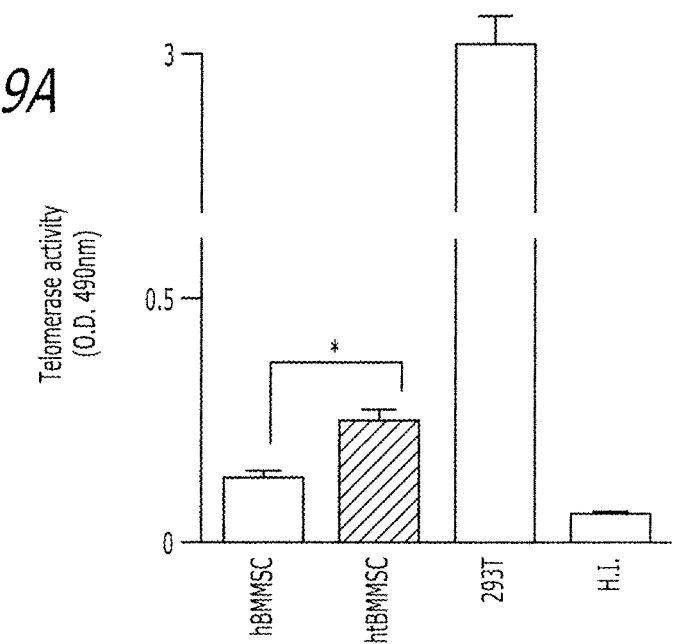
FIGS. 9A-9E show that human bone marrow contains tBMMSCs.
Figure 9B:
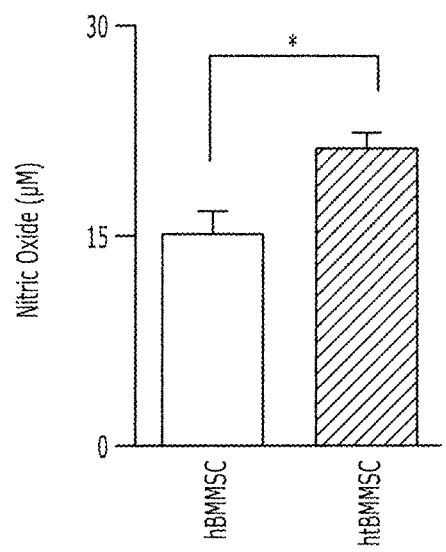
Figure 9C:
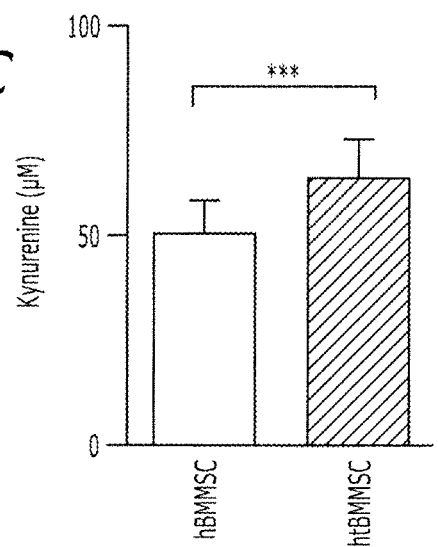
Figure 9D:
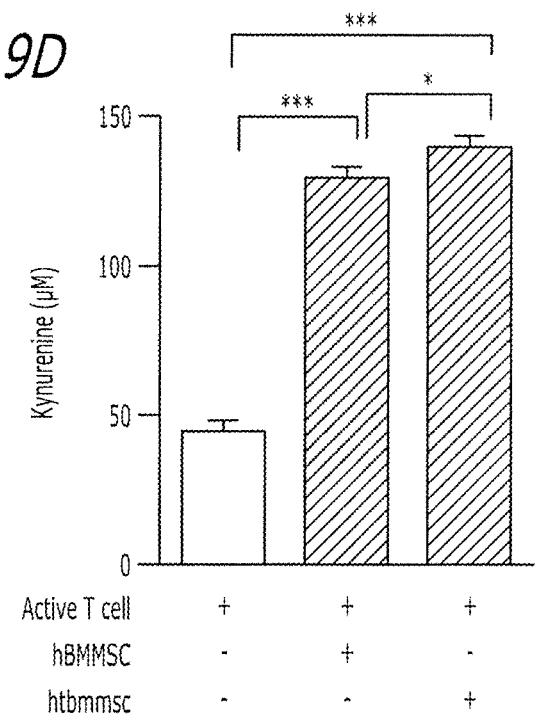
Figure 9E:
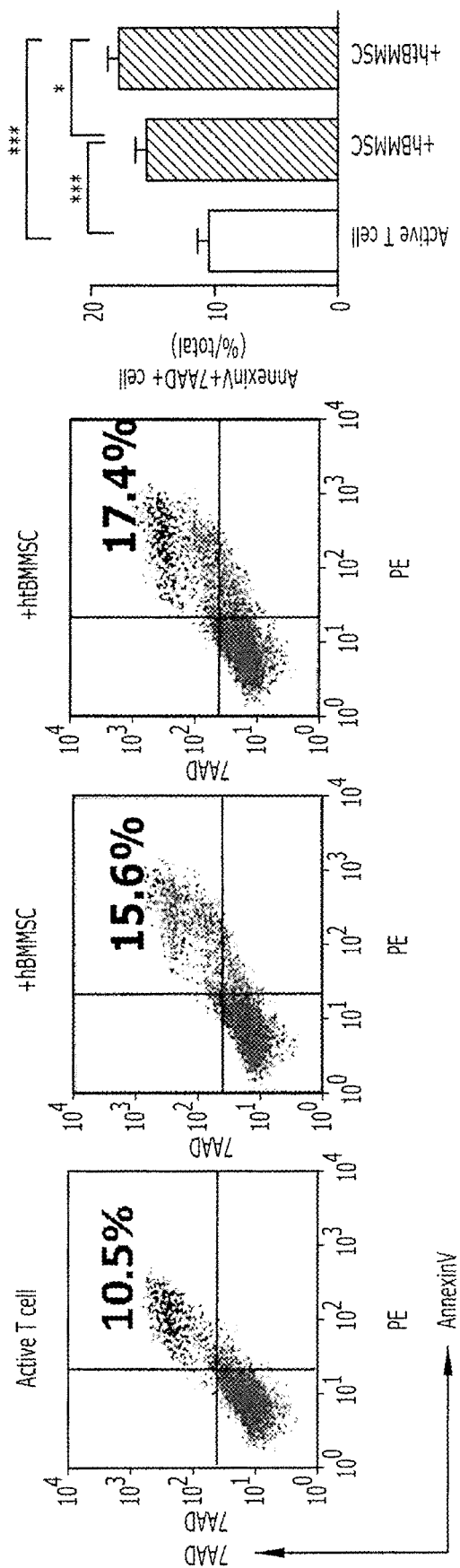

In order to confirm therapeutic effect of aspirin (TAT)-treated BMMSCs (TAT-BMMSC), we infused either 0.1×10$^6$ or 0.01×10$^6$ TAT-BMMSC into MRL/lpr mice at 10 weeks of age and analyzed treatment response at 12 weeks of age. We found that both aspirin treated TAT-BMMSC and BMMSC were capable of reducing the urine protein level when compared to MRL/lpr mice (FIG. 8A). TAT-BMMSC were more effective in reducing the overall urine protein levels at both 0.1×10$^6$ and 0.01×10$^6$ groups when compared to BMMSC. It appeared that infusion of 0.01×10$^6$ BMMSCs fail to significantly reduce urine protein levels (FIGS. 8A). Although TAT-BMMSC and BMMSC infusion showed significant decreased levels of dsDNA IgG, IgM antibodies and ANA in peripheral blood (FIGS. 8B-D), TAT-BMMSC showed superior therapeutic effect in reducing dsDNA IgG and IgM antibodies and ANA levels when compared to BMMSC group at both 0.1×10$^6$ and 0.01×10$^6$ groups (FIGS. 8B-D). Additionally, ELISA and flow cytometric analysis revealed that TAT-BMMSC show more effectiveness in reducing serum IL17 levels in 0.01×10$^6$ group (FIG. 8E) and number of CD4$^+$IL17$^+$IFNγ$^-$T-Iymphocytes in both 0.1×10$^6$ and 0.01×10$^6$ groups (FIG. 8F) and elevating the level of CD4$^+$CD25$^+$Foxp3$^+$ Tregs in 0.01×10$^6$ group when compared to BMMSCs (FIG. 8G). These data indicate that the number of BMMSCs in immuno-therapy could be significantly reduced with ex vivo telomerase activator treatment.

Example 7

Human bone marrow contain tBMMSCs and aspirin treatment can induce regular human BMMSC to become tBMMSCs with improved immunomodulatory function.

When aspirin was added into culture medium at 2.5 μg/ml or 50 μg/ml for 1 week, there is a significantly increased level of telomerase activity in BMMSCs.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

All references cited herein, including but not limited to patents, patent applications, and non-patent literature, are hereby incorporated by reference herein in their entirety.

REFERENCES

Aggarwal, S., and Pittenger, M. F. (2005) Human mesenchymal stem cells modulate allogeneic immune cell responses. Blood 105, 1815-1822.

Anjos-Afonso, F., Bonnet, D. (2007) Nonhematopoietic/endothelial SSEA-1+ cells define the most primitive progenitors in the adult murine bone marrow mesenchymal compartment. Blood 109, 1298-1306.

Augello, A., Tasso, R., Negrini, S. M., Cancedda, R., Pennesi, G. (2007) Cell therapy using allogeneic bone marrow mesenchymal stem cells prevents tissue damage in collagen-induced arthritis. Arthritis Rheum. 56, 1175-1186.

Bernardo, M. E., Locatelli, F., Fibbe, W. E. (2009) *Mesenchymal stromal cells*. Ann N Y Acad Sci. 1176, 101-17.

Bianco, P., Riminucci, M., Gronthos, S., Robey, P. G. (2001) Bone marrow stromal stem cells: nature, biology, and potential applications. Stem Cells 19, 180-192.

Bogdan, C. Nitric oxide and the immune response. (2001) Nat. Immunol. 2, 907-916.

Bühring, Battula, V. L., Treml, S., Schewe, B., Kanz, L., Vogel, W. (2007) Novel markers for the prospective isolation of human MSC. Ann N. Y. Acad. Sci. 1106, 262-271.

Chen, X., Armstrong, M. A., Li, G. (2006) Mesenchymal stem cells in immunoregulation. Immunol. Cell Biol. 84, 413-421.

Chen, X. D., Dusevich, V., Feng, J. Q., Manolagas, S. C., Jilka, R. L. (2007) Extracellular matrix made by bone marrow cells facilitates expansion of marrow-derived mesenchymal progenitor cells and prevents their differentiation into osteoblasts. J. Bone Miner. Res. 22, 1943-1956.

Clarke, E., McCann, S. R. (1989) Age dependent in vitro stromal growth. Bone Marrow Transplant 4, 596-597.

Conget, P. A., Minguell J. J. (1999) Phenotypical and functional properties of human bone marrow mesenchymal progenitor cells. J. Cell Physiol. 181, 67-73.

Copland, I., Sharma, K., Lejeune, L., Eliopoulos, N., Stewart, D., Liu, P., Lachapelle, K., Galipeau, J. (2008) *CD34 expression on murine marrow-derived mesenchymal stromal cells; impact on neovascularization*. Exp. Hematol. 36, 93-103.

Covas, D. T., Panepucci, R. A., Fontes, A. M., Silva W. A. Jr., Orellana M. D., Freitas M. C., Neder L., Santos A. R., Peres. L C., Jamur M. C., Zago, M. A. (2008) Multipotent mesenchymal stromal cells obtained from diverse human tissues share functional properties and gene-expression profiles with CD146+ perivascular cells and fibroblasts. Exp. Hematol. 36, 642-654.

Deschaseaux, F., Gindraux, F., Saadi, R., Obert, L., Chalmers, D., Nerve, P. (2003) Direct selection of human bone marrow mesenchymal stem cells using an anti-CD49a antibody reveals their CD45med, low phenotype. Br. J. Haematol. 122, 506-517.

Eghbali-Fatourechi, G., Lamsam, J., Fraser, D., Nagel, D., Riggs, B. L., Khosla, S. (2005) Circulating osteoblast-lineage cells in humans. N. Engl. J. Med. 352, 1959-1966.

Friedenstein, A. J., Chailakhjan, R. K., Lalykina, K. S. (1970) The development of fibroblast colonies in monolayer cultures of guinea-pig bone marrow and spleen cells. Cell Tissue Kinet. 3, 393-403.

Friedenstein, A. J., Chailakhyan, R. K., Latsinik, N. V., Panasyuk, A. F., Keiliss-Borok, I.V. (1974) Stromal cells responsible for transferring the microenvironment of the hemopoietic tissues. Cloning in vitro and retransplantation in vivo. Transplantation 17, 331-340.

Dillon, R. L., White, D. E., Muller, W. J. (2007) The phosphatidyl inositol 3-kinase signaling network: implications for human breast cancer. Oncogene 26, 1338-1345.

Friedenstein, A. J. (1980) Stromal mechanisms of bone marrow: cloning in vitro and retransplantation in vivo. Haematol. Blood Transfus 25, 19-29.

Galmiche, M. C., Koteliansky, V. E., Brière, J., Hervé, P., Charbord, P. (1993) Stromal cells from human long-term marrow cultures are mesenchymal cells that differentiate following a vascular smooth muscle differentiation pathway. Blood 82, 66-76.

Gang, E. J., Bosnakovski, D., Figueiredo, C. A., Visser. J. W., Perlingeiro, R. C. (2007) SSEA-4 identifies mesenchymal stem cells from bone marrow. Blood 109, 1743-1751.

González, M. A., Gonzalez-Rey, E., Rico, L., Büscher, D., Delgado, M. (2009) Adipose-derived mesenchymal stem cells alleviate experimental colitis by inhibiting inflammatory and autoimmune responses. Gastroenterology 136, 978-989.

Grasselli, A., Nanni, S., Colussi, C., Aiello, A., Benvenuti, V., Ragone, G., Moretti, F., Sacchi, A., Bacchetti, S., Gaetano, C., Capogrossi, M. C., Pontecorvi, A., Farsetti. A. (2008) Estrogen receptor-alpha and endothelial nitric oxide synthase nuclear complex regulates transcription of human telomerase. Circ. Res. 103, 34-42.

Greco, S. J., Liu, K., Rameshwar, P. (2007) Functional similarities among genes regulated by OCT4 in human mesenchymal and embryonic stem cells. Stem Cells 25, 3143-3154.

Gronthos, S., Simmons, P. J. (1995) The growth factor requirements of STRO-1-positive human bone marrow stromal precursors under serum-deprived conditions in vitro. Blood 85, 924-940

Gronthos, S., Simmons, P. J., Graves, S. E., Robey, P. G. (2001) Integrin-mediated interactions between human bone marrow stromal precursor cells and the extracellular matrix. Bone 28, 174-181

Gronthos, S., Zannettino, A. C., Hay, S. J., Shi, S., Graves, S. E., Kortesidis, A., Simmons, P. J. (2003) Molecular and cellular characterisation of highly purified stromal stem cells derived from human bone marrow. J. Cell Sci. 116, 1827-1835.

Haynesworth, S. E., Baber, M. A., Caplan, A. I. (1992) Cell surface antigens on human marrow-derived mesenchymal cells are detected by monoclonal antibodies. Bone 13, 69-80.

Henson, E. S., Gibson, S. B. (2006) Surviving cell death through epidermal growth factor (EGF) signal transduction pathways: implications for cancer therapy. Cell Signal. 18, 2089-2097.

Jones, E. A., Kinsey, S. E., English, A., Jones, R. A., Straszynski, L., Meredith, D. M., Markham, A. F., Jack, A., Emery, P., McGonagle, D. (2002) Isolation and characterization of bone marrow multipotential mesenchymal progenitor cells. Arthritis Rheum. 46, 3349-3360.

Koç, O. N., Gerson, S. L., Cooper, B. W., Dyhouse, S. M., Haynesworth, S. E., Caplan, A. I., Lazarus, H. M. (2000) Rapid hematopoietic recovery after coinfusion of autologous-blood stem cells and culture-expanded marrow mesenchymal stem cells in advanced breast cancer patients receiving high-dose chemotherapy. J. Clin. Oncol. 18, 307-316.

Kwan, M. D., Slater, B. J., Wan, D. C., Longaker, M. T. (2008) Cell-based therapies for skeletal regenerative medicine. Hum. Mol. Genet. 17, R93-98.

Le Blanc, K. Frassoni, F. Ball, L., Locatelli, F. Roelofs, H., Lewis, I., Lanino, E., Sundberg, B., Bernardo, M. E., Remberger, M., Dini, G., Egeler, R. M., Bacigalupo, A., Fibbe, W., Ringdén, O. (2004) Treatment of severe acute graft-versus-host disease with third party haploidentical mesenchymal stem cells. Lancet 363, 1439-1441.

Lee, R. H., Seo, M. J., Reger, R. L., Spees, J. L., Pulin, A. A., Olson, S. D., Prockop, D. J. (2006) Multipotent stromal cells from human marrow home to and promote repair of pancreatic islets and renal glomeruli in diabetic NOD/scid mice. Proc. Natl. Acad. Sci. USA 103, 17438-17443.

Liu, Y., Zheng, Y., Ding, G., Zhang, C., Bartold, P. M., Gronthos, S., Shi, S., Wang, S. (2008) Periodontal ligament stem cell-mediated treatment for periodontitis in miniature swine. Stem Cells 26, 1065-1073.

Lund, T. C., Tolar, J., Orchard, P. J. (2008) *Granulocyte colony-stimulating factor mobilized CFU-F can be found in the peripheral blood but have limited expansion potential*. Haematologica. 93, 908-912.

Martinez, C., Hofmann, T. J., Marino, R., Dominici, M., Horwitz, E. M. (2007) Human bone marrow mesenchymal stromal cells express the neural ganglioside GD2: a novel surface marker for the identification of MSCs. Blood 109, 4245-4248.

Miura, M., Chen, X-D., Allen, M. R., Bi, Y., Gronthos, S., Seo, B-M., Lakhani, S., Flavell, R. A., Feng, X-H., Robey, P. G., Young, M., and Shi, S. (2004) A crucial role of Caspase-3 in osteogenic differentiation of bone marrow stromal stem cells. J. Clin. Invest. 114, 1704-1713.

Nauta, A. J., Fibbe, W. E. (2007) Immunomodulatory properties of mesenchymal stromal cells. Blood 110, 3499-3506.

Németh, K., Leelahavanichkul, A., Yuen, P. S., Mayer, B., Parmelee, A., Doi, K., Robey, P. G., Leelahavanichkul, K., Koller, B. H., Brown, J. M., Hu, X., Jelinek, I., Star, R. A., Mezey, E. (2009) Bone marrow stromal cells attenuate sepsis via prostaglandin E (2)-dependent reprogramming of host macrophages to increase their interleukin-10 production. Nat. Med. 15, 42-49.

Niedbala, W., Cai, B., Liu, H., Pitman, N., Chang, L., Liew, F. Y. (2007) Nitric oxide induces CD4+CD25+Foxp3 regulatory T cells from CD4+CD25 T cells via p53, IL-2, and OX40. Proc Natl. Acad. Sci. USA. 104, 15478-15483.

Noort, W. A., Kruisselbrink, A. B., in't Anker, P. S., Kruger, M., van Bezooijen, R. L., de Paus, R. A., Heemskert, M. H. Löwik, C. W., Falkenburg, J. H., Willemze, R., Fibbe W. E. (2002) Mesenchymal stem cells promote engraftment of human umbilical cord blood-derived CD34 cells in NOD/SCID mice. Exp. Hematol. 30, 870-878.

Ogawa, M., Larue, A. C., Watson, P. M., Watson, D. K. (2010) *Hematopoietic stem cell origin of mesenchymal cells: opportunity for novel therapeutic approaches*. Int. J. Hematol. 91, 353-359.

Olmsted-Davis, E. A., Gugala, Z., Camargo, F., Gannon, F. H., Jackson, K., Kienstra, K. A., Shine, H. D., Lindsey, R. W., Hirschi, K. K., Goodell, M. A., Brenner, M. K., Davis, A. R. (2003) *Primitive adult nemato oietic stem cells can function as osteoblast precursors*. Proc. Natl. Acad. Sci. USA. 100, 15877-15882.

Owen, M., Friedenstein, A. J. (1988) Stromal stem cells: marrow-derived osteogenic precursors. Ciba. Found Symp. 136, 42-60.

Panetta, N. J., Gupta, D. M., Quarto, N., Longaker, M. T. (2009) Mesenchymal cells for skeletal tissue engineering. Panminerva Med. 51, 25-41.

Parekkadan, B., Tilles, A. W., Yarmush, M. L. (2008) Bone marrow-derived mesenchymal stem cells ameliorate autoimmune enteropathy independent of regulatory T cells. Stem Cells 26, 1913-1919.

Park, J. I., Venteicher, A. S., Hong, J. Y., Choi, J., Jun, S., Shkreli, M., Chang, W., Meng, Z., Cheung, P., Ji, H., McLaughlin, M., Veenstra, T. D., Nusse, R., McCrea, P. D., Artandi, S. E. (2009) *Telomerase modulates Wnt signalling by association with target gene chromatin*. Nature. 460, 66-72.

Pittenger, M. F., Mackay, A. M., Beck, S. C., Jaiswal, R. K., Douglas, R., Mosca, J. D., Moorman, M. A., Simonetti, D. W., Craig, S., Marshak, D. R. (1999) Multilineage potential of adult human mesenchymal stem cells. Science 284, 143-147.

Polchert, D., Sobinsky, J., Douglas, G. W., Kidd, M., Moadsiri, A., Reina, E., Genrich, K., Mehrotra, S., Setty. S., Smith, B., Bartholomew A. (2008) IFN-γ activation of mesenchymal stem cells for treatment and prevention of graft versus host disease. Eur. J. Immunol. 38, 1745-1755.

Prockop, D. J. (1997) Marrow stromal cells as stem cells for nonhematopoietic tissues. Science 276, 71-74.

Quirici, N., Soligo, D., Bossolasco, P., Servida, F., Lumini, C., Deliliers, G. L. (2002) Isolation of bone marrow mesenchymal stem cells by anti-nerve growth factor receptor antibodies. Exp Hematol. 30, 783-791.

Ren, G., Zhang, L., Zhao, X., Xu, G., Zhang, Y., Roberts, A. I., Zhao, R. C., Shi, Y. (2008) *Mesenchymal stem cell-mediated immunosuppression occurs via concerted action of chemokines and nitric oxide*. Cell Stem Cell. 2, 141-150.

Sacchetti, B., Funari, A., Michienzi, S., Di Cesare, S., Piersanti, S., Saggio, I., Tagliafico, E., Ferrari, S., Robey, P. G., Riminucci, M., Bianco, P. (2007) Self-renewing osteoprogenitors in bone marrow sinusoids can organize a hematopoietic microenvironment. Cell 131, 324-336.

Sato, K., Ozaki, K., Oh, I., Meguro, A., Hatanaka, K., Nagai, T., Muroi, K., Ozawa, K. (2007) Nitric oxide plays a critical role in suppression of T-cell proliferation by mesenchymal stem cells. Blood 109, 228-234.

Simmons, P. J., Torok-Storb, B. (1991) Identification of stromal cell precursors in human bone marrow by a novel monoclonal antibody, STRO-1. Blood 78, 55-62.

Simmons, P. J., Torok-Storb, B. (1991) CD34 expression by stromal precursors in normal human adult bone marrow. Blood 78, 2848-2853.

Shi, S., Gronthos, S. (2003) Perivascular niche of postnatal mesenchymal stem cells in human bone marrow and dental pulp. J. Bone Miner. Res. 18, 696-704.

Shi, S., Gronthos, S., Chen, S., Counter, C. M., Robey, P. G., and Wang, C-Y. (2002) Bone formation by human postnatal bone marrow stromal stem cells is enhanced by telomerase expression. Nat. Biotechnol. 20, 587-591.

Short, B., Brouard, N., Occhiodoro-Scott, T., Ramakrishnan, A., Simmons, P. J. (2003) Mesenchymal stem cells. Arch. Med. Res. 34, 565-571.

Sordi, V., Malosio, M. L., Marchesi, F., Mercalli, A., Melzi, R., Giordano, T., Belmonte, N., Ferrari, G., Leone, B. E., Bertuzzi, F., Zerbini, G., Allavena, P., Bonifacio, E., Piemonti, L. (2005) Bone marrow mesenchymal stem cells express a restricted set of functionally active chemokine receptors capable of promoting migration to pancreatic islets. Blood 106, 419-427.

Sun, L., Akiyama, K., Zhang, H., Yamaza, T., Hou, Y., Zhao, S., Xu, T., Le, A., Shi, S. (2009) Mesenchymal Stem Cell Transplantation Reverses Multi-Organ Dysfunction in Systemic Lupus Erythematosus Mice and Humans. Stem Cells 27, 1421-1432.

Tessier, M., Woodgett, J. R. (2006) Serum and glucocorticoid-regulated protein kinases: variations on a theme. J. Cell Biochem. 98, 1391-1407.

Uccelli, A., Moretta, L., Pistoia, V. (2008) Mesenchymal stem cells in health and disease. Nat Rev Immunol 8, 726-736.

Uccelli, A., Pistoia, V., Moretta, L. (2007) Mesenchymal stem cells: a new strategy for immunosuppression? Trends Immunol. 28, 219-226.

Włodarski, K. H., Galus, R., Włfodarski, P. (2004) *Non-adherent bone marrow cells are a rich source of cells forming bone in vivo.* Folia Biol (Praha). 50, 167-73.

Zappia, E., Casazza, S., Pedemonte, E., Benvenuto, F., Bonanni, I., Gerdoni, E., Giunti, D., Ceravolo, A., Cazzanti, F., Frassoni, F., Mancardi, G., Uccelli, A. (2005) Mesenchymal stem cells ameliorate experimental autoimmune encephalomyelitis inducing T cell anergy. Blood 106, 1755-1761.

Zhang, Z. L., Tong, J., Lu, R. N., Scutt, A. M., Goltzman, D., Miao, D. S. (2009) Therapeutic potential of non-adherent BM-derived mesenchymal stem cells in tissue regeneration. Bone Marrow Transplant. 43, 69-81.

Zhang, X., Zanello, L. P. (2008) Vitamin D receptor-dependent 1 alpha, 25(OH)2 vitamin D3-induced anti-apoptotic PI3K/AKT signaling in osteoblasts. J. Bone Miner. Res. 23, 1238-1248.

Zhou, K., Zhang, H., Jin, O., Feng, X., Yao, G., Hou, Y., Sun, L. (2008) Transplantation of human bone marrow mesenchymal stem cell ameliorates the autoimmune pathogenesis in MRL/Ipr mice. Cell Mol. Immunol. 5, 417-424.

We claim:

1. A method of modulating the immune system of a human patient, comprising:
   a) culturing a sample of human bone marrow derived all nuclear cells in a plastic culture vessel;
   b) removing nonadherent cells that do not adhere to plastic;
   c) culturing said nonadherent cells from b) in a dish coated with extracellular matrix produced by human bone marrow derived mesenchymal stem cells (BMMSCs);
   d) sub-culturing cells that adhere to the extracellular matrix in c);
   e) isolating high telomerase human bone marrow mesenchymal stem cells (tBMMSCs) from the sub-cultured cells in d); and
   f) administering to the human patient a therapeutically effective amount of tBMMSCs.

2. The method of claim 1, wherein the human patient has an immune disorder.

3. The method of claim 1, wherein the human patient has systemic lupus erythematosus.

4. The method of claim 1, wherein the method further comprises isolating $CD34^+$ tBMMSCs.

5. The method of claim 1, wherein the method further comprises isolating $CD34^+$ tBMMSCs; and wherein at least 20% of tBMMSCs are $CD34^+$ tBMMSCs.

6. The method of claim 1, wherein the method further comprises isolating stage-specific embryonic antigen-4 positive ($SSEA4^+$) tBMMSCs.

7. The method of claim 1, wherein the method further comprises isolating $SSEA4^+$ tBMMSCs; and wherein at least 80% of tBMMSCs are $SSEA4^+$ tBMMSCs.

8. The method of claim 1, wherein the method further comprises isolating $CD34^+/CD73^+$ tBMMSCs.

9. The method of claim 1, wherein the method further comprises isolating $CD34^+/CD73^+$ tBMMSCs; and wherein at least 80% of tBMMSCs are $CD34^+/CD73^+$ tBMMSCs.

* * * * *

UNITED STATES PATENT AND TRADEMARK OFFICE
CERTIFICATE OF CORRECTION

| | | |
|---|---|---|
| PATENT NO. | : 10,736,922 B2 | Page 1 of 1 |
| APPLICATION NO. | : 15/845718 | |
| DATED | : August 11, 2020 | |
| INVENTOR(S) | : Songtao Shi et al. | |

It is certified that error appears in the above-identified patent and that said Letters Patent is hereby corrected as shown below:

In the Specification

Column 1, Lines 35-39:
Please delete:
"This invention was made with government support under Contract No. R01DE17449 awarded by the National Institute of Dental and Craniofacial Research/National Institute for Health. The government has certain rights in the invention."

And insert:
-- This invention was made with government support under R01 DE017449 awarded by the National Institutes of Health. The government has certain rights in the invention. --

Signed and Sealed this
First Day of April, 2025

Coke Morgan Stewart
*Acting Director of the United States Patent and Trademark Office*